(12) United States Patent
Bissonnette et al.

(10) Patent No.: US 11,535,670 B2
(45) Date of Patent: *Dec. 27, 2022

(54) COMBINATION THERAPIES OF HDAC INHIBITORS AND PD-L1 INHIBITORS

(71) Applicant: HUYABIO International, LLC, San Diego, CA (US)

(72) Inventors: Reid P. Bissonnette, Carlsbad, CA (US); Alain Rolland, San Diego, CA (US); Mireille Gillings, Winchester CDP, NV (US)

(73) Assignee: HUYABIO International, LLC, San Diego, CA (US)

( * ) Notice: Subject to any disclaimer, the term of this patent is extended or adjusted under 35 U.S.C. 154(b) by 496 days.

This patent is subject to a terminal disclaimer.

(21) Appl. No.: 16/541,020

(22) Filed: Aug. 14, 2019

(65) Prior Publication Data

US 2020/0181267 A1 Jun. 11, 2020

Related U.S. Application Data

(63) Continuation of application No. 15/592,929, filed on May 11, 2017, now Pat. No. 10,385,131.

(60) Provisional application No. 62/335,056, filed on May 11, 2016.

(51) Int. Cl.
| | |
|---|---|
| *A61K 39/00* | (2006.01) |
| *C07K 16/28* | (2006.01) |
| *A61P 35/00* | (2006.01) |
| *A61K 45/06* | (2006.01) |
| *A61K 31/4406* | (2006.01) |
| *A61K 39/395* | (2006.01) |

(52) U.S. Cl.
CPC ...... *C07K 16/2827* (2013.01); *A61K 31/4406* (2013.01); *A61K 39/39558* (2013.01); *A61K 45/06* (2013.01); *A61P 35/00* (2018.01); *A61K 2039/505* (2013.01); *A61K 2039/545* (2013.01); *C07K 2317/76* (2013.01)

(58) Field of Classification Search
CPC .......... C07K 16/2827; A61P 35/00; A61K 39/39558; A61K 2039/505; A61K 2300/00
See application file for complete search history.

(56) References Cited

U.S. PATENT DOCUMENTS

| | | | |
|---|---|---|---|
| 4,312,862 A | 1/1982 | Purcell et al. |
| 4,533,498 A | 8/1985 | Blaney et al. |
| 4,816,567 A | 3/1989 | Cabilly et al. |
| 4,870,074 A | 9/1989 | Kon et al. |
| 5,143,935 A | 9/1992 | Fujiwara et al. |
| 5,236,931 A | 8/1993 | Jagdmann et al. |
| 5,395,832 A | 3/1995 | Ito et al. |
| 5,401,756 A | 3/1995 | Yamamoto et al. |
| 5,500,422 A | 3/1996 | Ito et al. |
| 5,545,806 A | 8/1996 | Lonberg et al. |
| 5,545,807 A | 8/1996 | Surani et al. |
| 5,569,825 A | 10/1996 | Lonberg et al. |
| 5,610,052 A | 3/1997 | Thompson et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,686,482 A | 11/1997 | Ohmori et al. |
| 5,783,568 A | 7/1998 | Schlessinger et al. |
| 5,958,792 A | 9/1999 | Desai et al. |
| 5,993,845 A | 11/1999 | Geerts et al. |
| 6,075,181 A | 6/2000 | Kucherlapati et al. |
| 6,140,351 A | 10/2000 | Amaiz et al. |
| 6,150,584 A | 11/2000 | Kucherlapati et al. |
| 6,174,905 B1 | 1/2001 | Suzuki et al. |
| 6,326,386 B1 | 12/2001 | Watson et al. |
| 6,395,759 B1 | 5/2002 | Thompson et al. |
| 6,399,627 B1 | 6/2002 | Song et al. |
| 6,441,008 B1 | 8/2002 | Kelly et al. |
| 6,444,849 B1 | 9/2002 | Ando et al. |
| 6,465,455 B1 | 10/2002 | Brown et al. |
| 6,548,514 B1 | 4/2003 | Brown |
| 6,638,530 B1 | 10/2003 | Ishibashi et al. |
| 6,670,381 B2 | 12/2003 | Kelly et al. |
| 6,673,827 B1 | 1/2004 | Brouillette et al. |
| 6,759,414 B2 | 7/2004 | Beight et al. |
| 6,897,220 B2 | 5/2005 | Deloime et al. |
| 6,905,669 B2 | 6/2005 | DiMartino |
| 6,946,441 B2 | 9/2005 | Long et al. |
| 6,982,321 B2 | 1/2006 | Winter |
| 6,992,103 B2 | 1/2006 | Faller et al. |
| 7,005,439 B2 | 2/2006 | Eriksson et al. |
| 7,087,409 B2 | 8/2006 | Barbas, III et al. |
| 7,244,751 B2 | 7/2007 | Lu et al. |

(Continued)

FOREIGN PATENT DOCUMENTS

| | | |
|---|---|---|
| CN | 1284772 C | 11/2006 |
| CN | 102441167 B | 5/2012 |

(Continued)

OTHER PUBLICATIONS

Dong et al Cancer Chemother Pharmacol vol. 69 p. 1413 (2012) (Year: 2012).*
Al-Lazikani et al.: Standard conformations for the canonical structures of immunoglobulins. J. Mol Biology 273(4):927-948 (1997).
Anderson. The process of structure-based drug design. Chem and Biol 10:787-797 (2003).
Bissonnette et al.: The activity of the HDAC inhibitor HBI-8000 (Chidamide) combined with eribulin on 4T1 spontaneous metastasis development. Journal of Clinical Oncology 35(15 Supp.):doi 10.1200/JCO.2017.35.15_suppl.e14055 [abstract] (May 30, 2017).
Boerner et al.: J. Immunol. 147(1):86-95 (1991).
Bruggemann et al.: Designer mice: the production of human antibody repertoires in transgenic animals. Year Immunol. 7:33-40 (1993).

(Continued)

*Primary Examiner* — Sheela J. Huff
(74) *Attorney, Agent, or Firm* — Eversheds Sutherland (US) LLP

(57) ABSTRACT

Provided herein are combinations that include an HDACi and a PD-L1 inhibitor that are useful for treating cancer, including cancer resistant to PD-1 inhibitors.

12 Claims, 8 Drawing Sheets

(56) References Cited

U.S. PATENT DOCUMENTS

| | | |
|---|---|---|
| 7,550,490 B2 | 6/2009 | Lu et al. |
| 7,582,665 B2 | 9/2009 | Takemoto et al. |
| 7,645,747 B2 | 1/2010 | Boojamra et al. |
| 7,683,063 B2 | 3/2010 | Kyle et al. |
| 7,981,893 B2 | 7/2011 | Mortensen et al. |
| 7,993,626 B2 | 8/2011 | McBride et al. |
| 8,088,793 B2 | 1/2012 | Qian et al. |
| 8,153,595 B2 | 4/2012 | Chen |
| 8,163,896 B1 | 4/2012 | Bentwich |
| 8,207,316 B1 | 6/2012 | Bentwich |
| 8,518,972 B2 | 8/2013 | Man et al. |
| 8,779,105 B2 | 7/2014 | Korman et al. |
| 8,957,047 B2 | 2/2015 | Paya Cuenca et al. |
| 8,993,622 B2 | 3/2015 | Wadell et al. |
| 9,005,613 B2 | 4/2015 | Liu et al. |
| 9,028,833 B2 | 5/2015 | Govindan et al. |
| 9,226,934 B2 | 1/2016 | Tahara et al. |
| 9,266,883 B2 | 2/2016 | Buschmann et al. |
| 9,315,567 B2 | 4/2016 | Chang et al. |
| 9,345,718 B1 | 5/2016 | Weichert et al. |
| 9,351,997 B2 | 5/2016 | Bender et al. |
| 9,365,496 B2 | 6/2016 | Cerundolo et al. |
| 9,375,489 B2 | 6/2016 | Govindan et al. |
| 9,382,329 B2 | 7/2016 | Chang et al. |
| 9,388,161 B2 | 7/2016 | Bair et al. |
| 9,399,028 B2 | 7/2016 | Tavazoie. et al. |
| 9,402,905 B2 | 8/2016 | Wucherpfenning et al. |
| 9,422,281 B2 | 8/2016 | Bair et al. |
| 9,440,968 B2 | 9/2016 | Huck et al. |
| 9,446,148 B2 | 9/2016 | Markovic et al. |
| 9,457,019 B2 | 10/2016 | Flynn et al. |
| 9,469,613 B2 | 10/2016 | Brown et al. |
| 9,469,876 B2 | 10/2016 | Kuslich et al. |
| 9,475,798 B2 | 10/2016 | Govek et al. |
| 9,480,754 B2 | 11/2016 | Weichert et al. |
| 9,499,523 B2 | 11/2016 | Kim et al. |
| 9,522,912 B2 | 12/2016 | Bacon et al. |
| 9,526,710 B2 | 12/2016 | Tavazoie et al. |
| 9,533,058 B2 | 1/2017 | Markovic et al. |
| 9,533,988 B2 | 1/2017 | Buschmann et al. |
| 9,549,932 B2 | 1/2017 | Wortmann et al. |
| 9,555,128 B2 | 1/2017 | Markovic et al. |
| 9,565,736 B2 | 2/2017 | Aliakseyeu et al. |
| 9,566,350 B2 | 2/2017 | Markovic et al. |
| 9,573,901 B2 | 2/2017 | Lu et al. |
| 9,580,443 B2 | 2/2017 | Lan et al. |
| 9,586,952 B2 | 3/2017 | Smith et al. |
| 9,605,070 B2 | 3/2017 | Sabatos-Peyton et al. |
| 9,617,336 B2 | 4/2017 | Cojocaur et al. |
| 9,624,195 B2 | 4/2017 | Hu et al. |
| 9,624,246 B2 | 4/2017 | Chen et al. |
| 9,629,926 B2 | 4/2017 | Govindan et al. |
| 9,630,978 B2 | 4/2017 | Cai et al. |
| 9,631,013 B2 | 4/2017 | Modelska et al. |
| 9,631,018 B2 | 4/2017 | Noelle et al. |
| 9,636,328 B2 | 5/2017 | Liu et al. |
| 9,655,880 B2 | 5/2017 | Govek et al. |
| 9,662,311 B2 | 5/2017 | Liu et al. |
| 9,670,205 B2 | 6/2017 | Aktoudianakis et al. |
| 9,676,757 B2 | 6/2017 | Sherer et al. |
| 9,682,084 B2 | 6/2017 | Carra et al. |
| 9,682,143 B2 | 6/2017 | Chang et al. |
| 9,683,048 B2 | 6/2017 | Freeman et al. |
| 9,694,088 B2 | 7/2017 | Govindan et al. |
| 9,695,200 B2 | 7/2017 | Jacobsen et al. |
| 9,701,677 B2 | 7/2017 | Jansa et al. |
| 9,707,195 B2 | 7/2017 | Tavazoie et al. |
| 9,707,302 B2 | 7/2017 | Goldenberg et al. |
| 9,708,324 B2 | 7/2017 | Chen et al. |
| 9,708,342 B2 | 7/2017 | Carra et al. |
| 9,725,473 B2 | 8/2017 | Vankayalapati et al. |
| 9,730,936 B2 | 8/2017 | Baszczynski et al. |
| 9,732,119 B2 | 8/2017 | Sun et al. |
| 9,738,646 B2 | 8/2017 | Brown et al. |
| 9,751,832 B2 | 9/2017 | Sotomayor et al. |
| 9,765,060 B2 | 9/2017 | Evarts et al. |
| 9,770,446 B2 | 9/2017 | Buchstaller et al. |
| 9,771,363 B2 | 9/2017 | Ibrahim et al. |
| 9,771,585 B2 | 9/2017 | Rodman et al. |
| 9,775,844 B2 | 10/2017 | Kutok et al. |
| 10,017,492 B2 | 7/2018 | Ge et al. |
| 10,287,353 B2 | 5/2019 | Bissonnette et al. |
| 10,385,130 B2 | 8/2019 | Bissonnette et al. |
| 10,385,131 B2 | 8/2019 | Bissonnette et al. |
| 2002/0102604 A1 | 8/2002 | Edwards et al. |
| 2002/0103192 A1 | 8/2002 | Curtin et al. |
| 2002/0115716 A1 | 8/2002 | Chaturvedi et al. |
| 2005/0054647 A1 | 3/2005 | Schuppan et al. |
| 2005/0149080 A1 | 7/2005 | Hunter et al. |
| 2005/0149158 A1 | 7/2005 | Hunter et al. |
| 2005/0165488 A1 | 7/2005 | Hunter et al. |
| 2005/0175663 A1 | 8/2005 | Hunter et al. |
| 2005/0177225 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0183728 A1 | 8/2005 | Hunter et al. |
| 2005/0191331 A1 | 9/2005 | Hunter et al. |
| 2005/0215601 A1 | 9/2005 | Aono et al. |
| 2006/0147492 A1 | 7/2006 | Hunter et al. |
| 2007/0292351 A1 | 12/2007 | Li et al. |
| 2009/0124631 A1 | 5/2009 | Li et al. |
| 2009/0275633 A1 | 11/2009 | Esteller et al. |
| 2009/0280153 A1 | 11/2009 | Hunter et al. |
| 2011/0053164 A1 | 3/2011 | Buggy et al. |
| 2011/0118298 A1 | 5/2011 | Fritz et al. |
| 2011/0135739 A1 | 6/2011 | Carter et al. |
| 2011/0159023 A1 | 6/2011 | Langemiann |
| 2012/0010229 A1 | 1/2012 | Macdougall et al. |
| 2012/0010230 A1 | 1/2012 | Macdougall et al. |
| 2013/0005707 A1 | 1/2013 | Bahmanyar et al. |
| 2013/0189364 A1 | 7/2013 | Sabin |
| 2014/0141986 A1 | 5/2014 | Spetzler et al. |
| 2014/0148350 A1 | 5/2014 | Spetzler et al. |
| 2014/0194479 A1 | 7/2014 | Schmauss et al. |
| 2014/0220580 A1 | 8/2014 | Brown et al. |
| 2014/0228233 A1 | 8/2014 | Pawlowski et al. |
| 2014/0294765 A1 | 10/2014 | Cojocaru et al. |
| 2014/0294898 A1 | 10/2014 | Miller et al. |
| 2014/0349938 A1 | 11/2014 | Reed et al. |
| 2015/0025012 A1 | 1/2015 | MacDougall et al. |
| 2015/0071910 A1* | 3/2015 | Kowanetz .......... G06Q 30/0241 424/133.1 |
| 2015/0087673 A1 | 3/2015 | Hitoshi et al. |
| 2015/0094518 A1 | 4/2015 | Wu et al. |
| 2015/0132255 A1 | 5/2015 | Sorensen et al. |
| 2015/0140036 A1 | 5/2015 | Mannick et al. |
| 2015/0152140 A1 | 6/2015 | Sorensen et al. |
| 2015/0152474 A1 | 6/2015 | Pawlowski et al. |
| 2015/0174235 A1 | 6/2015 | Hoie et al. |
| 2015/0216843 A1 | 8/2015 | Fearon |
| 2015/0258080 A1 | 9/2015 | Hager et al. |
| 2015/0258099 A1 | 9/2015 | Hager et al. |
| 2015/0259420 A1 | 9/2015 | Triebel et al. |
| 2015/0272980 A1 | 10/2015 | Rodrigueza et al. |
| 2015/0284360 A1 | 10/2015 | Chen et al. |
| 2015/0284416 A1 | 10/2015 | Zhao et al. |
| 2015/0301058 A1 | 10/2015 | Schettini et al. |
| 2015/0314017 A1 | 11/2015 | Zhao et al. |
| 2015/0322155 A1 | 11/2015 | Zhao |
| 2015/0337027 A1 | 11/2015 | Hill et al. |
| 2015/0361054 A1 | 12/2015 | Cai et al. |
| 2015/0361068 A1 | 12/2015 | Cai et al. |
| 2015/0361070 A1 | 12/2015 | Evarts et al. |
| 2015/0361095 A1 | 12/2015 | Du et al. |
| 2016/0008374 A1 | 1/2016 | Geleziunas et al. |
| 2016/0016951 A1 | 1/2016 | Schiemann et al. |
| 2016/0040163 A1 | 2/2016 | Rodrigueza et al. |
| 2016/0041153 A1 | 2/2016 | Brown et al. |
| 2016/0046716 A1 | 2/2016 | Wucherpfennig et al. |
| 2016/0067255 A1 | 3/2016 | Babusis et al. |
| 2016/0067337 A1 | 3/2016 | Barnhart et al. |
| 2016/0083368 A1 | 3/2016 | Brizgys et al. |
| 2016/0090378 A1 | 3/2016 | Kahraman et al. |

(56) References Cited

U.S. PATENT DOCUMENTS

| | | |
|---|---|---|
| 2016/0095850 A1 | 4/2016 | Cooper et al. |
| 2016/0096834 A1 | 4/2016 | Gaillard et al. |
| 2016/0097769 A1 | 4/2016 | Martin et al. |
| 2016/0108123 A1 | 4/2016 | Freeman et al. |
| 2016/0122430 A1 | 5/2016 | Gish et al. |
| 2016/0137696 A1 | 5/2016 | Gillman et al. |
| 2016/0137730 A1 | 5/2016 | Abrams et al. |
| 2016/0145252 A1 | 5/2016 | Jorand-Lebrun et al. |
| 2016/0166546 A1 | 6/2016 | Garner et al. |
| 2016/0166685 A1 | 6/2016 | Cheung et al. |
| 2016/0175284 A1 | 6/2016 | Labadie et al. |
| 2016/0175289 A1 | 6/2016 | Labadie et al. |
| 2016/0175386 A1 | 6/2016 | Mapelli et al. |
| 2016/0176928 A1 | 6/2016 | Sun et al. |
| 2016/0176962 A1* | 6/2016 | Murriel ............... C12N 15/113 424/136.1 |
| 2016/0186266 A1 | 6/2016 | Alarcon |
| 2016/0193218 A1 | 7/2016 | Quinn et al. |
| 2016/0193357 A1 | 7/2016 | Govindan et al. |
| 2016/0200752 A1 | 7/2016 | Reiley et al. |
| 2016/0200815 A1* | 7/2016 | Feldman ............... G01N 33/686 424/139.1 |
| 2016/0201063 A1 | 7/2016 | Ozsolak |
| 2016/0220573 A1 | 8/2016 | Di Paolo et al. |
| 2016/0222060 A1 | 8/2016 | Miller et al. |
| 2016/0235779 A1 | 8/2016 | Marcus |
| 2016/0257690 A1 | 9/2016 | Kinsella et al. |
| 2016/0263092 A1 | 9/2016 | Wang et al. |
| 2016/0264548 A1 | 9/2016 | Qiu et al. |
| 2016/0272680 A1 | 9/2016 | Boy et al. |
| 2016/0272707 A1 | 9/2016 | Levine et al. |
| 2016/0279272 A1 | 9/2016 | Valliant et al. |
| 2016/0289311 A1 | 10/2016 | Carrier |
| 2016/0297884 A1 | 10/2016 | Kuo et al. |
| 2016/0304450 A1 | 10/2016 | Liang et al. |
| 2016/0326593 A1 | 11/2016 | Clement et al. |
| 2016/0333008 A1 | 11/2016 | Sun et al. |
| 2016/0339030 A1 | 11/2016 | Redfield et al. |
| 2016/0339090 A1 | 11/2016 | Hacohen et al. |
| 2016/0340356 A1 | 11/2016 | Fan et al. |
| 2016/0346402 A1 | 12/2016 | Lerchen et al. |
| 2016/0347742 A1 | 12/2016 | Labadie et al. |
| 2016/0354327 A1 | 12/2016 | Rahbar et al. |
| 2016/0355488 A1 | 12/2016 | Davies et al. |
| 2016/0369241 A1 | 12/2016 | Tang |
| 2016/0376283 A1 | 12/2016 | Sherer et al. |
| 2017/0000876 A1 | 1/2017 | Lundemose et al. |
| 2017/0007567 A1 | 1/2017 | Dalton et al. |
| 2017/0008857 A1 | 1/2017 | Qiu et al. |
| 2017/0009303 A1 | 1/2017 | Ahuja et al. |
| 2017/0014527 A1 | 1/2017 | Goldenberg et al. |
| 2017/0015690 A1 | 1/2017 | Tremblay et al. |
| 2017/0020886 A1 | 1/2017 | Eis et al. |
| 2017/0020929 A1 | 1/2017 | Lin et al. |
| 2017/0022275 A1 | 1/2017 | Wucherpenning et al. |
| 2017/0029419 A1 | 2/2017 | Chessari et al. |
| 2017/0036992 A1 | 2/2017 | Jandeleit et al. |
| 2017/0043009 A1 | 2/2017 | Lundemore et al. |
| 2017/0049755 A1 | 2/2017 | Villagra et al. |
| 2017/0050924 A1 | 2/2017 | Martinez et al. |
| 2017/0056352 A1 | 3/2017 | Martinez et al. |
| 2017/0056353 A1 | 3/2017 | Martinez et al. |
| 2017/0066791 A1 | 3/2017 | Martinez et al. |
| 2017/0067875 A1 | 3/2017 | Laing et al. |
| 2017/0080093 A1 | 3/2017 | Hoffman |
| 2017/0081307 A1 | 3/2017 | Jorand-Lebrun et al. |
| 2017/0081317 A1 | 3/2017 | Jorand-Lebrun et al. |
| 2017/0096409 A1 | 4/2017 | Singh et al. |
| 2017/0096431 A1 | 4/2017 | Allen et al. |
| 2017/0101391 A1 | 4/2017 | Graham et al. |
| 2017/0101464 A1 | 4/2017 | Saha et al. |
| 2017/0107577 A1 | 4/2017 | Al-Ejeh |
| 2017/0114048 A1 | 4/2017 | Cihlar et al. |
| 2017/0114098 A1 | 4/2017 | Aivado et al. |
| 2017/0114413 A1 | 4/2017 | Hahn et al. |
| 2017/0115275 A1 | 4/2017 | Rege et al. |
| 2017/0121316 A1 | 5/2017 | Aguirre Ena et al. |
| 2017/0121409 A1 | 5/2017 | Verona et al. |
| 2017/0143737 A1 | 5/2017 | Soong |
| 2017/0143777 A1 | 5/2017 | Lin et al. |
| 2017/0144996 A1 | 5/2017 | Chen et al. |
| 2017/0144997 A1 | 5/2017 | Chen et al. |
| 2017/0157230 A1 | 6/2017 | O'Dwyer |
| 2017/0165321 A1 | 6/2017 | Lundemose et al. |
| 2017/0168054 A1 | 6/2017 | Balko et al. |
| 2017/0174653 A1 | 6/2017 | Sherer et al. |
| 2017/0174695 A1 | 6/2017 | Gollner et al. |
| 2017/0174713 A1 | 6/2017 | Du et al. |
| 2017/0174762 A1 | 6/2017 | Zinzalla et al. |
| 2017/0184568 A1 | 6/2017 | Martin |
| 2017/0189382 A1 | 7/2017 | Mehrling et al. |
| 2017/0189526 A1 | 7/2017 | Zhou et al. |
| 2017/0190675 A1 | 7/2017 | Chen et al. |
| 2017/0190763 A1 | 7/2017 | Balakrishnan et al. |
| 2017/0198040 A1 | 7/2017 | Blake et al. |
| 2017/0202924 A1 | 7/2017 | Felber et al. |
| 2017/0209407 A1 | 7/2017 | Dalton et al. |
| 2017/0209574 A1 | 7/2017 | Cao et al. |
| 2017/0210804 A1 | 7/2017 | Triebel et al. |
| 2017/0216256 A1 | 8/2017 | Streatfield |
| 2017/0216302 A1 | 8/2017 | Seki |
| 2017/0217946 A1 | 8/2017 | Barfacker et al. |
| 2017/0224837 A1 | 8/2017 | Chang et al. |
| 2017/0224970 A1 | 8/2017 | Munster et al. |
| 2017/0226073 A1 | 8/2017 | Copland, III et al. |
| 2017/0226228 A1 | 8/2017 | Desir et al. |
| 2017/0231931 A1 | 8/2017 | Cuadrado Tejedor et al. |
| 2017/0233819 A1 | 8/2017 | Pu |
| 2017/0233820 A1 | 8/2017 | Kottwitz et al. |
| 2017/0233823 A1 | 8/2017 | Schroeder et al. |
| 2017/0240527 A1 | 8/2017 | Takeuchi et al. |
| 2017/0247690 A1 | 8/2017 | Quake et al. |
| 2017/0252396 A1 | 9/2017 | Rudloff et al. |
| 2017/0252432 A1 | 9/2017 | Allen et al. |
| 2017/0267759 A1 | 9/2017 | Liang et al. |
| 2017/0268001 A1 | 9/2017 | Khodarev et al. |
| 2017/0273926 A1 | 9/2017 | Levin |
| 2017/0273980 A1 | 9/2017 | Mengel et al. |
| 2017/0275269 A1 | 9/2017 | Mengel et al. |
| 2017/0275270 A1 | 9/2017 | Barfacker et al. |
| 2017/0275273 A1 | 9/2017 | Kahraman et al. |
| 2017/0283408 A1 | 10/2017 | Lu et al. |
| 2017/0320866 A1 | 11/2017 | Jiang et al. |
| 2017/0360765 A1 | 12/2017 | Jiang et al. |
| 2018/0042929 A1 | 2/2018 | Liu et al. |
| 2018/0055851 A1 | 3/2018 | Liu et al. |
| 2018/0339044 A1 | 11/2018 | Gutierrez et al. |
| 2019/0046513 A1 | 2/2019 | Bissonnette et al. |
| 2019/0194334 A1 | 6/2019 | Fernandes et al. |

FOREIGN PATENT DOCUMENTS

| | | |
|---|---|---|
| CN | 101756957 B | 11/2012 |
| CN | 101757626 B | 12/2012 |
| CN | 101837129 B | 12/2012 |
| CN | 101836989 B | 2/2013 |
| CN | 103432077 A | 12/2013 |
| CN | 104056270 A | 9/2014 |
| CN | 104069106 A | 10/2014 |
| CN | 104083763 A | 10/2014 |
| CN | 104725628 A | 6/2015 |
| CN | 104771363 A | 7/2015 |
| CN | 104892648 A | 9/2015 |
| CN | 105288648 A | 2/2016 |
| CN | 105457038 A | 4/2016 |
| CN | 105949114 A | 9/2016 |
| CN | 106821965 A | 6/2017 |
| CN | 106916101 A | 7/2017 |
| CN | 104530413 B | 8/2017 |
| CN | 107011238 A | 8/2017 |
| CN | 104530415 B | 9/2017 |
| EP | 0847992 A1 | 6/1998 |
| EP | 1000935 A1 | 5/2000 |
| EP | 1170008 A1 | 1/2002 |

(56) References Cited

FOREIGN PATENT DOCUMENTS

| | | |
|---|---|---|
| EP | 3133165 A1 | 2/2014 |
| JP | H0823980 A | 1/1996 |
| JP | H10330254 A | 12/1998 |
| JP | H11302173 A | 11/1999 |
| JP | 2000-256194 | 9/2000 |
| JP | H10152462 A | 12/2002 |
| JP | 2009-209090 A | 9/2009 |
| JP | 4360660 B2 | 11/2009 |
| JP | 2015-209376 A | 11/2015 |
| WO | WO-9110741 A1 | 7/1991 |
| WO | WO-9633735 A1 | 10/1996 |
| WO | WO-9634096 A1 | 10/1996 |
| WO | WO-9824893 A2 | 6/1998 |
| WO | WO-9905109 A1 | 2/1999 |
| WO | WO-0056153 A1 | 9/2000 |
| WO | WO-0116106 A1 | 3/2001 |
| WO | WO-0118171 A2 | 3/2001 |
| WO | WO-0170675 A2 | 9/2001 |
| WO | WO-0226696 A1 | 4/2002 |
| WO | WO-2004006909 A1 | 1/2004 |
| WO | WO-2004071400 A2 | 8/2004 |
| WO | WO 2004/103369 A1 | 12/2004 |
| WO | WO-2006082428 A2 | 8/2006 |
| WO | WO 2006/094286 A2 | 9/2006 |
| WO | WO 2006/121518 A2 | 11/2006 |
| WO | WO 2006/121521 A2 | 11/2006 |
| WO | WO 2006/121522 A2 | 11/2006 |
| WO | WO 2006/135479 A2 | 12/2006 |
| WO | WO-2007057440 A2 | 5/2007 |
| WO | WO 2007/075414 A2 | 7/2007 |
| WO | WO 2009/098451 A2 | 8/2009 |
| WO | WO 2011/060328 A1 | 5/2011 |
| WO | WO 2011/153509 A1 | 12/2011 |
| WO | WO 2013/028907 A1 | 2/2013 |
| WO | WO 2011/063309 A1 | 4/2013 |
| WO | WO 2013/079687 A1 | 6/2013 |
| WO | WO-2013085902 A1 | 6/2013 |
| WO | WO 2013/124867 A1 | 8/2013 |
| WO | WO 2014/135244 A1 | 9/2014 |
| WO | WO 2014/135245 A1 | 9/2014 |
| WO | WO 2014/144791 A2 | 9/2014 |
| WO | WO 2014/193999 A2 | 12/2014 |
| WO | WO 2015/007337 A1 | 1/2015 |
| WO | WO 2015/014442 A1 | 2/2015 |
| WO | WO 2015/014446 A1 | 2/2015 |
| WO | WO 2015/017546 A1 | 2/2015 |
| WO | WO 2015/035112 A1 | 3/2015 |
| WO | WO 2015/037000 A1 | 3/2015 |
| WO | WO 2015/061372 A1 | 4/2015 |
| WO | WO 2015/069266 A1 | 5/2015 |
| WO | WO 2015/085210 A1 | 6/2015 |
| WO | WO 2015/086738 A2 | 6/2015 |
| WO | WO 2015/096884 A1 | 7/2015 |
| WO | WO 2015/096982 A1 | 7/2015 |
| WO | WO 2015/110659 A1 | 7/2015 |
| WO | WO 2015/112900 A1 | 7/2015 |
| WO | WO 2015/113920 A1 | 8/2015 |
| WO | WO 2015/113927 A1 | 8/2015 |
| WO | WO 2015/117002 A1 | 8/2015 |
| WO | WO 2015/138920 A1 | 9/2015 |
| WO | WO 2015/149435 A1 | 10/2015 |
| WO | WO 2015/151078 A2 | 10/2015 |
| WO | WO 2015/151079 A1 | 10/2015 |
| WO | WO 2015/151080 A1 | 10/2015 |
| WO | WO 2015/157162 A1 | 10/2015 |
| WO | WO 2015/168614 A2 | 11/2015 |
| WO | WO 2015/172747 A1 | 11/2015 |
| WO | WO 2015/184405 A1 | 12/2015 |
| WO | WO 2016/005508 A1 | 1/2016 |
| WO | WO 2016/014890 A1 | 1/2016 |
| WO | WO 2016/040880 A1 | 3/2016 |
| WO | WO 2016/040882 A1 | 3/2016 |
| WO | WO 2016/040892 A1 | 3/2016 |
| WO | WO 2016/042080 A1 | 3/2016 |
| WO | WO 2016/046346 A1 | 3/2016 |
| WO | WO 2016/059622 A2 | 4/2016 |
| WO | WO 2016/061087 A1 | 4/2016 |
| WO | WO 2016/061142 A1 | 4/2016 |
| WO | WO 2016/061495 A1 | 4/2016 |
| WO | WO 2016/065349 A2 | 4/2016 |
| WO | WO-2016054555 A2 | 4/2016 |
| WO | WO 2016/066634 A2 | 5/2016 |
| WO | WO 2016/071477 A1 | 5/2016 |
| WO | WO 2016/073759 * | 5/2016 |
| WO | WO 2016/081732 A1 | 5/2016 |
| WO | WO 2016/087488 A1 | 6/2016 |
| WO | WO 2016/087490 A1 | 6/2016 |
| WO | WO 2016/087651 A1 | 6/2016 |
| WO | WO 2016/089928 A1 | 6/2016 |
| WO | WO 2016/091776 A1 | 6/2016 |
| WO | WO 2016/094273 A1 | 6/2016 |
| WO | WO 2016/094309 A1 | 6/2016 |
| WO | WO 2016/094904 A1 | 6/2016 |
| WO | WO 2016/096610 A1 | 6/2016 |
| WO | WO 2016/097013 A1 | 6/2016 |
| WO | WO 2016/100619 A2 | 6/2016 |
| WO | WO 2016/100882 A1 | 6/2016 |
| WO | WO 2016/100975 A1 | 6/2016 |
| WO | WO 2016/102179 A1 | 6/2016 |
| WO | WO 2016/102427 A1 | 6/2016 |
| WO | WO 2016/102493 A1 | 6/2016 |
| WO | WO 2016/102672 A2 | 6/2016 |
| WO | WO 2016/112245 A1 | 7/2016 |
| WO | WO 2016/117666 A1 | 7/2016 |
| WO | WO 2016/120196 A1 | 8/2016 |
| WO | WO 2016/126552 A1 | 8/2016 |
| WO | WO 2016/130839 A1 | 8/2016 |
| WO | WO 2016/133910 A1 | 8/2016 |
| WO | WO 2016/142312 A1 | 9/2016 |
| WO | WO 2016/142313 A1 | 9/2016 |
| WO | WO 2016/145150 A2 | 9/2016 |
| WO | WO 2016/146542 A1 | 9/2016 |
| WO | WO 2016/149366 A1 | 9/2016 |
| WO | WO 2016/153839 A1 | 9/2016 |
| WO | WO 2016/153948 A1 | 9/2016 |
| WO | WO 2016/154068 A1 | 9/2016 |
| WO | WO 2016/154544 A1 | 9/2016 |
| WO | WO 2016/166600 A1 | 10/2016 |
| WO | WO 2016/168721 A1 | 10/2016 |
| WO | WO 2016/174183 A1 | 11/2016 |
| WO | WO 2016/176664 A1 | 11/2016 |
| WO | WO 2016/177658 A1 | 11/2016 |
| WO | WO 2016/177833 A1 | 11/2016 |
| WO | WO 2016/184962 A1 | 11/2016 |
| WO | WO 2016/184963 A1 | 11/2016 |
| WO | WO 2016/184973 A1 | 11/2016 |
| WO | WO 2016/187122 A1 | 11/2016 |
| WO | WO 2016/187508 A2 | 11/2016 |
| WO | WO 2016/189042 A1 | 12/2016 |
| WO | WO 2016/191363 A1 | 12/2016 |
| WO | WO 2016/196471 A1 | 12/2016 |
| WO | WO 2016/198322 A1 | 12/2016 |
| WO | WO-2016201370 A1 | 12/2016 |
| WO | WO 2016/202756 A1 | 12/2016 |
| WO | WO 2016/202758 A1 | 12/2016 |
| WO | WO 2016/205551 A2 | 12/2016 |
| WO | WO 2016/205566 A1 | 12/2016 |
| WO | WO 2016/205695 A1 | 12/2016 |
| WO | WO 2016/207089 A1 | 12/2016 |
| WO | WO 2016/207090 A2 | 12/2016 |
| WO | WO 2016/207094 A1 | 12/2016 |
| WO | WO 2016/207098 A1 | 12/2016 |
| WO | WO 2016/210247 A1 | 12/2016 |
| WO | WO 2016/210289 A1 | 12/2016 |
| WO | WO 2017/002064 A1 | 1/2017 |
| WO | WO 2017/003908 A1 | 1/2017 |
| WO | WO 2017/004092 A1 | 1/2017 |
| WO | WO 2017/004266 A1 | 1/2017 |
| WO | WO 2017/004267 A1 | 1/2017 |
| WO | WO 2017/005674 A1 | 1/2017 |
| WO | WO 2017/005711 A1 | 1/2017 |
| WO | WO 2017/008046 A1 | 1/2017 |
| WO | WO 2017/009325 A1 | 1/2017 |
| WO | WO 2017/012967 A1 | 1/2017 |

(56) References Cited

FOREIGN PATENT DOCUMENTS

| | | |
|---|---|---|
| WO | WO 2017/013436 A1 | 1/2017 |
| WO | WO 2017/017253 A1 | 2/2017 |
| WO | WO 2017/018476 A1 | 2/2017 |
| WO | WO 2017/019767 A1 | 2/2017 |
| WO | WO 2017/019875 A1 | 2/2017 |
| WO | WO 2017/019894 A1 | 2/2017 |
| WO | WO 2017/019896 A1 | 2/2017 |
| WO | WO 2017/019897 A1 | 2/2017 |
| WO | WO 2017/021348 A1 | 2/2017 |
| WO | WO 2017/021857 A1 | 2/2017 |
| WO | WO 2017/023994 A1 | 2/2017 |
| WO | WO 2017/025493 A1 | 2/2017 |
| WO | WO 2017/027379 A1 | 2/2017 |
| WO | WO 2017/027760 A1 | 2/2017 |
| WO | WO 2017/029514 A1 | 2/2017 |
| WO | WO 2017/031041 A1 | 2/2017 |
| WO | WO 2017/034234 A1 | 3/2017 |
| WO | WO 2017/035230 A1 | 3/2017 |
| WO | WO 2017/035453 A1 | 3/2017 |
| WO | WO 2017/037022 A1 | 3/2017 |
| WO | WO 2017/040953 A1 | 3/2017 |
| WO | WO 2017/041043 A1 | 3/2017 |
| WO | WO 2017/045750 A1 | 3/2017 |
| WO | WO 2017/045751 A1 | 3/2017 |
| WO | WO 2017/046142 A1 | 3/2017 |
| WO | WO 2017/049305 A1 | 3/2017 |
| WO | WO 2017/050849 A1 | 3/2017 |
| WO | WO 2017/053823 A1 | 3/2017 |
| WO | WO 2017/054739 A1 | 4/2017 |
| WO | WO 2017/055313 A1 | 4/2017 |
| WO | WO 2017/055316 A1 | 4/2017 |
| WO | WO 2017/055633 A1 | 4/2017 |
| WO | WO 2017/059224 A2 | 4/2017 |
| WO | WO 2017/059252 A1 | 4/2017 |
| WO | WO 2017/060322 A2 | 4/2017 |
| WO | WO 2017/063959 A1 | 4/2017 |
| WO | WO 2017/063966 A1 | 4/2017 |
| WO | WO 2017/066530 A1 | 4/2017 |
| WO | WO 2017/067530 A2 | 4/2017 |
| WO | WO 2017/069288 A1 | 4/2017 |
| WO | WO 2017/069289 A1 | 4/2017 |
| WO | WO 2017/070198 A1 | 4/2017 |
| WO | WO 2017/075451 A1 | 5/2017 |
| WO | WO 2017/075465 A1 | 5/2017 |
| WO | WO 2017/075478 A2 | 5/2017 |
| WO | WO 2017/079746 A2 | 5/2017 |
| WO | WO 2017/080920 A1 | 5/2017 |
| WO | WO 2017/083354 A1 | 5/2017 |
| WO | WO 2017/086367 A1 | 5/2017 |
| WO | WO 2017/091777 A1 | 6/2017 |
| WO | WO 2017/091865 A1 | 6/2017 |
| WO | WO 2017/093272 A1 | 6/2017 |
| WO | WO 2017/093447 A1 | 6/2017 |
| WO | WO 2017/093448 A1 | 6/2017 |
| WO | WO 2017/096246 A1 | 6/2017 |
| WO | WO 2017/097986 A1 | 6/2017 |
| WO | WO 2017/102091 A1 | 6/2017 |
| WO | WO 2017/102649 A1 | 6/2017 |
| WO | WO 2017/106129 A1 | 6/2017 |
| WO | WO 2017/106656 A1 | 6/2017 |
| WO | WO 2017/112838 A1 | 6/2017 |
| WO | WO 2017/112954 A1 | 6/2017 |
| WO | WO 2017/112955 A1 | 6/2017 |
| WO | WO 2017/112956 A1 | 6/2017 |
| WO | WO 2017/117196 A1 | 7/2017 |
| WO | WO 2017/117418 A1 | 7/2017 |
| WO | WO 2017/118864 A1 | 7/2017 |
| WO | WO 2017/118865 A1 | 7/2017 |
| WO | WO 2017/120204 A2 | 7/2017 |
| WO | WO 2017/121684 A1 | 7/2017 |
| WO | WO 2017/123568 A2 | 7/2017 |
| WO | WO 2017/125423 A1 | 7/2017 |
| WO | WO 2017/127414 A1 | 7/2017 |
| WO | WO 2017/129716 A1 | 8/2017 |
| WO | WO 2017/132536 A1 | 8/2017 |
| WO | WO 2017/132541 A1 | 8/2017 |
| WO | WO 2017/134000 A1 | 8/2017 |
| WO | WO 2017/134030 A1 | 8/2017 |
| WO | WO 2017/134116 A1 | 8/2017 |
| WO | WO 2017/134231 A1 | 8/2017 |
| WO | WO 2017/136342 A1 | 8/2017 |
| WO | WO 2017/139231 A1 | 8/2017 |
| WO | WO 2017/143237 A1 | 8/2017 |
| WO | WO 2017/144543 A1 | 8/2017 |
| WO | WO 2017/145162 A1 | 8/2017 |
| WO | WO 2017/148995 A1 | 9/2017 |
| WO | WO 2017/152062 A1 | 9/2017 |
| WO | WO 2017/153220 A1 | 9/2017 |
| WO | WO 2017/156147 A1 | 9/2017 |
| WO | WO 2017/157418 A1 | 9/2017 |
| WO | WO 2017/157792 A1 | 9/2017 |
| WO | WO 2017/157991 A1 | 9/2017 |
| WO | WO 2017/157992 A1 | 9/2017 |
| WO | WO 2017/160717 A2 | 9/2017 |
| WO | WO 2017/160761 A2 | 9/2017 |
| WO | WO 2017/161331 A1 | 9/2017 |
| WO | WO-2017197140 A1 | 11/2017 |
| WO | WO-2017197153 A1 | 11/2017 |
| WO | WO-2018016563 A1 | 1/2018 |
| WO | WO 2018/133716 A1 | 7/2018 |
| WO | WO-2019032769 A1 | 2/2019 |

OTHER PUBLICATIONS

Cheson et al.: Revised Response Criteria for Malignant Lymphoma. Journal of Clinical Oncology. 25(5):579-586 (2007).
Chothia et al.: Canonical Structures for the Hypervariable Regions of Immunoglobulins. J. Mod. Biol. 196:901-917 (1987).
Clackson et al.: Making Antibody Fragments Using Phage Display Libraries, Nature, 1991, 352:624-8.
Cole et al.: The EBV-hybridoma technique and its application to human lung cancer, In: Monoclonal Antibodies and Cancer Therapy, vol. 27, UCLA Symposia on Molecular and Cellular Biology, New Series, Eds. R.A. Reisfeld and S.Sell, pp. 77-96, Alan R. Liss, Inc. N.Y., 1985.
Cortes et al.: Eribulin monotherapy versus treatment of physician's choice in patients with metastatic breast cancer (EMBRACE): a phase 3 open-label randomised study. Lancet 377:914-923 (2011).
Eckschlager et al.: Histone deacetylase inhibitors as anticancer drugs. International Journal of Molecular Sciences 18(7):1414; doi:10.3390/ijms18071414 [1-25] (2017).
Eisenhauer et al.: New response evaluation criteria in solid tumours: revised RECIST guideline (version 1.1). Euro J Cancer 45:228-247 (2009).
Fellouse et al.: Synthetic antibodies from a four-amino-acid code: a dominant role for tyrosine in antigen recognition. Proc Natl Acad Sci USA. Aug. 24, 2004;101(34):12467-72. Epub Aug. 11, 2004.
Fishwild et al.: High-avidity human IgG kappa monoclonal antibodies from a novel strain of minilocus transgenic mice. Nat Biotechnol. Jul. 1996;14(7):845-51. Nat Biotechnol. Jul. 1996;14(7):845-51.
Garlapow. New therapy blocks breast cancer cells from entering and hiding in bone marrow to form latent metastases. Published online at Oncology Nurse Advisor https://www.oncologynurseadvisor.com/home/cancer-types/breast-cancer/new-therapy-blocks-breast-cancer-cells-from-entering-and-hiding-in-bone-marrow-to-form-latent-metastases/ (Jun. 16, 2016).
Gu et al.: Activation of p53 sequence-specific DNA binding by acetylation of the p53 C-terminal domain. Cell. Aug. 22, 1997;90(4):595-606.
Hammerling et al.: in: Monoclonal Antibodies and T -Cell Hybridomas, pp. 563-681, Elsevier, N.Y., 1981.
Harlow and Lane. Antibodies: A Laboratory Manual, Cold Spring Harbor Laboratory, 1988.
Harris. Production of humanized monoclonal antibodies for in vivo imaging and therapy. Biochem Soc Trans. Nov. 1995;23(4):1035-8.
Hongo et al.: Development and characterization of murine monoclonal antibodies to the latency-associated peptide of transforming growth factor beta 1. Hybridoma. Jun. 1995;14(3):253-60.

(56) References Cited

OTHER PUBLICATIONS

Hoogenboom et al.: By-passing immunisation. Human antibodies from synthetic repertoires of germline VH gene segments rearranged in vitro. J Mol Biol. Sep. 20, 1992;227(2):381-8.

Hurle et al.: Protein engineering techniques for antibody humanization. Curr Opin Biotechnol. Aug. 1994;5(4):428-33.

Huston et al.: Antigen Recognition and Targeted Delivery by the Single-Chain Fv. Cell Biophysics. 22:189-224 (1993).

Indian Patent Application No. IN201847045896 Examination Report dated Jul. 8, 2020.

Jacobson et al.: Modifying chromatin and concepts of cancer. Current Opinion in Genetics and Development 9(2):175-184 (1999).

Jakobovits et al.: Analysis of homozygous mutant chimeric mice: deletion of the immunoglobulin heavy-chain joining region blocks B-cell development and antibody production. PNAS 90:2551-2555 (1993).

Jakobovits et al.: Germ-line transmission and expression of a human-derived yeast artificial chromosome. Nature. Mar. 18, 1993;362(6417):255-258.

Johnstone. Histone-deacetylase inhibitors: novel drugs for the treatment of cancer. Nature Reviews: Drug Discovery 1(4):287-299 (2002).

Jones et al.: Replacing the complementarity-determining regions in a human antibody with those from a mouse. Nature, 321.6069 (1986): 522-5.

Juan et al.: Histone deacetylases specifically down-regulate p53-dependent gene activation. Journal of Biological Chemistry 275(27):20436-20443 (2000).

Kabat et al.: Unusual distributions of amino acids in complementarity-determining (hypervariable) segments of heavy and light chains of immunoglobulins and their possible roles in specificity of antibody-combining sites. J. Biol. Chem. 252(19):6609-6616 (1977).

Kohler et al.: Continuous cultures of fused cells secreting antibody of predefined specificity. Nature. Aug. 7, 1975;256(5517):495-7.

Korzus et al.: Transcription factor-specific requirements for coactivators and their acetyltransferase functions. Science 279(5351):703-707 (1998).

KOUZARIDES. Histone acetylases and deacetylases in cell proliferation. Curr Opin Genet Dev. Feb. 1999;9(1):40-8.

Kuo et al.: Roles of histone acetyltransferases and deacetylases in gene regulation. Bioessays 20(8):615-626 (1998).

Lee et al.: Bivalent antibody phage display mimics natural immunoglobulin. J Immunol Methods. Jan. 2004;284(1-2):119-132.

Lee et al.: High-affinity human antibodies from phage-displayed synthetic Fab libraries with a single framework scaffold. J Mol Biol. Jul. 23, 2004;340(5):1073-93.

Levitt. Clinical trials in leukemia focus on new treatment approaches: a phase I study of an oral histone deacetylase inhibitor, MS-275, in refractory solid tumors and lymphomas. University of Maryland Medical News Press Release, originally sited at http://www.umm.edu/news/releases/karp.html [retrieved from: https://www.newswise.com/articles/clinical-trials-in-leukemia-focus-on-new-treatment-approaches] (2001).

Li et al.: Design, synthesis and antiproliferative activities of novel benzamides derivatives as HDAC inhibitors. European Journal of Medicinal Chemistry 100:270-276 (2015).

Li et al.: Human antibodies for immunotherapy development generated via a human B cell hybridoma technology. Proc Natl Acad Sci USA. Mar. 7, 2006;103(10):3557-62. Epub Feb. 27, 2006.

Lin et al.: Transcriptional regulation in acute promyelocytic leukemia. Oncogene 20(49):7204-7215 (2001).

Lonberg et al.: Antigen-specific human antibodies from mice comprising four distinct genetic modifications. Nature. Apr. 28, 1994;368(6474):856-9.

MacCallum et al.: Antibody-antigen interactions: contact analysis and binding site topography. J Mol Biol. 262(5):732-745 (1996).

Marks et al.: By-passing immunization: building high affinity human antibodies by chain shuffling. Biotechnology (N Y). Jul. 1992;10(7):779-83.

Marks et al.: By-Passing Immunization Human Antibodies from V-gene Libraries Displayed on Phage. J. Mol. Biol., 222 (1991): 581-597.

Marks et al.: Histone deacetylase inhibitors as new cancer drugs. Current Opinion in Oncology 13(6):477-483 (2001).

McKenna et al.: Combinatorial control of gene expression by nuclear receptors and coregulators. Cell 108(4):465-474 (2002).

Morea et al.: Antibody modeling: implications for engineering and design. Methods 20(3):267-279 (2000).

Morrison et al.: Chimeric human antibody molecules: Mouse antigen-binding domains with human constant region domains. Proc. Natl. Acad. Sci. 81:6851-6855 (1984).

Morrison. Immunology. Success in specification. Nature. Apr. 28, 1994;368(6474):812-3.

NEUBERGER. Generating high-avidity human Mabs in mice. Nat Biotechnol. Jul. 1996;14(7):826.

Nudelman et al.: Novel mutual prodrug of retinoic and butyric acids with enhanced anticancer activity. Journal of Medicinal Chemistry 43(15):2962-2966 (2000).

Pazin et al.: What's up and down with histone deacetylation and transcription? Cell 89(3):325-328 (1997).

PCT/IB2004/000401 International Search Report and Written Opinion dated Apr. 21, 2005.

PCT/US2017/032200 International Search Report and Written Opinion dated Sep. 26, 2017.

PCT/US2017/032218 International Search Report and Written Opinion dated Sep. 22, 2017.

PCT/US2018/045909 International Search Report and Written Opinion dated Oct. 16, 2018.

PCT/US2020/036549 International Search Report and Written Opinion dated Sep. 29, 2020.

Phickthun and Skerra. Meth. Enzyomol. 178:497-515 (1989).

Phiel et al.: Histone deacetylase is a direct target of valproic acid, a potent anticonvulsant, mood stabilizer, and teratogen. Journal of Biological Chemistry 276(39):36734-36741 (2001).

Presta. Antibody Engineering. Curr. Op. Struct. Biol. 1992; 2:593-596.

Riechmann et al.: Reshaping human antibodies for therapy. Nature, 332.6162:323-7 (1988).

Saito et al.: A synthetic inhibitor of histone deacetylase, MS-27-275, with marked in vivo antitumor activity against human tumors. Proc Natl Acad Sci U S A. Apr. 13, 1999;96(8):4592-7.

Schemes et al.: Histone deacetylase inhibitors that target tubulin. Cancer Letters 280(2):222-232 (2009).

Sidhu et al.: Phage-displayed antibody libraries of synthetic heavy chain complementarity determining regions. J Mol Biol. Apr. 23, 2004;338(2):299-310.

Steffan et al.: Histone deacetylase inhibitors arrest polyglutamine-dependent neurodegeneration in Dropsophila Nature, 413:739-743, 2001.

Thiel et al.: Structure-aided drug design's next generation. Nature Biotechnology 22(5):513-519 (2004).

U.S. Appl. No. 10/770,035 Office Action dated Oct. 26, 2006.
U.S. Appl. No. 11/776,477 Notice of Allowance dated Jan. 8, 2009.
U.S. Appl. No. 11/776,477 Restriction Requirement dated Sep. 3, 2008.
U.S. Appl. No. 15/592,929 Office Action dated Nov. 28, 2018.
U.S. Appl. No. 15/592,988 Office Action dated Nov. 28, 2018.
U.S. Appl. No. 15/676,905 Office Action dated Apr. 2, 2018.
U.S. Appl. No. 15/676,905 Office Action dated Dec. 11, 2018.
U.S. Appl. No. 15/676,905 Office Action dated Mar. 18, 2019.
U.S. Appl. No. 15/676,905 Office Action dated Oct. 2, 2019.
U.S. Appl. No. 16/103,865 Office Action dated Dec. 27, 2018.
U.S. Appl. No. 16/103,865 Office Action dated Oct. 5, 2018.

Van Dijk et al.: Human antibodies as next generation therapeutics. Curr Opin Chem Biol. Aug. 2001;5(4):368-74.

Vaswani et al.: Humanized antibodies as potential therapeutic drugs. Ann Allergy Asthma Immunol. Aug. 1998;81(2):105-15; quiz 115-6, 119.

Warrell et al.: Therapeutic targeting of transcription in acute promyelocytic leukemia by use of an inhibitor of histone deacetylase. Journal of the National Cancer Institute 90(21):1621-1625 (1998).

(56) References Cited

OTHER PUBLICATIONS

West and Johnstone. New and emerging HDAC inhibitors for cancer treatment. The Journal of clinical investigation vol. 124,1 (2014): 30-9. doi:10.1172/JCI69738.
West. Solid State Chemistry and its Applications. Wiley, New York. pp. 358 & 365 (1988).
Wolchok et al.: Guidelines for the evaluation of immune therapy activity in solid tumors: immune-related response criteria. Clin Cancer Res 15(23):7412-7420 (2009).
Zhong et al.: Phosphorylation of NF-kappa B p65 by PKA stimulates transcriptional activity by promoting a novel bivalent interaction with the coactivator CBP/p300. Molecular Cell 1(5):661-671 (1998).
Apuri et al., "An overview of investigational Histone deacetylase inhibitors (HDACis) for the treatment of non-Hodgkin's lymphoma," Expert Opin. Investig. Drugs, DOI: 10.1517/13543784. 2016.1164140, 11 pages (2016).
Brahmer et al., "Immune checkpoint inhibitors: making immunotherapy a reality for the treatment of lung cancer," Cancer Immunol. Res., 1(2):85-91 (2013).
Carbognin et al., "Differential activity of nivolumab, pembrolizumab and MPDL3280A according to the tumor expression of programmed death-ligand-1 (PD-L1): sensitivity analysis of trials in melanoma, lung and genitourinary cancers," PLoS One, 10(6):e0130142 (2015).
Gettinger et al., Nivolumab monotherapy for first-line treatment of advanced non-small-cell lung cancer, J. Clin. Oncol., 34(25):2980-2987 (2016).
Guerriero et al., "Class IIa HDAC inhibition reduces breast tumours and metastases through anti-tumour macrophages," Nature, 543:428-432 (2017).
Hellmann et al., "Nivolumab plus ipilimumab as first-line treatment for advanced non-small-cell lung cancer (CheckMate 012): results of an open-label, phase 1, multicohort study," Lancet Oncol., 18(1):31-41 (2017).
Kurose et al., "Phase Ia study of FoxP3+ CD4 treg depletion by infusion of a humanized anti-CCR4 antibody, KW-0761, in cancer patients," Clin. Cancer Res., 21:4327-4336 (2015).
Larkin et al., "Overall survival in patients with advanced melanoma who received nivolumab versus investigator's choice chemotherapy in CheckMate 037: a randomized, controlled, open-label phase III trial," J. Clin. Oncol., 36:383-390 (2017).
Leidner, "Preliminary efficacy from a phase 1/2 study of the natural killer cell-targeted antibody, lirilumab in combination with nivolumab in squamous cell carcinoma of the head and neck," SITC 2016, National Harbor, MD, Nov. 9-13, 2016, Poster No. 456.
Lipson, "Initial experience administering BMS-986016, a monoclonal antibody that targets lymphocyte activation gene (LAG)-3, alone and in combination with nivolumab to patients with hematologic and solid malignancies," SITC 2016, National Harbor, MD, Nov. 9-13, 2016, Poster No. 238.
Marrone, "A randomized phase II study of epigenetic therapy with azacitidine and entinostat with concurrent nivolumab versus nivolumab alone in recurrent metastatic non-small cell lung cancer," SITC 2016, National Harbor, MD, Nov. 9-13, 2016, Poster No. 151.
Massarelli, "Clinical safety and efficacy assessment of the CD137 agonist urelumab alone and in combination with nivolumab in patients with hematologic and solid tumor malignancies," SITC 2016, National Harbor, MD, Nov. 9-13, 2016, Poster No. 239.
Motzer et al., "Nivolumab for metastatic renal cell carcinoma: results of a randomized phase II trial," J. Clin. Oncol., 33(13):1430-1437 (2014).
Oki et al., "Immune regulatory effects of panobinostat in patients with Hodgkin lymphoma through modulation of serum cytokine levels and T-cell PD1 expression," Blood Cancer J., 4:e236 (2014).
OPDIVO (nivolumab) Package Insert, Revised Dec. 2017.
Overman et al., "Nivolumab in patients with metastatic DNA mismatch repair-deficient or microsatellite instability-high colorectal cancer (CheckMate 142): an open-label, multicentre, phase 2 study," Lancet Oncol., 18:1182-1191 (2017).

Park et al., "Epigenetic modulation with histone deacetylase inhibitors in combination with immunotherapy," Epigenomics, 7(4):641-652 (2015).
Rhyasen et al., "Strategies to enhance patient responses to checkpoint inhibitors," Oncology Discovery, Aug. 8, 2015. Retrieved from the internet: http://oncologydiscovery.com/2015/08/08/strategies-to-enhance-patient [retrieved on Sep. 8, 2015].
Shtivelman et al., "Molecular pathways and therapeutic targets in lung cancer," Oncotarget, 5(6):1392-1433 (2014).
Topalian et al., "Survival, durable tumor remission, and long-term safety in patients with advanced melanoma receiving nivolumab," J. Clin. Oncol., 32:1020-1030 (2014).
Topper et al., "Epienetic therapy ties MYC depletion to reversing immune evasion and treating lung cancer," Cell, 171:1284-1300 (2017).
Wang et al., "In vitro characterization of the anti-PD-1 antibody nivolumab, BMS-936558, and in vivo toxicology in non-human primates," Cancer Immunol. Res., 2(9):846-856 (2014),.
Weber et al., "Adjuvant nivolumab versus ipilimumab in resected stage III or IV melanoma," N. Engl. J. Med., 377:1824-1835 (2017).
Woods et al., "Abstract 4090: Inhibition of class I histone deacetylases promotes robust and durable enhancement of PDL1 expression in melanoma: Rationale for combination therapy," Cancer Res., 74:4090 (2014).
Woods et al., "HDAC inhibition upregulates PD-1 ligands in melanoma and augments immunotherapy with PD-1 blockade," Cancer Immunol Res., CIR-15-0077 (2015).
Zardavas et al., "Emerging targeted agents in metastatic breast cancer," Nat. Rev. Clin. Oncol., 10:191-210(2013).
Zheng et al., "HDAC inhibitors enhance T-cell chemokine expression and augment response to PD-1 immunotherapy in lung adenocarcinoma," Clin. Cancer Res., 22(16):4119-4132 (2016).
Zimmer et al., "Ipilimumab alone or in combination with nivolumab after progression on anti-PD-1 therapy in advanced melanoma," Eur. J. Cancer, 75:47-55 (2017).
Brahmer et al. "Safety and Activity of Anti-PD-L1 Antibody in Patients with Advanced Cancer," N. Engl. J. Med. 366(26):2455-2465 (2012).
Curran et al. "PD-1 and CTLA-4 combination blockade expands infiltrating T cells and reduces regulatory T and myeloid cells within B16 melanoma tumors," PNAS 107(9):4275-4280 (2010).
Hamid et al. "Safety and Tumor Responses with Lambrolizumab (Anti-PD-1) in Melanoma," N. Engl. J. Med. 369(2):134-144 (2013).
Topalian et al. "Safety, Activity, and Immune Correlates of Anti-PD-1 Antibody in Cancer," N. Engl. J. Med. 366(26):2443-2454 (2012).
Topalian et al., "Targeting the PD-1/B7-H!(PD-L1) pathway to activate anti-tumor immunity," Curr. Opin. Immunol. 24(2):207-212 (2012).
Weber et al. "Safety, Efficacy, and Biomarkers of Nivolumab With Vaccine in Ipilimumab-Refractory or-Naïve Melanoma," J. Clin. Oncol. 31(34):4311-4318 (2013).
Wolchok et al. "Nivolumab plus Ipilimumab in Advanced Melanoma," N. Engl. J. Med. 369(2):122-133 (2013).
Woo et al., "Immune Inhibitory Molecules LAG-3 and PD-1 Synergistically Regulate T-cell Function to Promote Tumoral Immune Escape," Cancer Res. 72(4):917-927 (2012).
Bergman et al., "Selective Histone Deacetylase 6 Inhibitors Bearing Substituted Urea Linkers Inhibit Melanoma Cell Growth," J. Med. Chem. 55(22):9891-9899 (2012).
Woods et al., "The Anti-melanoma Activity of the Histone Deacetylase Inhibitor Panobinostat (LBH589) Is Mediated by Direct Tumor Cytotoxicity and Increased Tumor Immunogenicity," Melanoma Res. 23(5):341-348 (2013).
Ning et al., "Chidamide (CS055/HBI-8000): a new histone deacetylase inhibitor of the benzamide class with antitumor activity and the ability to enhance inmune cell-mediated tumor cell cytotoxicity," Cancer Chemother. Pharmacol. 69:901-909 (2012), published online Nov. 12, 2011.
Bissonnette et al., "Abstract B108: The HDAC inhibitor HBI-8000 enhances immunotherapy with either PD-1 or PD-L1 blockade in the MC38 model of colon cancer," Proceedings of the Second CRI-CIMT-EATI-AACR International Cancer Immunotherapy Con-

(56) References Cited

OTHER PUBLICATIONS ference: Translating Science into Survival, Sep. 25-28, 2016, vol. 4, No. 11 Suppl, Sep. 25, 2016, retrieved from the internet: https://cancerimmunolres.aacrjournals.org/content/4/11_Supplement/B108 [retrieved on Oct. 31, 2019].

Woods et al., "Abstract 257: Class I HDAC inhibition upregulates PD-1 ligands in melanoma and increases the efficacy of PD-1 blockade," Proceedings: AACR 106th Annual Meeting, Apr. 18, 2015, pp. 1-2, retrieved from the internet: https://cancerres.aacrjournals.org/content/75/15_Supplement/257 [retrieved-on Nov. 28, 2019],.

Anonymous, "Study of HBI-8000 With Nivolumab in Melanoma, Renal Cell Carcinoma and NonSmall Cell Lung Cancer," NCT02718066, ClinicalTrials.gov, Mar. 24, 2016, pp. 1-9, retrieved from the internet: https://clinicaltrials.gov/ct2/show/record/NCT02718066 [retrieved on Nov. 28, 2019].

Arghya et al., "Combination of Anti-PD-L1 Antibody with IMiD (R) Tnmunomodulatory Drugs, HDAC Inhibitor ACY-1215, Bortezomib, or Toll-like Receptor 9 Agonist Enhances Anti-Tumor Inmunity and Cytotoxicity in Multiple Myeloma," Database BIOSIS [Online] Biosciences Information Service, Philadelphia, Pa, US; Dec. 2015, Database accession No. PREV201600269088.

Australian Examination Report for AU2017263478, dated Apr. 15, 2021 (10 Pages).

Australian Examination Report for AU2017264857, dated May 4, 2021 (9 Pages).

Briere et al., "Abstract 4021: The class I HDAC inhibitor, mocetinostat, induces expression of PD-L1 and tumor antigen presentation machinery and modifies tumor immune cellular subsets providing a rationale for immune checkpoint inhibitor combinations," Cancer Research, Proceedings: AACR 107th Annual Meeting Apr. 2016.

Kabat, Elvin A. "The structural basis for antibody complementary." Advances in protein chemistry 32 (1978): 1-75.

Kim, KiBem, et al. "Eradication of metastatic mouse cancers resistant to immune checkpoint blockade by suppression of myeloid-derived cells." Proceedings of the National Academy of Sciences 111.32 (2014): 11774-11779.

Lipson et al., "Antagonists of PD-1 and PD-L1 in Cancer Treatment," Semin Oncol (2015); 42(4): 587-600.

Llopiz, Diana, et al. "Enhanced anti-tumor efficacy of checkpoint inhibitors in combination with the histone deacetylase inhibitor Belinostat in a murine hepatocellular carcinoma model." Cancer Immunology, Immunotherapy 68.3 (2019): 379-393.

Lonberg, Nils, and Dennis Huszar. "Human antibodies from transgenic mice." International reviews of immunology 13.1 (1995): 65-93.

Mcdermott, J., and Antonio Jimeno. "Pembrolizumab: PD-1 inhibition as a therapeutic strategy in cancer." Drugs of today (Barcelona, Spain: 1998) 51.1 (2015): 7-20.

Ortllion et al., "Abstract4906: The selective class I HDAC inhibitor entinostat enhances the antitumor effect of PD-1 inhibiton in a syngenic orthotopic murine model of renal cell carcinoma," Cancer Research, Proceedings: AACR 107th Annual Meeting Apr. 2016.

Yin, Z. H., et al. "Synthesis of chidamide, a new histone deacetylase (HDAC) inhibitor." Chin J New Drugs 13 (2004): 536-538.

Japanese Notice of Reasons for Refusal for Japanese Application 2006-502441, dated Mar. 9, 2010 (3 pages).

Pan, et al., "Discovery of an orally active subtype-selective HDAC inhibitor, chidamide, as an epigenetic modulator for cancer treatement," Med. Chem. Commun., No. 5, Sep. 1, 2014, pp. 1789-1796.

Wang, Jinni, et al., "Comparison of chemotherapy combined with chidamide versus chemotherapy in the frontline treatment for peripheral T-cell lymphoma," Frontiers in immunology, vol. 13, Feb. 2022, 9 pages.

Yang, Xin, et al., "Upregulation of CD22 by Chidamide promotes Car T cells functionality." Scientific reports, 11.1, 2021, 9 pages.

Gui, Lin, et al., "Chidamide combined with cyclophosphamide, doxorubicin, vincristine and prednisone in previously untreated patients with peripheral T-cell lymphoma," Chinese Journal of Cancer Research, 33.5, Oct. 12, 2021, pp. 616-626.

Zhang, Wei, et al., "The combination of chidamide with the CHOEP regimen in previously untreated patients with peripheral T-cell lymphoma: a prospective, multicenter, single arm, phase 1b/2 study," Cancer Biology & Medicine, vol. 18, No. 3, 2021, pp. 841-848.

Wang, Xing, et al., "The Synergistic Anti-Tumor Activity of EZH2 Inhibitor SHR2554 and HDAC Inhibitor Chidamide through ORC1 Reduction of DNA Replication Process in Diffuse Large B Cell Lymphoma," Cancers, 13.17, Aug. 24, 2021, 18 pages.

Feng, Panpan, et al., "Deacetylation of YAP1 Promotes the Resistance to Chemo-and Targeted Therapy in FLT3-ITD+ AML, Cells." Frontiers in Cell and Developmental Biology, vol. 10, May 17, 2022.

Feng, Xiuyan, et al., "LncRNA ENST869 targeting nestin transcriptional region to affect the pharmacological effects of chidamide in breast cancer cells," Frontiers in Oncology, vol. 12, Apr. 4, 2022, 12 pages.

Que, Yi, et al., "Frequent amplification of HDAC genes and efficacy of HDAC inhibitor chidamide and PD-1 blockade combination in soft tissue sarcoma," Journal for ImmunoTherapy of Cancer, 9.2, 2021, 14 pages.

He, Yanjuan, et al., "Chidamide, a subtype-selective histone deacetylase inhibitor, enhances Bortezomib effects in multiple myeloma therapy," Journal of Cancer, vol. 12(20), Aug. 27, 2021, pp. 6198-6208.

Jiang, Duanfeng, et al., "Chidamide-Induced Accumulation of Reactive Oxygen Species Increases Lenalidomide Sensitivity Against Multiple Myeloma Cells," OncoTargets and Therapy, 14, Jul. 6, 2021, pp. 4061-4075.

Meng, Yanchun, et al., "Phase II study of chidamide in combination with cisplatin in patients with metastatic triple-negative breast cancer," Annals of Palliative Medicine, Sep. 9, 2021, 10 pages.

Roussos Torres, Evanthia T., et al., "Phase I Study of Entinostat and Nivolumab with or without Ipilimumab in Advanced Solid Tumors (ETCTN-9844)," Clinical Cancer Research, 27.21, Jun. 16, 2021, pp. 5828-5837.

Yin, Jia, et al., "A Phase II Trial of the Double Epigenetic Priming Regimen Including Chidamide and Decitabine for Relapsed/Refractory Acute Myeloid Leukemia," Frontiers in Oncology, vol. 11, Sep. 3, 2021, 13 pages.

Xue, Kai, et al., "Chidamide triggers BTG1-mediated autophagy and reverses the chemotherapy resistance in the relapsed/refractory B-cell lymphoma," Cell death & disease, 12.10, Oct. 1, 2021, pp. 1-11.

Zhang, Hongwei, et al., "Chidamide induces apoptosis in DLBCL cells by suppressing the HDACs/STAT3/Bcl-2 pathway," Molecular Medicine Reports, 23:308, Feb. 11, 2021, pp. 1-9.

Zhao, Haijun, et al. "Chidamide and apatinib are therapeutically synergistic in acute myeloid leukemia stem and progenitor cells," Experimental Hematology & Oncology, 11:29, 2022, pp. 1-14.

Gong, Ke, et al., "CS055 (Chidamide/HBI-8000), a novel histone deacetylase inhibitor, induces G1 arrest, ROS-dependent apoptosis and differentiation in human leukaemia cells," Biochemical Journal, 443.3, 2012, pp. 735-746.

Shi, Yehui, et al., "Romidepsin (FK228) regulates the expression of the immune checkpoint ligand PD-L1 and suppresses cellular immune functions in colon cancer," Cancer Immunology, Immunotherapy, 70.1, Jul. 6, 2021, pp. 61-73.

Truong, Andrew S., et al. "Entinostat induces antitumor immune responses through immune editing of tumor neoantigens." Journal of Clinical Investigation, 131(16), Aug. 16, 2021, 13 pages.

\* cited by examiner

Fig. 1: Median Tumor Volume (Example 1, all groups)
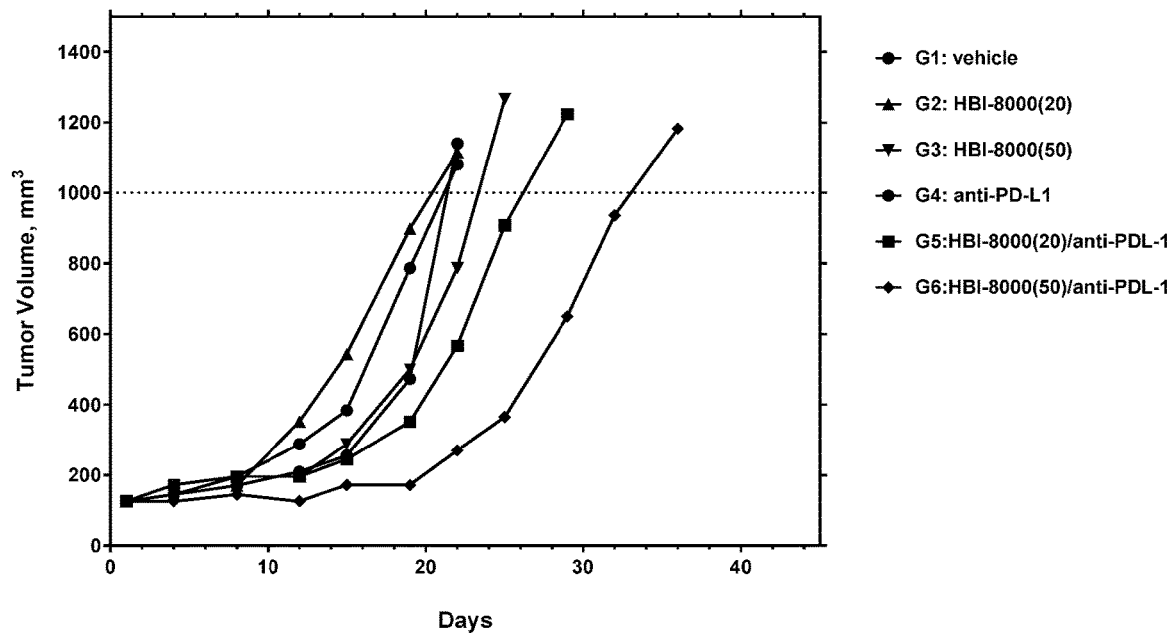

Fig. 2: Median Tumor Volume (Example 1, HBI-8000, 50 mpk groups)
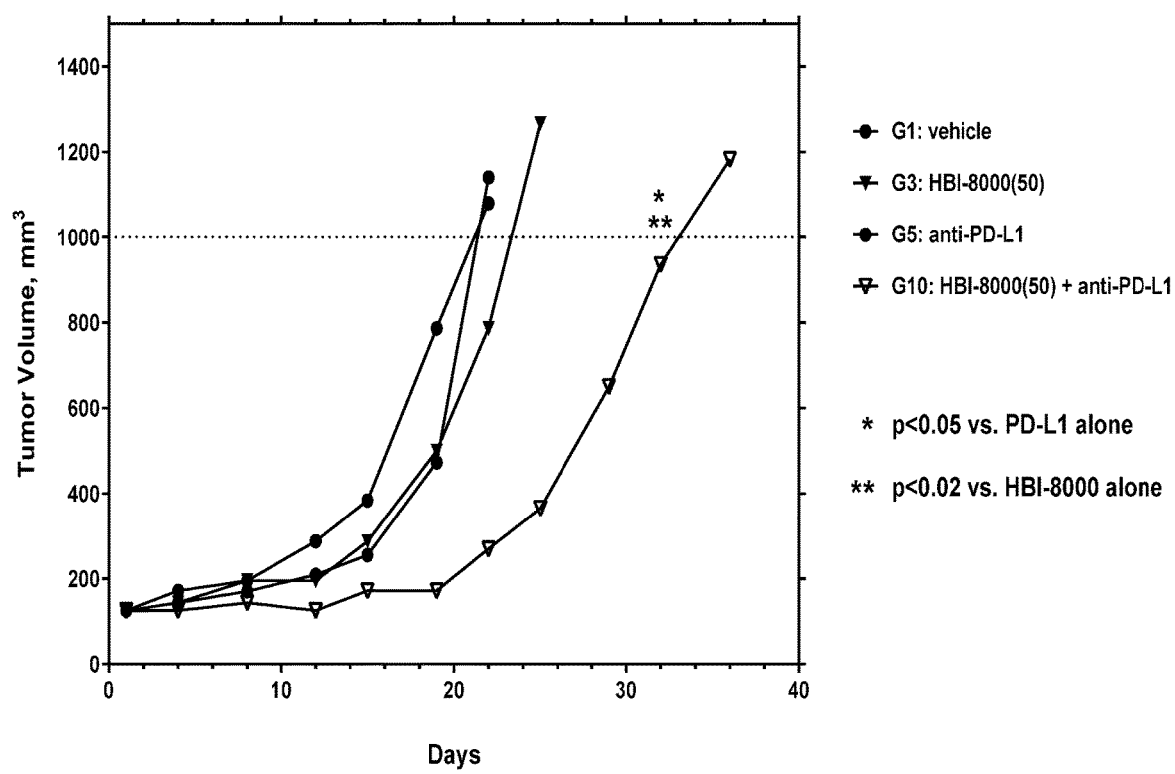

Fig. 3: Kaplan-Meier Survival Plot (Example 1, All groups)
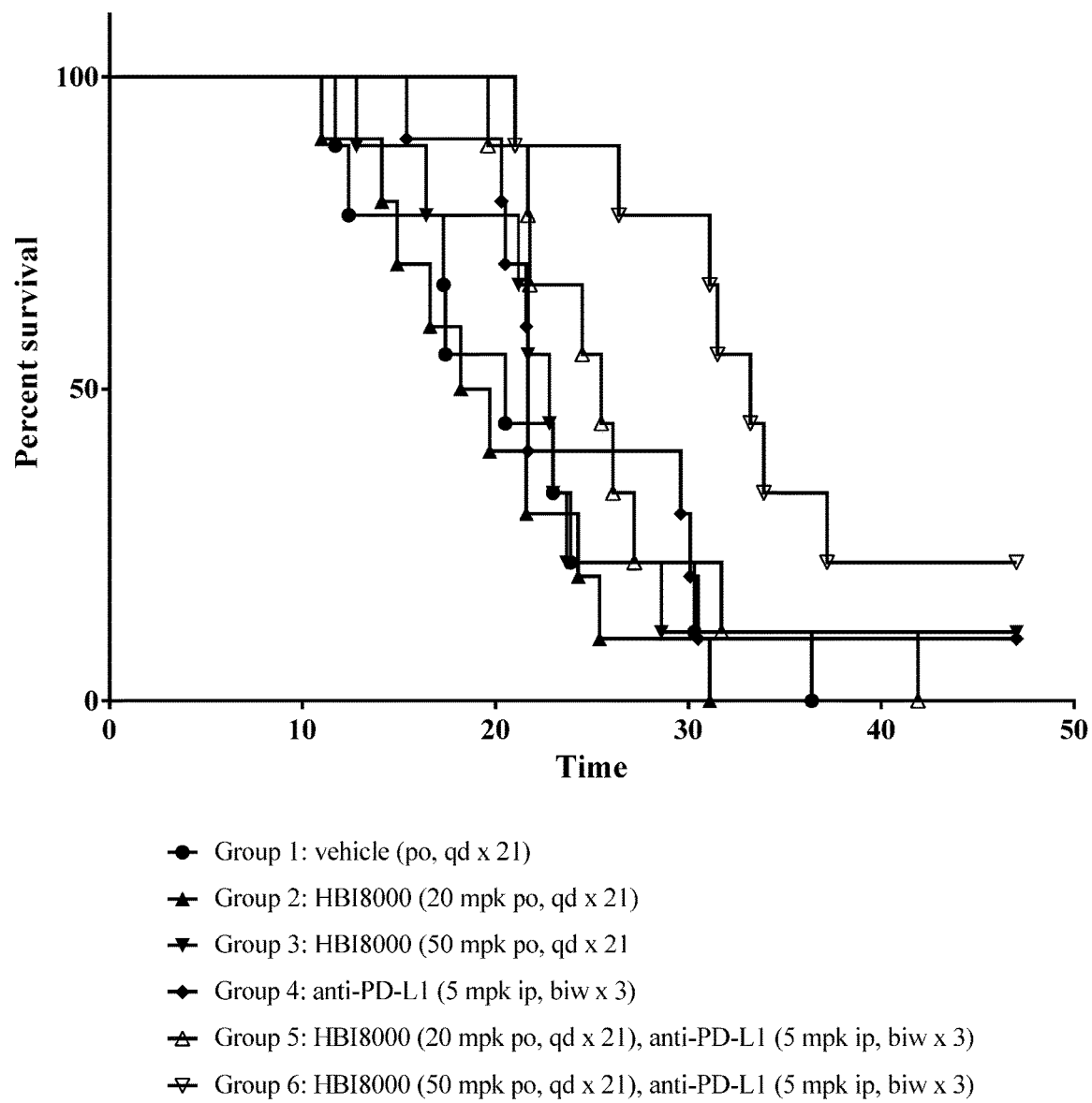
- Group 1: vehicle (po, qd x 21)
- Group 2: HBI8000 (20 mpk po, qd x 21)
- Group 3: HBI8000 (50 mpk po, qd x 21
- Group 4: anti-PD-L1 (5 mpk ip, biw x 3)
- Group 5: HBI8000 (20 mpk po, qd x 21), anti-PD-L1 (5 mpk ip, biw x 3)
- Group 6: HBI8000 (50 mpk po, qd x 21), anti-PD-L1 (5 mpk ip, biw x 3)

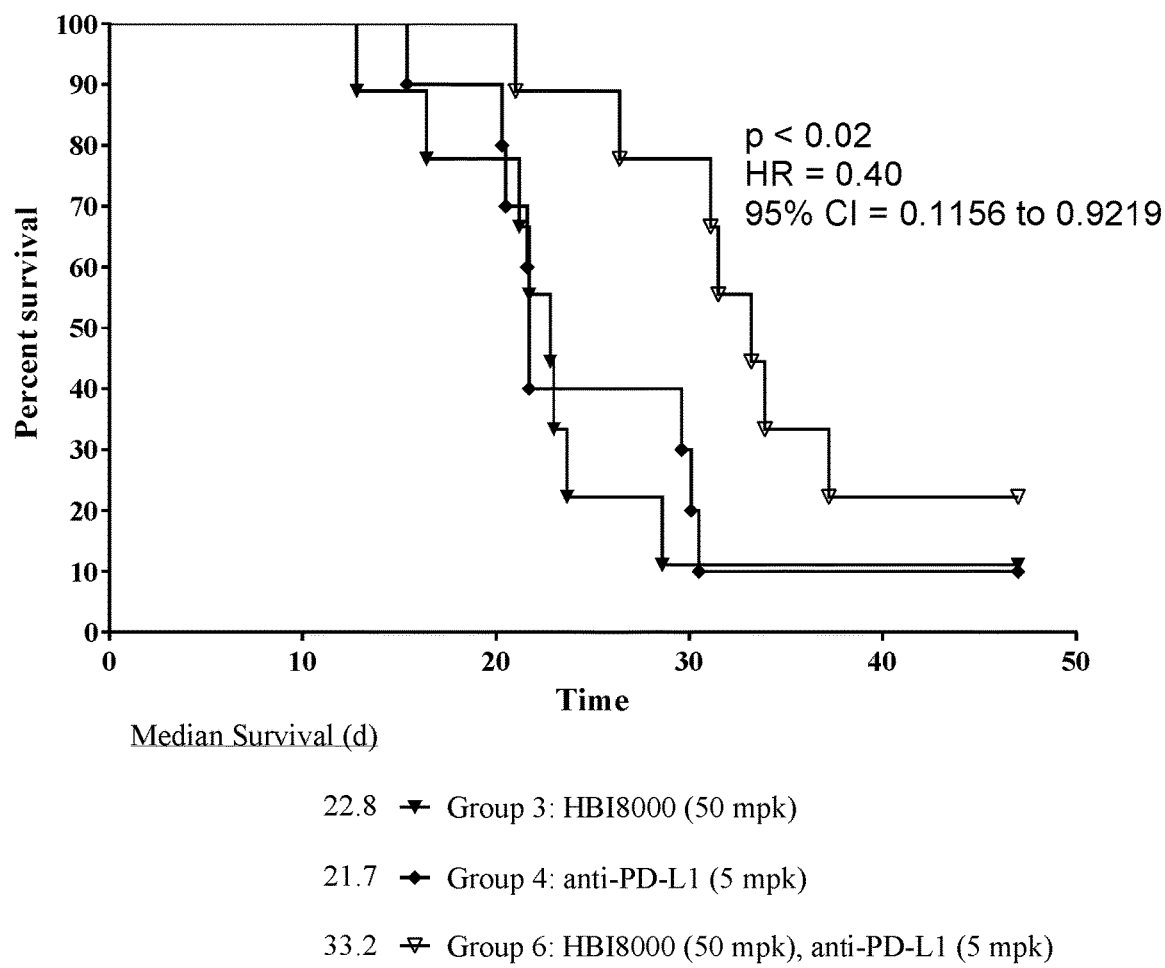
Fig. 4: Kaplan-Meier Survival Plot (Example 1, HBI-8000, 50 mpk groups)

Fig. 5: Median Tumor Volume Measurements for Example 2
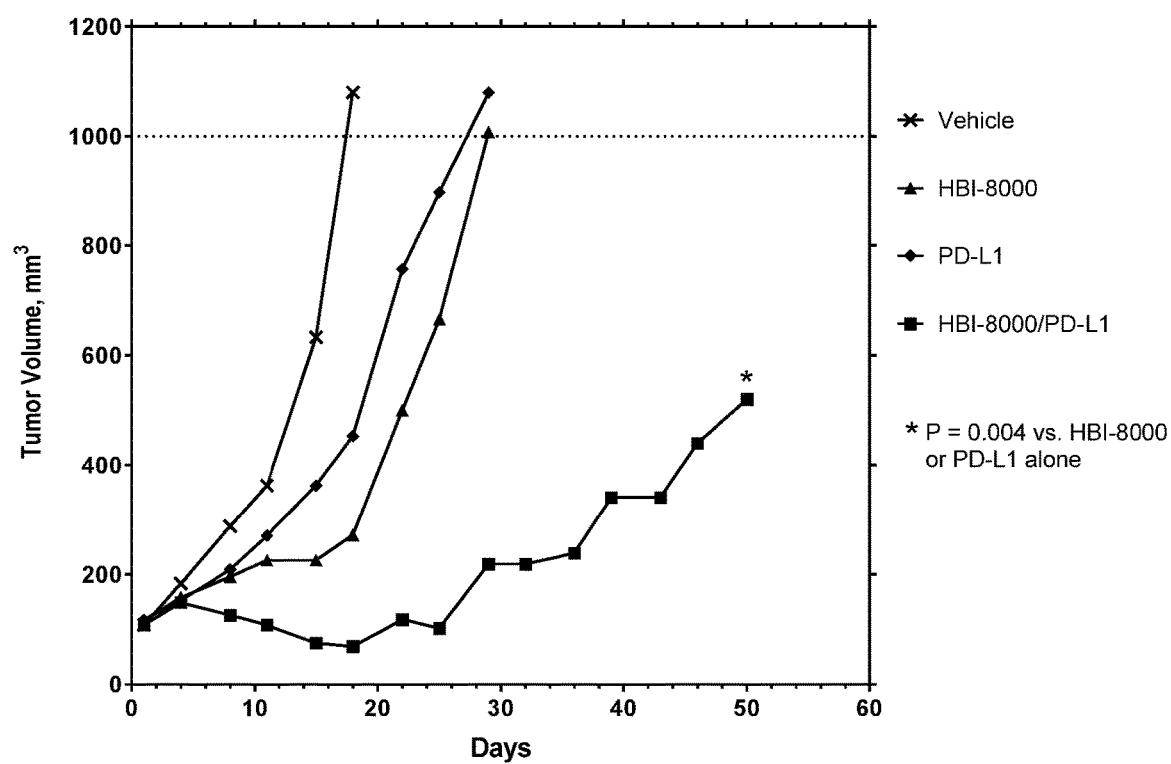

Fig. 6: Kaplan-Meier of Survival for Example 2
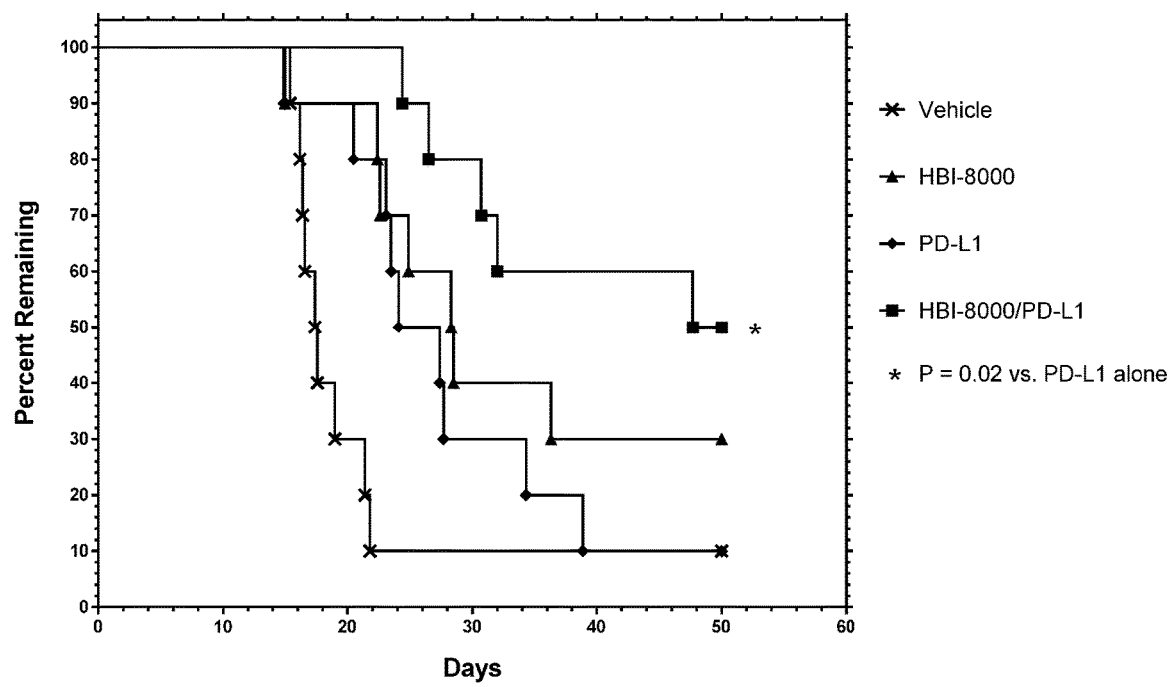

Fig. 7: Median Tumor Volume Measurements for Example 3
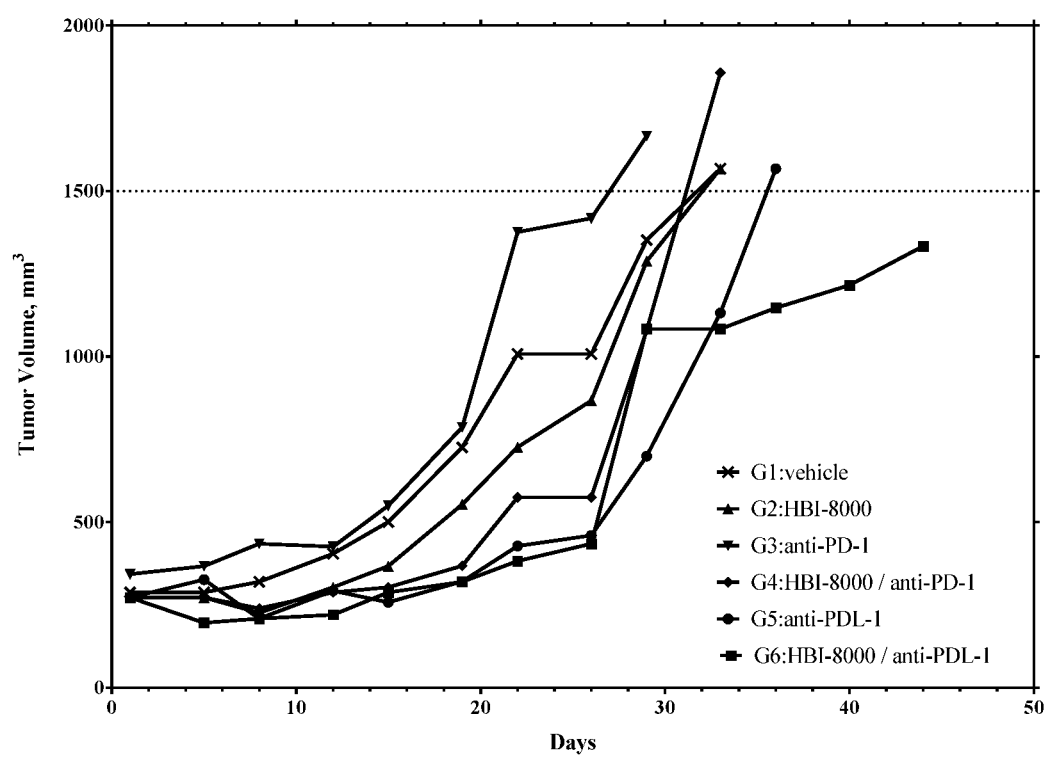

Fig. 8: Kaplan-Meier of Survival for Example 3
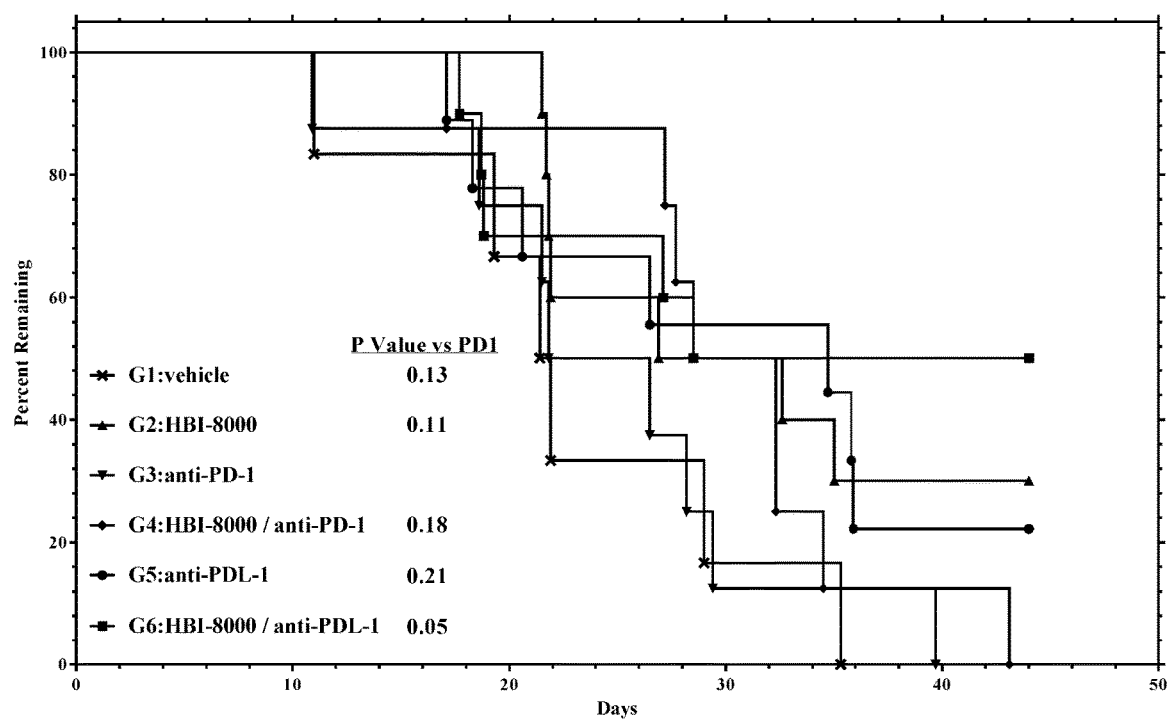

COMBINATION THERAPIES OF HDAC INHIBITORS AND PD-L1 INHIBITORS

CROSS-REFERENCE TO RELATED APPLICATIONS

This application is a continuation application of U.S. application Ser. No. 15/592,929, filed May 11, 2017, which claims priority to U.S. Provisional Application No. 62/335,056, filed May 11, 2016, all of which are hereby incorporated in their entireties including all tables, figures, and claims.

FIELD OF THE INVENTION

The present invention relates to combinations of HDAC inhibitors and PD-L1 inhibitors and the use of such combinations in the treatment of cancer

BACKGROUND OF THE INVENTION

Cancer is a significant cause of morbidity and mortality worldwide. While the standards of care for many different cancer types have greatly improved over the years, current standards of care still fail to meet the need for effective therapies to improve treatment of cancer. The clinical use of immuno-oncology agents targeting cytotoxic T-lymphocyte-associated protein 4 (CTLA-4) and the programmed cell death receptor-1 (PD-1) and its ligand PD-L1, have resulted in improvements over the standard of care in the treatment of many cancer types. While these checkpoint inhibitors have produced improved clinical responses in such certain cancers, durable clinical responses only occur in approximately 10-45% of patients. Moreover, a significant number of tumors are either resistant or become refractory. Epigenetic modifiers such as histone deacetylase inhibitors (HDACi) have been successful in the treatment of some hematologic malignancies, but despite preclinical data demonstrating activity against solid tumors, this result has not translated to the clinic as a monotherapy. Accordingly, there is a need in the art for new therapies, including, for example, combination therapies for the treatment of cancers. Provided herein are solutions to these and other problems in the art.

BRIEF SUMMARY

Provided herein, inter alia, are combinations that include an HDAC inhibitor (HDACi) and a PD-L1 inhibitor. The combinations include a compound of formula I and a PD-L1 inhibitor. In certain instances the PD-L1 inhibitor is a PD-L1 inhibitor antibody.

In a first aspect is a combination that includes a therapeutically effective amount of a PD-L1 inhibitor and a therapeutically effective amount of a compound of formula I:

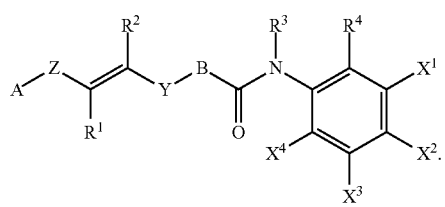

A is phenyl or a heterocyclic group, optionally substituted with 1 to 4 substituents selected from the group consisting of halogen, —OH, —NH$_2$, —NO$_2$, —CN, —COOH, $C_1$-$C_4$ alkyl, $C_1$-$C_4$ alkoxy, $C_1$-$C_4$ aminoalkyl, $C_1$-$C_4$ alkylamino, $C_2$-$C_4$ acyl, $C_2$-$C_4$ acylamino, $C_1$-$C_4$ alkythio, $C_1$-$C_4$ perfluoroalkyl, $C_1$-$C_4$ perfluoroalkyloxy, $C_1$-$C_4$ alkoxycarbonyl, phenyl, and a heterocyclic group. B is phenyl optionally substituted with 1 to 3 substituents selected from the group consisting of halogen, —OH, —NH$_2$, —NO$_2$, —CN, —COOH, $C_1$-$C_4$ alkyl, $C_1$-$C_4$ alkoxy, $C_1$-$C_4$ aminoalkyl, $C_1$-$C_4$ alkylamino, $C_2$-$C_4$ acyl, $C_2$-$C_4$ acylamino, $C_1$-$C_4$ alkylthio, $C_1$-$C_4$ perfluoroalkyl, $C_1$-$C_4$ perfluoroalkyloxy, $C_1$-$C_4$ alkoxycarbonyl, and phenyl. Y is a moiety comprising —CO— which is linear and in which the distances between the centroid of ring B (W1), the centroid of ring A (W2) and an oxygen atom as a hydrogen bond acceptor in the moiety Y (W3) are: W1-W2=about 6.0 Å, W1-W3=about 3.0 Å to about 6.0 Å, and W2-W3=about 4.0 Å to about 8.0 Å, respectively. Z is a bond or $C_1$-$C_4$ alkylene, —O—, —S—, —NH—, —CO—, —CS—, —SO—, or —SO$_2$—. $R^1$ and $R^2$ are independently hydrogen or $C_1$-$C_4$ alkyl. $R^3$ is hydrogen or $C_1$-$C_4$ alkyl. $R^4$ is hydrogen or —NH$_2$. One of $X^1$, $X^2$, $X^3$, or $X^4$ is halogen, —OH, —NH$_2$, —NO$_2$, —CN, —COOH, $C_1$-$C_4$ alkyl, $C_1$-$C_4$ alkoxy, $C_1$-$C_4$ aminoalkyl, $C_1$-$C_4$ alkylamino, $C_2$-$C_4$ acyl, $C_2$-$C_4$ acylamino, $C_1$-$C_4$ alkylthio, $C_1$-$C_4$ perfluoroalkyl, $C_1$-$C_4$ perfluoroalkyloxy, or $C_1$-$C_4$ alkoxycarbonyl optionally substituted with halogen or $C_1$-$C_4$ alkyl, while the others of $X^1$, $X^2$, $X^3$, or $X^4$ are independently hydrogen, provided, however, that when $R^4$ is hydrogen, one of $X^1$, $X^2$, $X^3$, or $X^4$ is —NH$_2$, an aminoalkyl group or an alkylamino group.

In one embodiment, the compound of formula I is N-(2-amino-4-fluorophenyl)-4-[[[(2E)-1-oxo-3-(3-pyridinyl)-2-propen-1-yl]amino]methyl]benzamide, referred to herein as HBI-8000, or chidamide.

In another embodiment, the PD-L1 inhibitor is a small molecule compound, a nucleic acid, a peptide, a protein, an antibody, a peptibody, a diabody, a minibody, a single-chain variable fragment (ScFv), or a fragment or variant thereof.

In still another embodiment, the PD-L1 inhibitor is an antibody.

In yet another embodiment, the PD-L1 inhibitor antibody is selected from durvalumab, avelumab, atezolizumab, BMS-936559, STI-A1010, STI-A1011, STI-A1012, STI-A1013, STI-A1014, or STI-A1015 (Sorrento Therapeutics).

In another aspect is a pharmaceutical composition that includes a combination described herein and a pharmaceutically acceptable excipient.

In still another aspect is a kit that includes a combination or a pharmaceutical composition as described herein.

In still another aspect is a method for treating cancer by administering a therapeutically effective amount of a combination or a pharmaceutical composition described herein to a patient in need thereof.

In one embodiment, the combination included in the methods includes a compound of formula I and a PD-L1 inhibitor antibody. The PD-L1 inhibitor antibody can be durvalumab, avelumab, atezolizumab, BMS-936559, r STI-A1010, STI-A1011, STI-A1012, STI-A1013, STI-A1014, or STI-A1015 (Sorrento Therapeutics).

In yet another aspect is method for reducing a level of myeloid-derived suppressor cells (MDSC) in a patient in need thereof by administering a therapeutically effective amount of a combination or pharmaceutical composition described herein.

In yet another aspect is method for reducing a level of regulatory T cells (Treg cells) in a patient in need thereof by administering a therapeutically effective amount of a combination or pharmaceutical composition described herein.

In another aspect is a method for enhancing the activity of a natural killer (NK) or cytotoxic T-cell activity in-vivo in a cancer patient by administering a therapeutically effective amount of a combination or pharmaceutical composition described herein.

In another aspect is a method for enhancing antibody-dependent cell-mediated cytotoxicity in a cancer patient by administering a therapeutically effective amount of a combination or pharmaceutical composition described herein.

In another aspect is a method for treating a cancer that has become resistant to treatment with a PD-1 inhibitor wherein such cancer is treated with a combination of an HDAC inhibitor and PD-L1 inhibitor. In embodiments of this aspect the HDAC inhibitor is a compound of formula I including HBI-8000 also know as chidamide.

DESCRIPTION OF THE FIGURES

FIG. 1 illustrates group tumor growth as median tumor volume ($mm^3$, y-axis) over time (days, x-axis) for all groups in the study described in Example 1 herein.

FIG. 2 illustrates group tumor growth as median tumor volume ($mm^3$, y-axis) over time (days, x-axis) for mice treated with compound (HBI-8000) at 50 mg/kg in the study described in Example 1 herein.

FIG. 3 illustrates survival (Kaplan-Meier) for all groups tested in the study described in Example 1 herein.

FIG. 4 illustrates survival (Kaplan-Meier) for mice treated with compound (HBI-8000) at 50 mg/kg in the study described in Example 1 herein.

FIG. 5 illustrates group tumor growth as median tumor volume ($mm^3$, y-axis) over time (days, x-axis) for all groups in the study described in Example 2 herein.

FIG. 6 illustrates survival (Kaplan-Meier) for all groups tested in the study described in Example 2 herein.

FIG. 7 illustrates group tumor growth as median tumor volume ($mm^3$, y-axis) over time (days, x-axis) for all groups in the study described in Example 3 herein.

FIG. 8 illustrates survival (Kaplan-Meier) for all groups tested in the study described in Example 3 herein.

DETAILED DESCRIPTION

Definitions

All patents, applications, published applications and other publications cited herein are incorporated by reference in their entirety. Unless defined otherwise, all technical and scientific terms used herein have the same meaning as commonly understood by those of ordinary skill in the art to which the invention belongs. The chemical structures and formulae set forth herein are constructed according to the standard rules of chemical valency known in the chemical arts. Should a discrepancy exist between a depicted structure and a name given for that structure, the depicted structure is to be accorded more weight. Where the stereochemistry of a structure or a portion of a structure is not indicated in a depicted structure or a portion of the depicted structure, the depicted structure is to be interpreted as encompassing all of its possible stereoisomers.

Any methods, devices and materials similar or equivalent to those described herein can be used in the practice of this invention. The following definitions are provided to facilitate understanding of certain terms used frequently herein and are not meant to limit the scope of the present disclosure. In the event that there is a plurality of definitions for a term herein, those in this section prevail unless stated otherwise. Headings used herein are for organizational purposes only and in no way limit the invention described herein.

The term "PD-L1 inhibitor" refers to a moiety (e.g., compound, nucleic acid, polypeptide, antibody) that decreases, inhibits, blocks, abrogates or interferes with the activity, binding of PD-L1 to its receptor, PD-1, or expression of PD-L1 (e.g., Programmed Cell Death 1 Ligand; PD-L1 (CD274); GI: 30088843), including variants, isoforms, species homologs of huma PD-L1 (e.g., mouse) and analogs that have at least one common epitope with PD-L. A PD-L1 inhibitor includes molecules and macromolecules such as, for example, compounds (small molecule compounds), nucleic acids, polypeptides, antibodies, peptibodies, diabodies, minibodies, single-chain variable fragments (ScFv), and fragments or variants thereof. Thus, a PD-L1 inhibitor as used herein refers to any moiety that antagonizes PD-L1 activity, its binding to PD-1, or its expression. PD-L1 inhibitor efficacy can be measured, for example, by its inhibitor concentration at 50% (half-maximal inhibitor concentration or $IC_{50}$). PD-L1 inhibitors include exemplary compounds and compositions described herein. A PD-L1 inhibitor antibody refers to a PD-L1 inhibitor which is a monoclonal or polyclonal antibody as described herein.

The terms "durvalumab," "avelumab," "atezolizumab," "BMS-936559," "STI-A1010," "STI-A1011," "STI-A1012," "STI-A1013," "STI-A1014," and "STI-A1015" are used in accordance with their plain and ordinary meaning as understood in the art.

The terms "polypeptide" and "protein" are used interchangeably herein and refer to any molecule that includes at least 2 or more amino acids.

The term "effective amount" refers to the amount of a therapy (e.g., a combination provided herein or another active agent such as an anti-cancer agent described herein) which is sufficient to accomplish a stated purpose or otherwise achieve the effect for which it is administered. An effective amount can be sufficient to reduce and/or ameliorate the progression, development, recurrence, severity and/or duration of a given disease, disorder or condition and/or a symptom related thereto, or can be sufficient to reduce the level of activity or binding of a polypeptide (e.g., PD-L1). An effective amount can be a "therapeutically effective amount" which refers to an amount sufficient to provide a therapeutic benefit such as, for example, the reduction or amelioration of the advancement or progression of a given disease, disorder or condition, reduction or amelioration of the recurrence, development or onset of a given disease, disorder or condition, and/or to improve or enhance the prophylactic or therapeutic effect(s) of another therapy. A therapeutically effective amount of a composition described herein can enhance the therapeutic efficacy of another therapeutic agent.

The term "regimen" refers to a protocol for dosing and timing the administration of one or more therapies (e.g., combinations described herein or another active agent such as an anti-cancer agent described herein) for treating a disease, disorder, or condition described herein. A regimen can include periods of active administration and periods of rest as known in the art. Active administration periods include administration of combinations and compositions described herein and the duration of time of efficacy of such combinations and compositions. Rest periods of regimens described herein include a period of time in which no compound is actively administered, and in certain instances, includes time periods where the efficacy of such compounds can be minimal. Combination of active administration and rest in regimens described herein can increase the efficacy and/or duration of administration of the combinations and compositions described herein.

The terms "therapies" and "therapy" refer to any protocol(s), method(s), and/or agent(s) that can be used in the prevention, treatment, management, and/or amelioration of a disease, disorder, or condition or one or more symptoms thereof. In certain instances the term refers to active agents such as an anti-cancer agent described herein. The terms "therapy" and "therapy" can refer to anti-viral therapy, anti-bacterial therapy, anti-fungal therapy, anti-cancer therapy, biological therapy, supportive therapy, and/or other therapies useful in treatment, management, prevention, or amelioration of a disease, disorder, or condition or one or more symptoms thereof known to one skilled in the art, for example, a medical professional such as a physician.

The term "patient" or "subject" refers to a mammal, such as a human, bovine, rat, mouse, dog, monkey, ape, goat, sheep, cow, or deer. Generally a patient as described herein is human.

The terms "inhibition", "inhibit", "inhibiting" refer to a reduction in the activity, binding, or expression of a polypeptide or reduction or amelioration of a disease, disorder, or condition or a symptom thereof. Inhibiting as used here can include partially or totally blocking stimulation, decreasing, preventing, or delaying activation or binding, or inactivating, desensitizing, or down-regulating protein or enzyme activity or binding.

Antibodies described herein can be polyclonal or monoclonal and include xenogeneic, allogeneic, or syngeneic forms and modified versions thereof (e.g., humanized or chimeric). An "antibody" is intended to mean a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See Borrebaeck (ed.) (1995) *Antibody Engineering*, Second Edition, Oxford University Press.; Kuby (1997) *Immunology*, Third Edition, W. H. Freeman and Company, New York). Specific molecular antigens that can be bound by an antibody described herein include PD-L1 and its epitopes.

The term "monoclonal antibody(ies)" refers to a population of antibody molecules that contain one species of an antigen binding site capable of immunoreacting with a particular epitope of an antigen, whereas the term "polyclonal antibody(ies)" refers to a population of antibody molecules that contain multiple species of antigen binding sites capable of interacting with a particular antigen. A monoclonal antibody, typically displays a single binding affinity for a particular antigen with which it immunoreacts. For example, the monoclonal antibodies to be used in accordance with the present invention can be made by a variety of techniques, including, for example, the hybridoma method (e.g., Kohler and Milstein., *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Ma.rks et al., *J Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lon berg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein also include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, pp. 6851-6855 (1984)). "Humanized antibody(ies)" can be considered as a subset of chimeric antibodies described herein.

The term "human" when used in reference to an antibody or a functional fragment thereof (e.g., "humanized antibody(ies))" refers an antibody or functional fragment thereof that has a human variable region or a portion thereof corresponding to human germline immunoglobulin sequences. Such human germline immunoglobulin sequences are described by Kabat et al. (1991) *Sequences of Proteins of Immunological Interest*, Fifth Edition, U.S. Department of Health and Human Services, NIH Publication No. 91-3242. A human antibody, in the context of the present invention, can include an antibody that binds to PD-L1 or variants thereof as described herein.

In certain instances a human antibody is an antibody that possesses an amino acid sequence corresponding to that of an antibody produced by a human and/or has been made using any of the techniques for making human antibodies as disclosed herein. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boemer et al., *J. Immunol.*, 147(1):86-95 (1991). See also van Dijk and van de Winkel, *Curr. Opin. Pharmacol.*, 0.2: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE technology). See also, for example, Li et al., *Proc. Natl. Acad. Sci. USA*, 103:3557-3562 (2006) regarding human antibodies generated via a human B-cell hybridoma technology.

A "humanized antibody" refers to antibodies made by a non-human cell having variable or variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention can include amino acid residues not encoded by human germline immunoglobulin sequences (e.g., mutations introduced by random or site-specific mutagenesis in vitro or by somatic mutation in vivo), for example in the CDRs. Humanized antibodies can also include antibodies in which CDR sequences derived from the germline of another mammalian species, such as a mouse, have been grafted onto human framework sequences.

Humanized forms of non-human (e.g., murine) antibodies are antibodies that contain minimal sequence derived from non-human immunoglobulin. In one embodiment, a humanized antibody is a human immunoglobulin (recipient antibody) in which residues from a hypervariable region of the recipient are replaced by residues from an hypervariable region of a nonhuman species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies can comprise residues that are not found in the recipient antibody or in the donor antibody. These modifications can be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions can include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally can also include at least a portion of an immunoglobulin constant region (Fc), which can be a human immunoglobulin. Exemplary methods and humanized antibodies include those described by Jones et al. *Nature* 321: 522-525 (1986); Riechmann et al. *Nature* 332: 323-329 (1988); and Presta, *Curr. Op. Struct. Biol.* 2:593-596 (1992); Vaswani and Hamilton, *Ann. Allergy. Asthma & Immunol.* 1: 105-115 (1998); Harris, *Biochem. Soc. Transactions* 23:1035-1038 (1995); Burle and Gross, *Curr. Op. Biotech.* 5:428-433 (1994); and U.S. Pat. Nos. 6,982,321 and 7,087,409.

The term "functional fragment" when used in reference to an antibody refers to a portion of the antibody including heavy or light chain polypeptides that retains some or all of the binding activity as the antibody from which the fragment was derived. Such functional fragments can include, for example, an Fd, Fv, Fab, F(ab'), F(ab)$_2$, F(ab')$_2$, single chain Fv (ScFv), diabody, triabody, tetrabody and minibody. Other functional fragments can include, for example, heavy or light chain polypeptides, variable region polypeptides or CDR polypeptides or portions thereof so long as such functional fragments retain binding activity. Such antibody binding fragments can be found described in, for example, Harlow and Lane, *Antibodies: A Laboratory Manual*, Cold Spring Harbor Laboratory, New York (1989); Myers (ed.), *Molec. Biology and Biotechnology: A Comprehensive Desk Reference*, New York: VCH Publisher, Inc.; Huston et al., *Cell Biophysics*, 22:189-224 (1993); Plückthun and Skerra, *Meth. Enzymol.*, 178:497-515 (1989) and in Day, E. D., *Advanced Immunochemistry*, Second Ed., Wiley-Liss, Inc., New York, N.Y. (1990). *Antibody Engineering*, Second Edition, Oxford University Press, 1995.

The term "heavy chain" when used in reference to an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, referred to as alpha ($\alpha$), delta ($\delta$), epsilon ($\varepsilon$), gamma ($\gamma$) and mu ($\mu$), based on the amino acid sequence of the heavy chain constant region. The distinct heavy chains differ in size: $\alpha$, $\delta$ and $\gamma$ contain approximately 450 amino acids, while $\mu$ and $\varepsilon$ contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa ($\kappa$) of lambda ($\lambda$) based on the amino acid sequence of the constant domains. Light chain amino acid sequences are well known in the art. A light chain can be a human light chain.

The term "variable domain" or "variable region" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains can differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. Numbering of amino acid positions used herein is according to the EU Index, as in Kabat et al. (1991) *Sequences of proteins of immunological interest*. (U.S. Department of Health and Human Services, Washington, D.C.) $5^{th}$ Ed. A variable region can be a human variable region.

A CDR refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved β-sheet framework, and thus are able to adapt different conformations (Chothia and Lesk, *J. Mol. Biol.* 196:901-917 (1987)). Both terminologies are well recognized in the art. The positions of CDRs within a canonical antibody variable domain have been determined by comparison of numerous structures (Al-Lazikani et al., *J. Mol. Biol.* 273:927-948 (1997); Morea et al., *Methods* 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

For example, CDRs defined according to either the Kabat (hypervariable), Chothia (structural), or MacCallum (*J. Mol. Biol.* 262:732-745 (1996)) designations, as set forth in the Table 1 below:

TABLE 1

CDR Definitions

| | Kabat [1] | Chothia [2] | MacCallum [3] | Loop Location |
|---|---|---|---|---|
| $V_H$ CDR1 | 31-35 | 26-32 | 30-35 | linking B and C strands |
| $V_H$ CDR2 | 50-65 | 53-55 | 47-58 | linking C' and C" strands |
| $V_H$ CDR3 | 95-102 | 96-101 | 93-101 | linking F and G strands |
| $V_L$ CDR1 | 24-34 | 26-32 | 30-36 | linking B and C strands |
| $V_L$ CDR2 | 50-56 | 50-52 | 46-55 | linking C' and C" strands |
| $V_L$ CDR3 | 89-97 | 91-96 | 89-96 | linking F and G strands |

[1] Residue numbering follows the nomenclature of Kabat et al., supra
[2] Residue numbering follows the nomenclature of Chothia et al., supra The term "cancer" refers to any physiological condition in mammals characterized by unregulated cell growth. Cancers described herein include solid tumors and hematological (blood) cancers. A "hematological cancer" refers to any blood borne cancer and includes, for example, myelomas, lymphomas and leukemias. A "solid tumor" or "tumor" refers to a lesion and neoplastic cell growth and proliferation, whether malignant or benign, and all pre-cancerous and cancerous cells and tissues resulting in abnormal tissue growth. "Neoplastic," as used herein, refers to any form of dysregulated or unregulated cell growth, whether malignant or benign, resulting in abnormal tissue growth.

The terms "treating" or "treatment" refer to any indicia of success or amelioration of the progression, severity, and/or duration of a disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; or improving a patient's physical or mental well-being.

The term "enhance" refers to an increase or improvement in the function or activity of a protein or cell after administration or contacting with a combination described herein compared to the protein or cell prior to such administration or contact.

The term "administering" refers to the act of delivering a combination or composition described herein into a subject by such routes as oral, mucosal, topical, suppository, intravenous, parenteral, intraperitoneal, intramuscular, intralesional, intrathecal, intranasal or subcutaneous administration. Parenteral administration includes intravenous, intramuscular, intra-arteriole, intradermal, subcutaneous, intraperitoneal, intraventricular, and intracranial administration. Administration generally occurs after the onset of the disease, disorder, or condition, or its symptoms but, in certain instances, can occur before the onset of the disease, disorder, or condition, or its symptoms (e.g., administration for patients prone to such a disease, disorder, or condition).

The term "coadministration" refers to administration of two or more agents (e.g., a combination described herein and another active agent such as an anti-cancer agent described herein). The timing of coadministration depends in part of the combination and compositions administered and can include administration at the same time, just prior to, or just after the administration of one or more additional therapies, for example cancer therapies such as chemotherapy, hormonal therapy, radiotherapy, or immunotherapy. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g., to reduce metabolic degradation). The compounds described herein can be used in combination with one another, with other active agents known to be useful in treating cancer.

The term "anti-cancer agent" is used in accordance with its plain ordinary meaning and refers to a composition having anti-neoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The term "chemotherapeutic" or "chemotherapeutic agent" is used in accordance with its plain ordinary meaning and refers to a chemical composition or compound having anti-neoplastic properties or the ability to inhibit the growth or proliferation of cells. "Chemotherapy" refers to a therapy or regimen that includes administration of a chemotherapeutic or anti-cancer agent described herein.

The terms "halo," "halogen," and "halide" refer to —F, —Cl, —Br, and —I.

The term "alkyl" by itself or as part of another substituent refers to, unless otherwise stated, a straight (e.g., unbranched) or branched carbon chain (or carbon), or combination thereof, having no unsaturation and can include mono-, di- and multivalent radicals. An alkyl as defined herein can be designated by its number of carbon atoms (e.g., $C_1$-$C_{10}$ means one to ten carbons). Alkyls herein can include $C_1$-$C_{10}$, $C_1$-$C_8$, $C_1$-$C_6$, and $C_1$-$C_4$ lengths. A "perfluoroalkyl" refers to an alkyl in which all of the hydrogens in the alkyl chain are replaced with fluoro.

The term "alkoxy" refers to an alkyl group (e.g., $C_1$-$C_{10}$, $C_1$-$C_8$, $C_1$-$C_6$, and $C_1$-$C_4$ alkyl) attached to the remainder of the molecule via an oxygen linker (—O—). Exemplary alkoxy groups include groups having the formula —OR, where R is branched or linear alkyl. A "perfluoroalkoxyl" moiety refers to an alkoxy in which all of the hydrogens in the alkyl chain are replaced with fluoro.

The term "aminoalkyl" refers to an alkyl group (e.g., $C_1$-$C_{10}$, $C_1$-$C_8$, $C_1$-$C_6$, and $C_1$-$C_4$ alkyl) in which one or more hydrogen atoms are replaced with an amino group The term "alkylamino" refers to an alkyl group (e.g., $C_1$-$C_{10}$, $C_1$-$C_8$, $C_1$-$C_6$, and $C_1$-$C_4$ alkyl) attached to the remainder of the molecule via a nitrogen linker (—NR—).

Exemplary alkylamino groups include N-methylamino, N-ethylamino, N-isopropylamino, and the like.

The term "acyl" refers to a moiety having the formula, —C(O)R, where R is a substituted or unsubstituted alkyl, haloalkyl, or amino group. The term "acylamino" refers to an acyl moiety having an attached amino group and includes, for example, such moieties as acetylamino, propionylamino, butyrylamino, isobuytrylamino, and others.

The term "alkythio" refers to an alkyl group (e.g., $C_1$-$C_{10}$, $C_1$-$C_8$, $C_1$-$C_6$, and $C_1$-$C_4$ alkyl) attached to the remainder of the molecule via a sulfur linker (—S—). Exemplary alkylthio groups include methylthio, ethylthio, propylthio, and others.

The term "heterocycle" or "heterocyclyl" refers to a stable 3- to 15-membered monocyclic group that is saturated or unsaturated and contains one or more heteroatoms (e.g., N, O, or S). Exemplary heterocycles include, but are not limited to morpholinyl, piperidinyl, piperazinyl, pyranyl, pyrrolidinyl, pyrrolinyl, imidazolidinyl, imidazolinyl, oxetanyl, azetidinyl, and others.

Compositions

Provided herein are combinations (e.g., combination therapies and compositions) useful for treating a variety of diseases, disorders, and symptoms thereof, including for example, cancer. The combinations described herein include an HDAC inhibitor and PD-L1 inhibitor, such as a benzamide HDAC inhibitor of formula I and a PD-L1 inhibitor as described herein. In one aspect is a combination that includes a therapeutically effective amount of a PD-L1 inhibitor and a therapeutically effective amount of a compound of formula I:

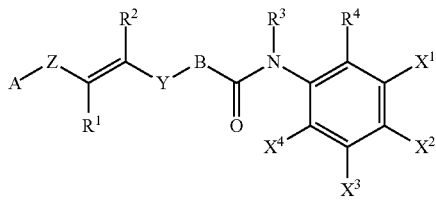

where:
- A is a phenyl or heterocyclic group, optionally substituted with 1 to 4 substituents selected from the group consisting of halogen, —OH, —$NH_2$, —$NO_2$, —CN, —COOH, $C_1$-$C_4$ alkyl, $C_1$-$C_4$ alkoxy, $C_1$-$C_4$ aminoalkyl, $C_1$-$C_4$ alkylamino, $C_2$-$C_4$ acyl, $C_2$-$C_4$ acylamino, $C_1$-$C_4$ alkythio, $C_1$-$C_4$ perfluoroalkyl, $C_1$-$C_4$ perfluoroalkyloxy, $C_1$-$C_4$ alkoxycarbonyl, phenyl, and a heterocyclic group;
- B is phenyl optionally substituted with 1 to 3 substituents selected from the group consisting of halogen, —OH, —$NH_2$, —$NO_2$, —CN, —COOH, $C_1$-$C_4$ alkyl, $C_1$-$C_4$ alkoxy, $C_1$-$C_4$ aminoalkyl, $C_1$-$C_4$ alkylamino, $C_2$-$C_4$ acyl, $C_2$-$C_4$ acylamino, $C_1$-$C_4$ alkylthio, $C_1$-$C_4$ perfluoroalkyl, $C_1$-$C_4$ perfluoroalkyloxy, $C_1$-$C_4$ alkoxycarbonyl, and phenyl;
- Y is a moiety comprising —CO— which is linear and in which the distances between the centroid of ring B (W1), the centroid of ring A (W2) and an oxygen atom as a hydrogen bond acceptor in the moiety Y (W3) are: W1-W2=about 6.0 Å, W1-W3=about 3.0 Å to about 6.0 Å, and W2-W3=about 4.0 Å to about 8.0 Å, respectively;
- Z is a bond or $C_1$-$C_4$ alkylene, —O—, —S—, —NH—, —CO—, —CS—, —SO—, or —$SO_2$—;
- $R^1$ and $R^2$ are independently hydrogen or $C_1$-$C_4$ alkyl;
- $R^3$ is hydrogen or $C_1$-$C_4$ alkyl;
- $R^4$ is hydrogen or —$NH_2$; and
- one of $X^1$, $X^2$, $X^3$, or $X^4$ is halogen, —OH, —$NH_2$, —$NO_2$, —CN, —COOH, $C_1$-$C_4$ alkyl, $C_1$-$C_4$ alkoxy, $C_1$-$C_4$ aminoalkyl, $C_1$-$C_4$ alkylamino, $C_2$-$C_4$ acyl, $C_2$-$C_4$ acylamino, $C_1$-$C_4$ alkylthio, $C_1$-$C_4$ perfluoroalkyl, $C_1$-$C_4$ perfluoroalkyloxy, or $C_1$-$C_4$ alkoxycarbonyl optionally substituted with halogen or $C_1$-$C_4$ alkyl, while the others of $X^1$, $X^2$, $X^3$, or $X^4$ are independently hydrogen,
  provided, however, that when $R^4$ is hydrogen, one of $X^1$, $X^2$, $X^3$, or $X^4$ is —$NH_2$, an aminoalkyl group or an alkylamino group.

In certain instances A is phenyl or phenyl optionally substituted with halogen, —OH, —$NH_2$, —$NO_2$, —CN, —COOH, $C_1$-$C_4$ alkyl, $C_1$-$C_4$ alkoxy, $C_1$-$C_4$ aminoalkyl, $C_1$-$C_4$ alkylamino, $C_2$-$C_4$ acyl, $C_2$-$C_4$ acylamino, $C_1$-$C_4$ alkythio, $C_1$-$C_4$ perfluoroalkyl, $C_1$-$C_4$ perfluoroalkyloxy, $C_1$-$C_4$ alkoxycarbonyl, phenyl, or a heterocyclic group. A can be a heterocyclic group (e.g., a 5 to 10-membered heterocyclic group) containing a —N—, —S—, or —O— moiety. In certain instances A is a 5 to 10-membered N-heterocyclic moiety having 1, 2, 3, 4, or more nitrogen heteroatoms, such as for example, pyrrolidinyl, pyrrolinyl, imidazolidinyl, imdazolyl, pyrazolidinyl, pyrazolyl, oxazolidinyl, oxazolyl, thiazolidinyl, thiazolyl, piperidinyl, pyridinyl, piperizinyl, diazinyl, tetrazolyl, triazinyl, tetrazinyl, azepinyl, diazepinyl, azocanyl, or azocinyl. A can be a saturated or unsaturated 5 to 10 membered N-heterocyclic moiety. In certain instances A is a 6-membered N-heterocyclic moiety, such as for example, pyridine.

In certain embodiments, B is phenyl. B can be phenyl optionally substituted with a small moiety such as, for example, halogen, —OH, —$NH_2$, —$NO_2$, —CN, —COOH, or $C_1$-$C_4$ alkyl. In some embodiments B is phenyl substituted with halogen. In other embodiments, B is substituted with an electron donating group (EDG). In still other embodiments, B is phenyl substituted with an electron withdrawing group (EWG). In yet another embodiment, B is phenyl substituted with $C_1$-$C_4$ alkyl. B can be methyl-, ethyl-, or propyl-substituted phenyl. B can be methoxy-, ethoxy-, or propoxy-substituted phenyl.

In certain instances Y is —C(O)NH—$CH_2$—. In certain embodiments, Z is a bond. Z can be a methylene, ethylene, or propylene moiety. In some embodiments, Z is —O—, —S—, —NH—, —CO—, —CS—, —SO—, or —$SO_2$—.

$R^1$ and $R^2$ are in certain instances both hydrogen. $R^1$ and $R^2$ can both be $C_1$-$C_4$ alkyl, for example, $R^1$ and $R^2$ can both be methyl, ethyl, or propyl. In certain instances if one of $R^1$ or $R^2$ is hydrogen the other is $C_1$-$C_4$ alkyl (e.g., methyl). $R^3$ can be hydrogen. In other embodiments, $R^3$ is $C_1$-$C_4$ alkyl (e.g., methyl or ethyl).

$R^4$ can be —$NH_2$. In certain instances $R^4$ is —$NH_2$ where one of $X^1$, $X^2$, $X^3$, or $X^4$ is halogen. When $R^4$ is —$NH_2$, $X^2$ or $X^3$ can be halogen. In one embodiment $R^4$ is —$NH_2$ and $X^2$ is halogen. In such instances $X^2$ can be —F.

In another embodiment, $R^1$, $R^2$, and $R^3$ are hydrogen where Z is a bond, $R^4$ is —$NH_2$ and Y is —C(O)NH—$CH_2$—. In such embodiments, A can be a heterocyclic moiety as described above and B can be phenyl. $X^1$, $X^2$, $X^3$, or $X^4$ can be halogen (e.g., —F) or —$NH_2$.

The compound of formula I can be a compound as substantially described by U.S. Pat. Nos. 7,244,751 and 7,550,490 both of which are incorporated herein in their entireties for all purposes. In one embodiment the compound of formula I is N-(2-amino-4-fluorophenyl)-4-[[[(2E)-1-oxo-3-(3-pyridinyl)-2-propen-1-yl]amino]methyl]benzamide.

In another embodiment the compound of formula I has the formula Ia as set forth below:

Ia

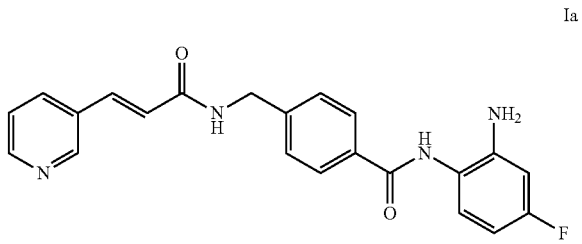

Compounds of formula I as described herein include pharmaceutically acceptable salts, pharmaceutically acceptable stereoisomers, prodrugs, enantiomers, diastereomers, hydrates, co-crystals, and polymorphs thereof.

In certain instances, the combination includes a compound of formula I (e.g., Ia) present at an amount of greater than about: 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, 80 mg, 85 mg, 90 mg, 100 mg, 125 mg, 150 mg, 175 mg, or 200 mg. The combination can include a compound of formula I present at an amount greater than about: 1 mg, 2 mg, 3 mg, 4 mg, 5 mg, 6 mg, 7 mg, 8 mg, 9 mg, or 10 mg. In certain instances the compound of formula I is present in an amount greater than about 5 mg or about 10 mg. The combination can include a compound of formula I present at an amount greater than about: 1 mg to about 10 mg, 1 mg to about 25 mg, 1 mg to about 50 mg, 5 mg to about 10 mg, 5 mg to about 25 mg, 5 mg to about 50 mg, 10 mg to about 25 mg, 10 mg to about 50 mg, 50 mg to about 100 mg, or 100 mg to about 200 mg.

The combination can include a compound present in an amount of at least about: 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, 80 mg, 85 mg, 90 mg, 100 mg, 125 mg, 150 mg, 175 mg, or 200 mg. The combination can include a compound of formula I present at an amount of at least about: 1 mg, 2 mg, 3 mg, 4 mg, 5 mg, 6 mg, 7 mg, 8 mg, 9 mg, or 10 mg. In certain instances the compound of formula I is present in an amount of at least about 5 mg or about 10 mg. The combination can include a compound of formula I present at an amount of at least about: 1 mg to about 10 mg, 1 mg to about 25 mg, 1 mg to about 50 mg, 5 mg to about 10 mg, 5 mg to about 25 mg, 5 mg to about 50 mg, 10 mg to about 25 mg, 10 mg to about 50 mg, 50 mg to about 100 mg, or 100 mg to about 200 mg.

The combination can include a compound present in an amount of about: 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, 80 mg, 85 mg, 90 mg, 100 mg, 125 mg, 150 mg, 175 mg, or 200 mg. The combination can include a compound of formula I present at an amount of about: 1 mg, 2 mg, 3 mg, 4 mg, 5 mg, 6 mg, 7 mg, 8 mg, 9 mg, or 10 mg. In certain instances the compound of formula I is present in an amount of about 5 mg or about 10 mg. The combination can include a compound of formula I present at an amount of about: 1 mg to about 10 mg, 1 mg to about 25 mg, 1 mg to about 50 mg, 5 mg to about 10 mg, 5 mg to about 25 mg, 5 mg to about 50 mg, 10 mg to about 25 mg, 10 mg to about 50 mg, 50 mg to about 100 mg, or 100 mg to about 200 mg.

A compound of formula I can be present in the combinations described herein relative to the weight of the patient (e.g., mg/kg). In some instances, the compound of formula I is present in an amount equivalent to about: 0.0001 mg/kg to about 200 mg/kg, 0.001 mg/kg to about 200 mg/kg, 0.01 mg/kg to about 200 mg/kg, 0.01 mg/kg to about 150 mg/kg, 0.01 mg/kg to about 100 mg/kg, 0.01 mg/kg to about 50 mg/kg, 0.01 mg/kg to about 25 mg/kg, 0.01 mg/kg to about 10 mg/kg, or 0.01 mg/kg to about 5 mg/kg, 0.05 mg/kg to about 200 mg/kg, 0.05 mg/kg to about 150 mg/kg, 0.05 mg/kg to about 100 mg/kg, 0.05 mg/kg to about 50 mg/kg, 0.05 mg/kg to about 25 mg/kg, 0.05 mg/kg to about 10 mg/kg, or 0.05 mg/kg to about 5 mg/kg, 0.5 mg/kg to about 200 mg/kg, 0.5 mg/kg to about 150 mg/kg, 0.5 mg/kg to about 100 mg/kg, 0.5 mg/kg to about 50 mg/kg, 0.5 mg/kg to about 25 mg/kg, 0.5 mg/kg to about 10 mg/kg, or 0.5 mg/kg to about 5 mg/kg. In other instances the compound of formula I is present in an amount equivalent to about: 1 mg/kg to about 200 mg/kg, 1 mg/kg to about 150 mg/kg, 1 mg/kg to about 100 mg/kg, 1 mg/kg to about 50 mg/kg, 1 mg/kg to about 25 mg/kg, 1 mg/kg to about 10 mg/kg, or 1 mg/kg to about 5 mg/kg.

PD-L1 inhibitors useful in the combinations described herein include any molecule capable of inhibiting, blocking, abrogating or interfering with the binding of PD-L1 to PD-1, activity or expression of PD-L1. In particular, a PD-L1 inhibitor can be a small molecule compound, a nucleic acid, a polypeptide, an antibody, a peptibody, a diabody, a minibody, a single-chain variable fragment (ScFv), or a functional fragment or variant thereof. In one instance the PD-L1 inhibitor is a small molecule compound (e.g., a compound having a molecule weight of less than about 1000 Da). In one embodiment, the PD-L1 inhibitor is CA-170 (AUPM-170; Curis, Inc.). In other instances, useful PD-L1 inhibitors in the combinations described herein include nucleic acids and polypeptides. The PD-L1 inhibitor can be a polypeptide (e.g., macrocyclic polypeptide) such as those exemplified in U.S. Patent Application Publication No.: 2014/0294898, which is incorporated herein by reference in its entirety and for all purposes. In one example, the PD-L1 inhibitor is an antibody, peptibody, diabody, minibody, ScFv, or a functional fragment thereof. In another example, the PD-L1 inhibitor is a PD-L1 inhibitor antibody. The PD-L1 inhibitor antibody can be a monoclonal or polyclonal antibody. In certain embodiments, the PD-L1 inhibitor antibody is a monoclonal antibody.

PD-L1 antibodies include all known types of antibodies and functional fragments thereof, including but not limited to, those exemplified herein such as, for example, human antibodies, mouse antibodies, chimeric antibodies, humanized antibodies, or chimeric humanized antibodies.

In one embodiment, the PD-L1 inhibitor antibody is a human antibody. In another embodiment, the PD-L1 inhibitor antibody is a mouse antibody. In still another embodiment, the PD-L1 inhibitor antibody is a chimeric antibody. In yet another embodiment, the PD-L1 inhibitor antibody is a humanized antibody. In yet another embodiment, the PD-L1 inhibitor antibody is a chimeric humanized antibody. The PD-L1 inhibitor antibody can be a human antibody or humanized antibody. The PD-L1 inhibitor antibody can be durvalumab, avelumab, atezolizumab, BMS-936559, STI-A1010, STI-A1011, STI-A1012, STI-A1013, STI-A1014, or STI-A1015. In some embodiments, two or more PD-L1 antibodies are administered in combination with a compound of formula I as described herein.

The PD-L1 inhibitor antibody can be durvalumab. Durvalumab is an Fc optimized monoclonal antibody directed against PD-L1, with potential immune checkpoint inhibitory and anti-neoplastic activities. Without being bound by any particular theory, durvalumab binds to PD-L1, thereby blocking its binding to and activation of its receptor, PD-1, which can be expressed on activated T-cells. This can reverse T-cell inactivation and activate the immune system to exert a cytotoxic T-lymphocyte (CTL) response against PD-L-expressing tumor cells. The Fc region of durvalumab is modified in such a way that it does not induce either antibody-dependent cytotoxicity (ADCC) or complement-dependent cytotoxicity (CDC).

The PD-L1 inhibitor antibody can be avelumab. Avelumab is a human immunoglobulin G1 (IgG1) monoclonal antibody directed against PD-L1, with potential immune checkpoint inhibitory and anti-neoplastic activities. Without being bound by any particular theory, avelumab binds to PD-L1 and prevents the interaction of PD-L1 with its receptor, PD-1. This inhibits the activation of PD-1 and its downstream signaling pathways. This can restore immune function through the activation of cytotoxic T-lymphocytes (CTLs) targeted to PD-L1-overexpressing tumor cells. Avelumab appears to induce an antibody-dependent cellular cytotoxic (ADCC) response against PD-L-expressing tumor cells.

The PD-L1 inhibitor antibody can be atezolizumab. Atezolizumab is a human, Fc optimized, monoclonal antibody directed against the protein ligand PD-L1, with potential immune checkpoint inhibitory and anti-neoplastic activities. Without being bound by any particular theory, atezolizumab binds to PD-L1, blocking its binding to and activation of its receptor, PD-1, expressed on activated T-cells, which may enhance the T-cell-mediated immune response to neoplasms and reverse T-cell inactivation. In addition, by binding to PD-L1, atezolizumab also appears to prevent binding of PD-L1 to B7.1 expressed on activated T cells, which can further enhance the T-cell-mediated immune response. The Fc region of atezolizumab is modified in such a way that it does not induce either antibody-dependent cytotoxicity (ADCC) or complement-dependent cytotoxicity (CDC).

The PD-L1 inhibitor antibody can be BMS-936559. BMS-936559 is a fully human IgG4 monoclonal antibody directed against PD-L1, with potential immune checkpoint inhibitory activity. Without being bound by any particular theory, BMS-936559 binds to PD-L1 and inhibits its binding to both PD-1 and CD80.

The PD-L1 inhibitor antibody can be STI-A1010, STI-A1011, STI-A1012, STI-A1013, STI-A1014, or STI-A1015. STI-A1010, STI-A1011, STI-A1012, STI-A1013, STI-A1014, and STI-A1015 (Sorrento Therapeutics) are fully human monoclonal antibodies that are each directed against PD-L1.

A PD-L1 inhibitor antibody can be of any antibody isotype. The term isotype refers to the antibody class that is encoded by heavy chain constant region genes. The heavy chains of a given antibody or functional fragment determine the class of that antibody or functional fragment: IgM, IgG, IgA, IgD or IgE. Each class can have either κ or λ light chains. The term subclass refers to the minor differences in amino acid sequences of the heavy chains that differentiate the subclasses. In humans there are two subclasses of IgA (subclasses IgA1 and IgA2) and there are four subclasses of IgG (subclasses IgG1, IgG2, IgG3 and IgG4). Such classes and subclasses are well known to those skilled in art.

Useful PD-L1 antibodies bind to PD-L1 with sufficient strength to inhibit activity of PD-L1. The term bind as used herein refers to an interaction between molecules to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions or forces. Binding of an antibody or functional fragment thereof can be detected using, for example, an enzyme-linked immunosorbant assay or any one of a number of methods that are well known to those skilled in the art.

The strength of the total non-covalent interactions between a single antigen-binding site on a PD-L1 inhibitor antibody or functional fragment and a single epitope of a target molecule, such as PD-L1, is the affinity of the antibody or functional fragment for that epitope. The ratio of association ($k_1$) to dissociation ($k_{-1}$) of an antibody or functional fragment thereof to a monovalent antigen ($k_1/k_{-1}$) is the association constant K, which is a measure of affinity. The value of K varies for different complexes of antibody or functional fragment and antigen and depends on both $k_1$ and $k_{-1}$. The association constant K for an antibody or functional fragment of the invention can be determined using any method provided herein or any other method well known to those skilled in the art.

The affinity at one binding site does not always reflect the true strength of the interaction between an antibody or functional fragment and an antigen. When complex antigens containing multiple, repeating antigenic determinants come in contact with antibodies containing multiple binding sites, the interaction of such an antibody or functional fragment with antigen at one site will increase the probability of a reaction at a second site. The strength of such multiple interactions between a multivalent antibody and antigen is called the avidity. The avidity of an antibody or functional fragment can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

The specificity of a PD-L1 inhibitor antibody or functional fragment thereof refers to the ability of an individual antibody or functional fragment thereof to react with only one antigen (e.g., a single epitope of PD-L1). An antibody or functional fragment can be considered specific when it can distinguish differences in the primary, secondary or tertiary structure of an antigen or isomeric forms of an antigen.

The PD-L1 inhibitor antibody can be present in an amount as a measure with regards to the weight of the patient in need thereof. For example, the PD-L1 inhibitor antibody can be present in an amount of about: 0.1 mg/kg to about 50 mg/kg, 0.1 mg/kg to about 40 mg/kg, 0.1 mg/kg to about 30 mg/kg, 0.1 mg/kg to about 25 mg/kg, 0.1 mg/kg to about 20 mg/kg, 0.1 mg/kg to about 15 mg/kg, 0.1 mg/kg to about 10 mg/kg, 0.1 mg/kg to about 7.5 mg/kg, 0.1 mg/kg to about 5 mg/kg, 0.1 mg/kg to about 2.5 mg/kg, or about 0.1 mg/kg to about 1 mg/kg. The PD-L1 inhibitor antibody can be present in an amount of about: 0.5 mg/kg to about 50 mg/kg, 0.5 mg/kg to about 40 mg/kg, 0.5 mg/kg to about 30 mg/kg, 0.5 mg/kg to about 25 mg/kg, 0.5 mg/kg to about 20 mg/kg, 0.5 mg/kg to about 15 mg/kg, 0.5 mg/kg to about 10 mg/kg, 0.5 mg/kg to about 7.5 mg/kg, 0.5 mg/kg to about 5 mg/kg, 0.5 mg/kg to about 2.5 mg/kg, or about 0.5 mg/kg to about 1 mg/kg. The PD-L1 inhibitor antibody can be present in an amount of about 0.5 mg/kg to about 5 mg/kg or about 0.1 mg/kg to about 10 mg/kg. The PD-L1 inhibitor antibody can be present in an amount of about 0.1 mg/kg to about 20 mg/kg or about 0.1 mg/kg to about 30 mg/kg.

In still other embodiments, the PD-L1 inhibitor antibody can be present at an amount of about: 0.1 mg/kg, 0.5 mg/kg, 1 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, or 50 mg/kg. The PD-L1 inhibitor antibody can be present at an amount of about: 1 mg/kg, 2 mg/kg, 3 mg/kg, 5 mg/kg, 10 mg/kg, 15 mg/kg, 20 mg/kg, 25 mg/kg, or 30 mg/kg. The PD-L1 inhibitor antibody can be present at an amount of about: 3 mg/kg, 10 mg/kg, 20 mg/kg, or 30 mg/kg.

The PD-L1 inhibitor antibody can be present in the combination at an amount of about: 1 mg, 5 mg, 10 mg, 15 mg, 20 mg, 25 mg, 30 mg, 40 mg, 50 mg, 60 mg, 70 mg, 75 mg, 80 mg, 90 mg, 100 mg, 150 mg, or 200 mg. The PD-L1 inhibitor antibody can be present in the combination at an amount of about: 250 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg. The PD-L1 inhibitor antibody can be present in the combination at an amount of about 1000 mg to about 2000 mg. The PD-L1 inhibitor antibody can be present in the combination at an amount of about: 1 mg to about 10 mg, 10 mg to about 20 mg, 25 mg to about 50 mg, 30 mg to about 60 mg, 40 mg to about 50 mg, 50 mg to about 100 mg, 75 mg to about 150 mg, 100 mg to about 200 mg, 200 mg to about 500 mg, 500 mg to about 1000 mg, 1000 mg to about 1200 mg, 1000 mg to about 1500 mg, 1200 mg to about 1500 mg, or 1500 to about 2000 mg.

The PD-L1 inhibitor antibody can be present in the combination in an amount of about 0.1 mg/mL, 0.5 mg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL, 30 mg/mL, 40 mg/mL, 50 mg/mL, 60 mg/mL, 70 mg/mL, 80 mg/mL, 90 mg/mL, 100 mg/mL, 150 mg/mL, 200 mg/mL, 250 mg/mL, 300 mg/mL, 400 mg/mL, or 500 mg/mL. In one embodiment, the PD-L1 inhibitor antibody is present in the combination in an amount of about: 1 mg/mL to about 10 mg/mL, 5 mg/mL to about 10 mg/mL, 5 mg/mL to about 15 mg/mL, 10 mg/mL to about 25 mg/mL; 20 mg/mL to about 30 mg/mL; 25 mg/mL to about 50 mg/mL, or 50 mg/mL to about 100 mg/mL.

In certain instances the therapeutically effective amount of a PD-L1 inhibitor antibody is determined as an amount provided in a package insert provided with the PD-L1 inhibitor antibody. The term package insert refers to instructions customarily included in commercial packages of medicaments approved by the FDA or a similar regulatory agency of a country other than the USA, which contains information about, for example, the usage, dosage, administration, contraindications, and/or warnings concerning the use of such medicaments.

Compounds of formula I as described herein can be provided in amounts that are synergistic with the amount of the PD-L1 inhibitor. The term synergistic refers to a combination described herein (e.g., a compound of formula I and a PD-L1 inhibitor—including coadministration with another active agent such as an anti-cancer agent described herein) or a combination of regimens such as those described herein that is more effective than the additive effects of each individual therapy or regimen.

A synergistic effect of a combination described herein can permit the use of lower dosages of one or more of the components of the combination (e.g., a compound of formula I or a PD-L1 inhibitor). A synergistic effect can permit less frequent administration of at least one of the administered therapies (e.g., a compound of formula I or a PD-L1 inhibitor) to a subject with a disease, disorder, or condition described herein. Such lower dosages and reduced frequency of administration can reduce the toxicity associated with the administration of at least one of the therapies (e.g., a compound of formula I or a PD-L1 inhibitor) to a subject without reducing the efficacy of the treatment. A synergistic effect as described herein avoid or reduce adverse or unwanted side effects associated with the use of any therapy.

Pharmaceutical Compositions

Combinations described herein can be provided as a pharmaceutical composition suitable for administration via any route to a patient described herein including but not limited to: oral, mucosal (e.g., nasal, inhalation, pulmonary, sublingual, vaginal, buccal, or rectal), parenteral (e.g., subcutaneous, intravenous, bolus injection, intramuscular, or intra-arterial), topical (e.g., eye drops or other ophthalmic preparations), transdermal or transcutaneous administration to a patient.

Exemplary of dosage forms include: tablets; caplets; capsules (e.g., gelatin capsules); cachets; lozenges; suppositories; powders; gels; liquid dosage forms suitable for parenteral administration to a patient; and sterile solids (e.g., crystalline or amorphous solids) that can be reconstituted to provide liquid dosage forms suitable for parenteral administration to a patient.

Pharmaceutical compositions and dosage forms described herein typically include one or more excipients. Suitable excipients are well known to those skilled in the art of pharmacy. Whether a particular excipient is suitable for incorporation into a pharmaceutical composition or dosage form depends on a variety of factors such as, for example, the intended route of administration to the patient. Pharmaceutical compositions described herein can include other agents such as stabilizers, lubricants, buffers, and disintegrants that can reduce the rate by which an active ingredient can decompose in a particular formulation.

Pharmaceutical compositions described herein can in certain instances include additional active agents other than those in the combinations described herein (e.g., an anti-cancer agent such as those described herein) in an amount provided herein.

In one embodiment, the compound of formula I is provided in an oral dosage form such as a tablet or capsule. In another embodiment, the compound of formula I is supplied as a powder (e.g., lyophilized powder) that can be resuspended in a liquid suitable for parenteral administration.

PD-L1 inhibitors described herein can be provided in forms convenient to or facilitate their administration to a patient. For example, where the PD-L1 inhibitor is a PD-L1 inhibitor antibody as described herein, the PD-L1 inhibitor can be formulated as a ready to use solution for parenteral administration. In other examples, the PD-L1 inhibitor, including for example a PD-L1 inhibitor antibody, can be formulated as a powder (e.g., lyophilized powder) that can be resuspended in a liquid suitable for parenteral administration. In one embodiment, the combination includes a PD-L1 inhibitor antibody formulated for intravenous administration. In still another embodiment the combination includes a compound of formula I formulated as an oral dosage form (e.g., a tablet or capsule) and a PD-L1 inhibitor formulated for intravenous administration.

Combinations described herein can be provided as controlled release pharmaceutical products, which have a goal of improving drug therapy over that achieved by their non-controlled counterparts. Controlled release formulations can extend activity of the drug, reduce dosage frequency, and increase subject compliance. In addition, controlled release formulations can be used to affect the time of onset of action or other characteristics, such as blood levels of the drug, and can thus affect the occurrence of side (e.g., adverse) effects.

Kits

The combinations and pharmaceutical compositions described herein can be provided as part of a kit. Such kits can, for example, improve patient compliance or improve the accuracy or ease of preparation for administering the combination. The kit includes a compound of formula I where the compound is supplied in a formulation as described herein. The kit also includes a PD-L1 inhibitor as described herein. In some embodiments, the kit includes a PD-L1 inhibitor such as, CA-170 (Curis). In some embodiments, the kit includes a PD-L1 inhibitor antibody, as described herein, such as for example, durvalumab, avelumab, atezolizumab, BMS-936559, STI-A1010, STI-A1011, STI-A1012, STI-A1013, STI-A1014, or STI-A1015. The kit can include a package insert or other information (e.g., prescribing information) useful for administration of the combination to a patient in need thereof, such as a cancer patient described herein.

Kits of the invention can include the combinations described herein (e.g., a compound of formula I and a PD-L1 inhibitor antibody) having the same or different formulation. Each component of a combination described herein in a kit can be supplied in a separate, individual container. Alternatively or additionally, components of the combinations described herein can be supplied in a single container. In such instances, the container can be a container that is ready for administration to a patient in need thereof, such as for example, an IV bag, ampoule, or a syringe. In one embodiment, the compound of formula I in the kit is formulated for oral administration (e.g., a tablet, capsule, or sachet). The PD-L1 inhibitor can be supplied as, for example, a powder (e.g., lyophilized powder) or as a solution for parenteral administration. In certain instances the PD-L1 inhibitor is a PD-L1 inhibitor antibody as described herein formulated for parenteral administration by, for example, intravenous administration.

The contents of kits described herein can be provided in sterile form. The kit and its contents can be provided in a form that is ready for administration to the subject in need. In such instances, the components of the combination of the kit are supplied as a formulation and optionally in an administration device such that administration requires little to no further action by the user. Where kits include administration devices, such devices include devices known and understood by those skilled in the art for routes of administration described herein, such as but not limited to, syringes, pumps, bags, cups, inhalers, droppers, patches, creams, or injectors.

Methods

The combinations, pharmaceutical compositions, and kits described herein are useful for treating diseases, disorders, or alleviating or eliminating the symptoms of diseases and disorders such as, for example, cancer. It is to be understood that the methods described herein pertain to administration of combinations and pharmaceutical compositions described herein, and such combinations and pharmaceutical compositions can be provided in the form of a kit as described herein. Provided herein are methods of treating cancer by administering a therapeutically effective amount of a combination described herein to a patient in need thereof. Also provided herein are methods of managing cancer by administering therapeutically effective amount of a combination described herein to a patient in need thereof.

Combinations useful in the methods described herein include a compound of formula I:

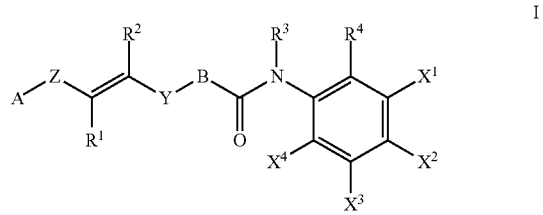

where:

A is a phenyl or heterocyclic group, optionally substituted with 1 to 4 substituents selected from the group consisting of halogen, —OH, —NH$_2$, —NO$_2$, —CN, —COOH, $C_1$-$C_4$ alkyl, $C_1$-$C_4$ alkoxy, $C_1$-$C_4$ aminoalkyl, $C_1$-$C_4$ alkylamino, $C_2$-$C_4$ acyl, $C_2$-$C_4$ acylamino, $C_1$-$C_4$ alkythio, $C_1$-$C_4$ perfluoroalkyl, $C_1$-$C_4$ perfluoroalkyloxy, $C_1$-$C_4$ alkoxycarbonyl, phenyl, and a heterocyclic group;

B is phenyl optionally substituted with 1 to 3 substituents selected from the group consisting of halogen, —OH, —NH$_2$, —NO$_2$, —CN, —COOH, $C_1$-$C_4$ alkyl, $C_1$-$C_4$ alkoxy, $C_1$-$C_4$ aminoalkyl, $C_1$-$C_4$ alkylamino, $C_2$-$C_4$ acyl, $C_2$-$C_4$ acylamino, $C_1$-$C_4$ alkylthio, $C_1$-$C_4$ perfluoroalkyl, $C_1$-$C_4$ perfluoroalkyloxy, $C_1$-$C_4$ alkoxycarbonyl, and phenyl;

Y is a moiety comprising —CO— which is linear and in which the distances between the centroid of ring B (W1), the centroid of ring A (W2) and an oxygen atom as a hydrogen bond acceptor in the moiety Y (W3) are: W1-W2=about 6.0 Å, W1-W3=about 3.0 Å to about 6.0 Å, and W2-W3=about 4.0 Å to about 8.0 Å, respectively;

Z is a bond or $C_1$-$C_4$ alkylene, —O—, —S—, —NH—, —CO—, —CS—, —SO—, or —SO$_2$—;

$R^1$ and $R^2$ are independently hydrogen or $C_1$-$C_4$ alkyl;

$R^3$ is hydrogen or $C_1$-$C_4$ alkyl;

$R^4$ is hydrogen or —NH$_2$; and one of $X^1$, $X^2$, $X^3$, or $X^4$ is halogen, —OH, —NH$_2$, —NO$_2$, —CN, —COOH, $C_1$-$C_4$ alkyl, $C_1$-$C_4$ alkoxy, $C_1$-$C_4$ aminoalkyl, $C_1$-$C_4$ alkylamino, $C_2$-$C_4$ acyl, $C_2$-$C_4$ acylamino, $C_1$-$C_4$ alkylthio, $C_1$-$C_4$ perfluoroalkyl, $C_1$-$C_4$ perfluoroalkyloxy, or $C_1$-$C_4$ alkoxycarbonyl optionally substituted with halogen or $C_1$-$C_4$ alkyl, while the others of $X^1$, $X^2$, $X^3$, or $X^4$ are independently hydrogen, provided, however, that when $R^4$ is hydrogen, one of $X^1$, $X^2$, $X^3$, or $X^4$ is —NH$_2$, an aminoalkyl group or an alkylamino group.

Compounds of formula I useful in the methods described herein include compounds as substantially described hereinabove. In certain instances, the compound of formula I used to treat cancer in the methods provided herein includes compounds where $R^1$, $R^2$, and $R^3$ are hydrogen. In certain instances Y is —C(O)NH—CH$_2$—. In certain instances, $R^3$ can be $C_1$-$C_4$ alkyl as described above. A of formula I can be a 5 to 10-membered heterocyclic moiety. In particular, and as described above, useful embodiments of the compound of formula I include compounds where A is N-heterocycle, such as for example, a 5 or 6 membered heterocyclic moiety. A can be, in certain instances, a pyridinyl.

The compound of formula I useful in the methods described herein can be a compound where $R^4$ is —NH$_2$ amount of 0.1 mg/kg, 0.3 mg/kg, 1 mg/kg, 2 mg/kg, 3 mg/kg, 5 mg/kg, 10 mg/kg, or 20 mg/kg and at least of $X^1$, $X^2$, $X^3$, or $X^4$ is —$NH_2$ or halogen. In certain instances, the compound of formula I for use in the methods described herein includes compounds where $R^4$ is —$NH_2$ and at least one of $X^1$, $X^2$, $X^3$, or $X^4$ is halogen (e.g., —F). In one embodiment, the compound of formula I is a compound of formula Ia as set forth above.

The PD-L1 inhibitors for use in the methods described herein are those PD-L1 inhibitors described herein. For example, the PD-L1 inhibitor can be a small molecule compound, a nucleic acid, a polypeptide, an antibody, a peptibody, a diabody, a minibody, a single-chain variable fragment (ScFv), or functional fragment or variant thereof. In other examples, the PD-L1 inhibitor can be a PD-L1 inhibitor antibody as set forth above. In one instance, the PD-L1 inhibitor antibody for use in the methods described herein is durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

It should be understood that the compound of formula I and the PD-L1 inhibitor constituting the combination for use in such methods includes each therapy in amounts as described herein and are administered as described herein. For example, the compound of formula I can be present in a combination administered to patient in need thereof at an amount of about 5 mg to about 50 mg or about 5 mg to about 100 mg. As another example, the PD-L1 inhibitor can be a PD-L1 inhibitor antibody present in an amount of, for example, about 0.1 mg/kg to about 10 mg/kg, about 0.1 mg/kg to about 20 mg/kg, or about 0.1 mg/kg to about 30 mg/kg. In another example, the PD-L1 inhibitor is a PD-L1 inhibitor antibody present in an amount of, for example, about 1000 mg to 2000 mg. These amounts are merely exemplary and do not limit in any way the amount of each therapy that can be present in the combination as described herein.

It is also understood that the combination for use in the methods described herein can be provided as a kit as set forth above. Such kits include each component of the combination as described herein and optionally additional kit components including, for example, containers and administration devices such as those described above.

The cancer can be a solid tumor. The cancer can be a hematological cancer. In certain instances, the cancer is a solid tumor selected from the group consisting of squamous cell carcinoma, non-squamous cell carcinoma, non-small cell lung cancer (NSCLC), small cell lung cancer, melanoma, hepatocellular carcinoma, renal cell carcinoma, ovarian cancer, head and neck cancer, urothelial cancer, breast cancer, prostate cancer, glioblastoma, colorectal cancer, pancreatic cancer, lymphoma, leiomyosarcoma, liposarcoma, synovial sarcoma, or malignant peripheral sheath tumor (MPNST).

In particular embodiments, the cancer is a solid tumor selected from non-small cell lung cancer (NSCLC), hepatocellular carcinoma, melanoma, ovarian cancer, breast cancer, pancreatic cancer, renal cell carcinoma, or colorectal cancer. The cancer can be non-small cell lung cancer (NSCLC). The cancer can be hepatocellular carcinoma. The cancer can be melanoma. The cancer can be ovarian cancer. The cancer can be breast cancer. The cancer can be pancreatic cancer. The cancer can be renal cell carcinoma. The cancer can be colorectal cancer.

Provided herein are methods of treating NSCLC by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In some embodiments, the NSCLC is Stage IIA or Stage IIB. The NSCLC can be a Stage IIIA or Stage IIIB cancer. The NSCLC can be a Stage IV cancer. Staging of cancers as described herein is described by the American Joint Committee on Cancer TNM classification of malignant tumors cancer staging notation as is well understood in the art. Those of skill in the art will readily understand other staging classification systems are available and applicable to the methods described herein. In certain instances, the method is a method of treating Stage IIIA or IIIB NSCLC by administering a combination described herein that includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In yet another aspect is a method of treating a Stage IV NSCLC by administering a combination described herein that includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

Further provided herein are methods of treating hepatocellular carcinoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In some embodiments the hepatocellular carcinoma is a Stage II cancer. In another embodiment, the hepatocellular carcinoma is a Stage IIIA, Stage IIIB, or Stage IIIC cancer. In still another embodiment, the hepatocellular carcinoma is a Stage IVA or Stage IVB cancer. In one aspect the method is a method of treating Stage III (e.g., Stage IIIA, IIIB, or IIIC) hepatocellular carcinoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In still another aspect is a method of treating Stage IV (e.g., Stage IVA or Stage IVB) hepatocellular carcinoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

Still further provided herein are methods of treating melanoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In some embodiments the melanoma is a Stage IIA, IIB, or IIC cancer. In another embodiment, the melanoma is a Stage IIIA, Stage IIIB, or Stage IIIC cancer. In still another embodiment, the melanoma is a Stage IV cancer. In one aspect the method is a method of treating Stage II (e.g., Stage IIA, IIB, or IIC) melanoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In one aspect the method is a method of treating Stage III (e.g., Stage IIIA, IIIB, or IIIC) melanoma by administering a therapeutically effective amount of a combination described herein where the combination includes a compound of formula I and a PD-L1 inhibitor antibody selected from durvalumab, avelumab, atezolizumab, or BMS-936559, or STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In still another aspect is a method of treating Stage IV melanoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

In yet another aspect are methods of treating ovarian cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In some embodiments the ovarian cancer is a Stage I cancer as defined by the FIGO Ovarian Cancer Staging standards. The ovarian cancer can be a Stage IA, IB, or IC (e.g., IC1, IC2, or IC3) cancer. In another embodiment, the ovarian cancer is a Stage II cancer. The ovarian cancer can be a Stage IIA or IIB cancer. In one aspect the method is a method of treating Stage I (e.g., Stage IA, IB, IC1, IC2, or IC3) ovarian cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In another aspect the method is a method of treating Stage II (e.g., Stage IIA or IIB) ovarian cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

Also provided herein are methods of treating breast cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. The breast cancer can be HER2 negative breast cancer. The breast cancer can be a HER2 positive breast cancer. The breast cancer can be triple-negative breast cancer. In some embodiments the breast cancer is a Stage IA or Stage IB cancer. In another embodiment, the breast cancer is a Stage IIA or Stage IIB cancer. In still another embodiment, the breast cancer is a Stage IIIA, Stage IIIB, or Stage IIIC cancer. In yet another embodiment, the breast cancer is a Stage IV cancer. In one aspect the method is a method of treating Stage I (e.g., Stage IA or IB) breast cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In another aspect the method is a method of treating Stage II (e.g., Stage IIA or IIB) breast cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015 (Sorrento Therapeutics). In another example, the PD-L1 inhibitor antibody is durvalumab, avelumab, atezolizumab, or BMS-936559. In still another aspect the method is a method of treating Stage III (e.g., Stage IIIA, IIIB, or IIIC) breast cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In yet another aspect is a method of treating Stage IV breast cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

Methods of treating pancreatic cancer are provided herein. In one aspect the method includes treating pancreatic cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015 (Sorrento Therapeutics). In another example, the PD-L1 inhibitor antibody is durvalumab, avelumab, atezolizumab, or BMS-936559. In some embodiments, the pancreatic cancer is locally advanced, surgically resected or unresected pancreatic cancer or metastatic pancreatic adenocarcinoma. In some embodiments the pancreatic cancer is a Stage IA or Stage IB cancer. In another embodiment, the pancreatic cancer is a Stage IIA or Stage IIB cancer. In still another embodiment, the pancreatic cancer is a Stage III cancer. In yet another embodiment, the pancreatic cancer is a Stage IV cancer. In one aspect the method is a method of treating Stage I (e.g., Stage IA or IB) pancreatic cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In another aspect the method is a method of treating Stage II (e.g., Stage IIA or IIB) pancreatic cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In still another aspect the method is a method of treating Stage III pancreatic cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In yet another aspect is a method of treating Stage IV pancreatic cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

Further provided herein are methods of treating renal cell carcinoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In some embodiments the renal cell carcinoma is a Stage I cancer. In another embodiment, the renal cell carcinoma is a Stage II cancer. In still another embodiment, the renal cell carcinoma is a Stage III cancer. In yet another embodiment, the renal cell carcinoma is a Stage IV cancer. In one aspect the method is a method of treating Stage I renal cell carcinoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In another aspect the method is a method of treating Stage II renal cell carcinoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In still another aspect the method is a method of treating Stage III renal cell carcinoma by administering a therapeutically effective amount of a combination described herein where the combination includes a compound of formula I and a PD-L1 inhibitor antibody selected from durvalumab, avelumab, atezolizumab, or BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In yet another aspect is a method of treating Stage IV renal cell carcinoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

Methods of treating colorectal cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015 (Sorrento Therapeutics) are also provided herein. In another example, the PD-L1 inhibitor antibody is durvalumab, avelumab, atezolizumab, or BMS-936559. In some embodiments the colorectal cancer is a Stage I cancer. In another embodiment, the colorectal cancer is a Stage IIA, Stage IIB, or Stage IIC cancer. In still another embodiment, the colorectal cancer is a Stage IIIA, Stage IIIB, or Stage IIIC cancer. In yet another embodiment, the colorectal cancer is a Stage IVA or Stage IVB cancer. In certain instances the colorectal cancer is further characterized by the grade of the cancer. The colorectal cancer can be a Grade 1, Grade 2, Grade 3, or Grade 4 cancer in any of the stages provided herein. In one aspect the method is a method of treating Stage I colorectal cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In another aspect the method is a method of treating Stage II (e.g., Stage IIA, IIB, or IIC) colorectal cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In still another aspect the method is a method of treating Stage III (e.g., Stage IIIA, IIIB, or IIIC) colorectal cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In yet another aspect is a method of treating Stage IV (e.g., Stage IVA or IVB) colorectal cancer by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

In other embodiments, the cancer is a hematological cancer selected from lymphoma, Non-Hodgkin's lymphoma (NHL), Hodgkin's Lymphoma, Reed-Sternberg disease, multiple myeloma (MM), acute myelogenous leukemia (AML), chronic myelogenous leukemia (CML), acute lymphocytic leukemia, (ALL), or chronic lymphocytic leukemia (CLL). In certain embodiments, the cancer is Hodgkin's Lymphoma or Reed-Sternberg disease.

In certain embodiments, the methods of treating cancer include methods of treating NHL by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. The NHL can be characterized by its stage according to, for example, the Ann Arbor staging system. The NHL can be indolent NHL (e.g., follicular lymphoma (FL); lymphoplasmacytic lymphoma (LL); marginal zone lymphoma (MZL) or Primary cutaneous anaplastic large cell lymphoma) or aggressive NHL (e.g., Diffuse large B-cell lymphoma (DLBCL); Follicular large cell lymphoma stage III; anaplastic large cell lymphoma; extranodal NK-/T-cell lymphoma; lymphomatoid granulmatosis; angioimmunoblastic T-cell lymphoma; peripheral T-cell lymphoma; intravascular large B-cell lymphoma; Burkitt lymphoma; lymphoblastic lymphoma; adult T-cell leukemia/lymphoma; or mantle cell lymphoma). In some embodiments the NHL is a Stage I (e.g., Stage I(I) (thymus) or Stage I(E) (lymph system)) cancer. In another embodiment, the NHL is a Stage II (e.g., Stage II(I) (lymph nodes) or Stage II(E) (nearby organs)) cancer. In still another embodiment, the NHL is a Stage III (e.g., Stage III(I) (lymph nodes), Stage III(E) (nearby organs), Stage III(S) (spleen), or Stage III(ES) (nearby organs and spleen)) cancer. In yet another embodiment, the NHL is a Stage IV cancer. In one aspect the method is a method of treating Stage I (e.g., Stage I(I) or I(E)) NHL by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In another aspect the method is a method of treating Stage II (e.g., Stage II(I) or II(E)) NHL by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In still another aspect the method is a method of treating Stage III (e.g., Stage III(I), III(E), III(S), or III(ES)) NHL by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In yet another aspect is a method of treating Stage IV NHL by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

In another aspect are methods of treating Hodgkin's Lymphoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. The Hodgkin's lymphoma can be classical or nodular lymphocyte-predominant. In some embodiments the Hodgkin's Lymphoma includes Reed-Sternberg cells and can cause Reed-Sternberg disease. In some embodiments the Hodgkin's Lymphoma is a Stage I cancer. In another embodiment, the Hodgkin's Lymphoma is a Stage II cancer. In still another embodiment, the Hodgkin's Lymphoma is a Stage III cancer. In yet another embodiment, the Hodgkin's Lymphoma is a Stage IV cancer. In one aspect the method is a method of treating Stage I Hodgkin's Lymphoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In another aspect the method is a method of treating Stage II Hodgkin's Lymphoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In still another aspect the method is a method of treating Stage III Hodgkin's Lymphoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In yet another aspect is a method of treating Stage IV Hodgkin's Lymphoma by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

In still another aspect are methods of treating chronic lymphocytic leukemia (CLL) by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. CLL can be staged according to the Rai system or Binet System. For example, in one embodiment, the CLL is a Rai Stage I cancer. In another embodiment the CLL is a Rai Stage II cancer. In still another embodiment the CLL is a Rai Stage III cancer. In yet another embodiment the CLL is a Rai Stage IV cancer. In still yet another embodiment, the CLL is a Binet Stage A cancer. The CLL can be a Binet Stage B cancer. The CLL can be a Binet Stage C cancer. In one aspect the method is a method of treating Rai Stage I CLL by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In one aspect the method is a method of treating Rai Stage II CLL by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In one aspect the method is a method of treating Rai Stage III CLL by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In one aspect the method is a method of treating Rai Stage IV CLL by administering a therapeutically effective amount of a combination described herein where the combination includes a compound of formula I and a PD-L1 inhibitor antibody selected from durvalumab, avelumab, atezolizumab, BMS-936559, or STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In one aspect the method is a method of treating Binet Stage A CLL by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In one aspect the method is a method of treating Binet Stage B CLL by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In one aspect the method is a method of treating Binet Stage C CLL by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

In still yet another aspect are methods of treating acute lymphoblastic leukemia (ALL) by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. The ALL can be characterized according to the World Health Organization (WHO) classification. The ALL can be T-cell lymphoblastic leukemia. The ALL can be B-cell lymphoblastic leukemia. The ALL can be B-cell lymphoblastic leukemia having a recurrent genetic abnormality selected from:
  B lymphoblastic leukemia/lymphoma with t(9;22)(q34; q11.2), BCR-ABL1;
  B lymphoblastic leukemia/lymphoma with t(v;11q23); MLL rearranged;
  B lymphoblastic leukemia/lymphoma with t(12;21)(p13; q22) TEL-AML1 (ETV6-RUNX1);
  B lymphoblastic leukemia/lymphoma with hyperdiploidy;
  B lymphoblastic leukemia/lymphoma with hypodiploidy;
  B lymphoblastic leukemia/lymphoma with t(5; 14)(q31; q32) IL3-IGH; or
  B lymphoblastic leukemia/lymphoma with t(1;19)(q23; p13.3) TCF3-PBX1.

In yet another aspect are methods of treating chronic myelogenous leukemia (CML) by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. The CML can be characterized by the phase of the disease. In one embodiment, the CML is in chronic phase (e.g., the patient has about less than 10% blasts in their blood or bone marrow). In another embodiment, the CML is in accelerated phase (e.g., the patient has (1) more than 10% blasts but fewer than 20% blasts in their blood or bone marrow; (2) basophil counts comprising at least about 20% of the white blood cell (WBC) count; (3) high WBC counts; (4) high or low platelet counts; or (5) chromosomal changes in the leukemia cells). In yet another embodiment, the CML is in blast phase (e.g., the patient has greater than 20% blasts in their blood or bone marrow). In one aspect the method is a method of treating CML in the chronic phase by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In another aspect the method is a method of treating CML in the accelerated phase by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In still another aspect the method is a method of treating CML in the blast phase by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

Also provided herein are methods of treating AML by administering a therapeutically effective amount of a combination described herein where the combination includes a compound of formula I and a PD-L1 inhibitor antibody selected from durvalumab, avelumab, atezolizumab, BMS-936559, STI-A1010, STI-A1011, STI-A1012, STI-A1013, STI-A1014, or STI-A1015. The AML can be characterized by, for example, the WHO classification system. In one embodiment, the AML is characterized by having certain genetic abnormalities including those provided below:

AML with a translocation between chromosomes 8 and 21;

AML with a translocation or inversion in chromosome 16;

AML with a translocation between chromosomes 9 and 11;

APL (M3) with a translocation between chromosomes 15 and 17;

AML with a translocation between chromosomes 6 and 9;

AML with a translocation or inversion in chromosome 3; or

AML (megakaryoblastic) with a translocation between chromosomes 1 and 22.

The AML can be characterized as having myelodysplasia-related changes. The AML can be characterized as being related to previous anti-cancer therapy (e.g., chemotherapy or radiotherapy). The AML can be characterized as AML that is considered to not fall in the WHO groups above and includes, for example:

AML with minimal differentiation (M0);
AML without maturation (M1);
AML with maturation (M2);
Acute myelomonocytic leukemia (M4);
Acute monocytic leukemia (M5);
Acute erythroid leukemia (M6);
Acute megakaryoblastic leukemia (M7);
Acute basophilic leukemia; or
Acute panmyelosis with fibrosis.

The combinations described herein can be administered to a cancer patient at any time following diagnosis. For example, the cancer patient can be treatment naïve (e.g., has not received a cancer therapy for the diagnosed cancer). The cancer patient can be treatment naïve for one cancer but can be diagnosed with one or more other cancers resulting from, for example, metastasis or malignancy. The cancer patient can be immune checkpoint naïve for one or more cancers. The cancer patient can have a cancer that is refractory. In certain instances, the combinations described herein are administered as a first line therapy (e.g., the first therapy administered to a treatment naïve cancer patient) to a patient in need thereof.

However, cancer morbidity and mortality is often associated with ineffective therapy or a cancer gaining resistant to or becoming refractory to one or more cancer therapies. The combinations described herein can, therefore, be administered to patients in need thereof as a second, third, fourth, fifth, sixth, or more line of treatment. The combinations described herein can be administered to a cancer patient who has been treated with at least one anti-cancer therapy or anti-cancer agent. In certain instances the patient has received at least one anti-cancer therapy including, for example, chemotherapy, radiotherapy, surgery, targeted therapy, immunotherapy, or a combination thereof. The patient can have a cancer that is resistant/refractory to treatment with at least one anti-cancer agent. The methods of treating cancers herein include treating subjects who have been treated with a PD-1 checkpoint inhibitor and have experienced no response to treatment, or a partial response, or stable disease, but then develop resistance to treatment with progression of disease or who have experienced a complete response to treatment, but then develop resistance to treatment with progression of disease (as defined by RECIST or other criteria). Resistance is defined as disease progression during treatment or a lack of response to treatment. Such PD-1 inhibitor antibody treatment failures can be treated with PD-L1 in combination with an HDAC inhibitor, such as, without limitation, HBI-8000 or an HDAC inhibitor that inhibits cancer-associated Class I HDAC selected from one or more of HDAC1, HDAC2, or HDAC3. In some instances the HDAC inhibitor also inhibits Class IIb HDAC1. HBI-8000 is reported to inhibit HDAC 1, 2, 3, and 10 at low nanomolar concentrations (see Zhi-Qiang Ning et al., *Cancer Chemother Pharmacol* (2012) 69:901-909). It also has activity at HDAC 8 and 11. Ning et al. also report that HBI-8000 is more active than Entinostat at HDAC 1, 2, 3, 8, 10 and 11. Further HBI-8000 has a favorable pharmacokinetic profile and safety profile that allows for continuous dosing-oral administration pK ($t_{1/2}$ about 17 hours).

Response Criteria

RECIST:

RECIST is a set of established criteria or standards, internationally recognized for evaluating patient response, stability and progression in clinical trials and in the clinical practice. Originally published in 2000, and revised in 2009 (Eisenhauer E A, et al.; New response criteria in solid tumours: revised RECIST guideline (version 1.1); *Eur J Cancer* 2009; 45:228-47), as a joint effort of the European Organization for Research and Treatment of Cancer, the National Cancer Institute of the United States and the National Cancer Institute of Canada Clinical Trials Group, RECIST has traditionally been utilized in the evaluation of response to chemotherapy.

Evaluation of Target Lesions:

Complete Response (CR): Disappearance of all target lesions; Partial Response (PR): At least a 30% decrease in the sum of the LD (longest diameter) of target lesions, taking as reference the baseline sum LD; Stable Disease (SD):

Neither sufficient shrinkage to qualify for PR nor sufficient increase to qualify for PD, taking as reference the smallest sum LD since the treatment started; Progressive Disease (PD): At least a 20% increase in the sum of the LD of target lesions, taking as reference the smallest sum LD recorded since the treatment started or the appearance of one or more new lesions.

Evaluation of Non-Target Lesions:

Complete Response (CR): Disappearance of all non-target lesions and normalization of tumor marker level; Incomplete Response/Stable Disease (SD): Persistence of one or more non-target lesion(s) or/and maintenance of tumor marker level above the normal limits; Progressive Disease (PD): Appearance of one or more new lesions and/or unequivocal progression of existing non-target lesions.

Other Response Criteria

Other response criteria include the Immune-Related Response Criteria or iRECIST, as defined by Wolchok et al., in 2009 (Wolchok J D, et al.; Guidelines for the Evaluation of Immune Therapy Activity in Solid Tumors: Immune-Related Response Criteria. Clin Cancer Res 2009; 15(23): 7412-20) and the revised International Working Group Response Criteria (Cheson B D et al., Revised response criteria for malignant lymphoma. J. Clin. Oncol. 2007; 25:579-586).

The methods of treating cancer include methods for inhibiting cell growth by administering a therapeutically effective amount of a combination described herein where the combination includes a compound of formula I and a PD-L1 inhibitor described herein. In one example the PD-L1 inhibitor is a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559.

Also provided herein are methods of inhibiting metastasis of a cancer in a patient in need thereby by administering a therapeutically effective amount of a combination described herein where the combination includes a compound of formula I and a PD-L1 inhibitor described herein. In one example the PD-L1 inhibitor is a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In some embodiments, metastasis is inhibited by at least about 5%, 10%, 20%, 30%, 40%, 50%, 60%, 70%, 80%, 90%, or 100%.

In another aspect is a method of reducing pre-existing tumor metastasis in a cancer patient in need thereof by administering a therapeutically effective amount of a combination described herein where the combination includes a compound of formula I and a PD-L1 inhibitor described herein. In one example the PD-L1 inhibitor is a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In some embodiments, pre-existing tumor metastasis is reduced by at least about 5%, 10%, 20%, 30%, 40%, 50%, 60%, 70%, 80%, 90%, or 100%.

In still another aspect the methods of treating cancer also provide for methods for reducing tumor burden in an individual by administering a therapeutically effective amount of a combination described herein where the combination includes a compound of formula I and a PD-L1 inhibitor described herein. In one example the PD-L1 inhibitor is a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In some embodiments, tumor burden is reduced by at least about 5%, 10%, 20%, 30%, 40%, 50%, 60%, 70%, 80%, 90%, or 100%.

In another aspect the methods of treating cancer also provide for methods for reducing tumor burden in an individual by administering a therapeutically effective amount of a combination described herein where the combination includes a compound of formula I and a PD-L1 inhibitor described herein. In one example the PD-L1 inhibitor is a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In some embodiments, tumor burden is reduced by at least about 5%, 10%, 20%, 30%, 40%, 50%, 60%, 70%, 80%, 90%, or 100%.

The methods of treating cancer described herein also provide for methods for increasing or otherwise prolonging time to disease progression of certain stages (including advanced stages of cancer such as Stage III and IV cancer described herein). Time to disease progression can be prolonged in a patient by administering a therapeutically effective amount of a combination described herein where the combination includes a compound of formula I and a PD-L1 inhibitor described herein. In one example the PD-L1 inhibitor is a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In some embodiments, the increase is a comparison between the time to disease progression without treatment and with treatment with a combination described herein. In some embodiments, the methods described herein prolong the time to disease progression by at least 1 week, 2 weeks, 3 weeks, 4 weeks, 1 month, 2 months, 3 months, 4 months, 5 months, 6 months, 7 months, 8 months, 9 months, 10 months, 11 months, 1 year, or more, including values therein.

The methods of treating cancer described herein also provide for methods for increasing or otherwise prolonging survival (including overall survival) of patients diagnosed with cancer as described herein. Patient survival can be prolonged by administering a therapeutically effective amount of a combination described herein where the combination includes a compound of formula I and a PD-L1 inhibitor described herein. In one example the PD-L1 inhibitor is a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In some embodiments, the increase is a comparison between the survival without treatment and with treatment with a combination as described herein. In some embodiments, the methods described herein prolong survival by at least 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, or more, including values therein.

The methods of treating cancer described herein also provide for methods for increasing progression-free survival of patients diagnosed with cancer as described herein. Patient progression-free survival can be prolonged by administering a therapeutically effective amount of a combination described herein where the combination includes a compound of formula I and a PD-L1 inhibitor described herein. In one example the PD-L1 inhibitor is a PD-L1 inhibitor antibody selected from durvalumab, avelumab, atezolizumab, BMS-936559, STI-A1010, STI-A1011, STI-A1012, STI-A1013, STI-A1014, or STI-A1015. In another example, the PD-L1 inhibitor antibody is durvalumab, avelumab, atezolizumab, or BMS-936559. In some embodiments, the increase is a comparison between the progression-free survival without treatment and with treatment with a combination as described herein. In some embodiments, the methods described herein increase progression-free survival by at least 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, or more, including values therein.

Also provided herein are methods of reducing a level of myeloid-derived suppressor cells (MDSC) in a patient in need thereof by administering an effective amount of a combination described herein where the combination includes a compound of formula I and a PD-L1 inhibitor described herein. In one example the PD-L1 inhibitor is a PD-L1 inhibitor antibody selected from durvalumab, avelumab, atezolizumab, BMS-936559, STI-A1010, STI-A1011, STI-A1012, STI-A1013, STI-A1014, or STI-A1015 (Sorrento Therapeutics) compared to administration of a compound of formula I or a PD-L1 inhibitor alone. In another example, the PD-L1 inhibitor antibody is durvalumab, avelumab, atezolizumab, or BMS-936559. The reduction of MDSC can benefit the treatment of a cancer described herein. The level of MDSC in a human patient can be measured before, during, and after administration of a combination described herein. In some embodiments, it can be useful to compare pre- and post-administration amounts of MDSC in the patient. A reduction in the amount, level, or number of MDSC following administration can indicate effectiveness of the combination in, for example, treating a cancer described herein. MDSC levels can be monitored over the course of a treatment or regimen described herein with a combination described herein. In such instances, the determination of MDSC levels at various points during the course of administration can indicate the effectiveness of the regimen.

Methods of reducing the percentage or level of Treg cells in a patient in need thereof are also provided herein. Such methods include administering an effective amount of a combination described herein where the combination includes a compound of formula I and a PD-L1 inhibitor described herein. In one example the PD-L1 inhibitor is a PD-L1 inhibitor antibody selected from durvalumab, avelumab, atezolizumab, BMS-936559, STI-A1010, STI-A1011, STI-A1012, STI-A1013, STI-A1014, or STI-A1015 to the patient, wherein the administration decreases the percentage or level of Treg cells in the patient compared to the level prior to the administration. In another example, the PD-L1 inhibitor antibody is durvalumab, avelumab, atezolizumab, or BMS-936559. The reduction of Treg cells can benefit the treatment of a cancer described herein. The level of Treg cells in a human patient can be measured before, during, and after administration of a combination described herein. In some embodiments, it can be useful to compare pre- and post-administration amounts of Treg cells in the patient. A reduction in the amount, level, or number of Treg cells following administration can indicate effectiveness of the combination in, for example, treating a cancer described herein. Treg cell levels can be monitored over the course of a treatment or regimen described herein with a combination described herein. In such instances, the determination of Treg cell levels at various points during the course of administration can indicate the effectiveness of the regimen.

The combinations described herein can be useful in methods of enhancing activity of natural killer (NK) cells. The combinations described herein can also be useful in methods of enhancing activity of cytotoxic T-cells. The methods of enhancing include contacting a NK cell or cytotoxic T-cell with a combination described herein where the combination enhances the activity of the NK cell or cytotoxic T-cell relative to its activity prior to the contact. In some embodiments, the enhanced activity of the NK cell or cytotoxic T-cell is in a cancer patient who has been administered a combination as described herein.

The combinations described herein can also enhance antibody-dependent cell-mediated cytotoxicity in a cancer patient upon administration of a combination as described herein.

The combinations described herein can include administration of each therapy (e.g., a compound of formula I and a PD-L1 inhibitor), where the administration is performed simultaneously or sequentially (in either order). In one embodiment, the compound of formula I and the PD-L1 inhibitor are administered simultaneously (e.g., within at least 1 to 5 min of each other). In another embodiment, the compound of formula I and the PD-L1 inhibitor are administered sequentially (e.g., within at least 10 min, 15 min, 30 min, 1 h, 2 h, 5 h, 10 h, 12 h, 1 day, 2 days, 5 days, 7 days, 14 days, or 21 days of each other).

In one example a compound of formula I is administered concurrently with a PD-L1 inhibitor antibody selected from durvalumab, avelumab, atezolizumab, BMS-936559, or STI-A1010, STI-A1011, STI-A1012, STI-A1013, STI-A1014, or STI-A1015. In another example, a compound of formula I can be administered prior to the administration of durvalumab. In another example, a compound of formula I can be administered prior to the administration of avelumab. In another example, a compound of formula I can be administered prior to the administration of atezolizumab. In another example, a compound of formula I can be administered prior to the administration of BMS-936559. In yet another example, a compound of formula I can be administered prior to the administration of STI-A1010, STI-A1011, STI-A1012, STI-A1013, STI-A1014, or STI-A1015. In another example, a compound of formula I can be administered after the administration of durvalumab. In another example, a compound of formula I can be administered after the administration of avelumab. In another example, a compound of formula I can be administered after the administration of atezolizumab. In another example, a compound of formula I can be administered after the administration of BMS-936559. In yet another example, a compound of formula I can be administered after the administration of STI-A1010, STI-A1011, STI-A1012, STI-A1013, STI-A1014, or STI-A1015.

The compound of formula I can be administered, for example, once a day (QD), twice daily (BID), once a week (QW), twice weekly (BIW), three times a week (TIW), or monthly (QM) regularly on a continuous base or intermittent base such as BIW for 3 months then resume a month later. For example, the compound of formula I can be administered BID. The compound of formula I can be administered TIW. In certain instances, the compound of formula I is administered 2 to 3 times a week. In another embodiment, the compound of formula I is administered QD. The compound can be administered QD for about: 1 day to about 7 days, 1 day to about 14 days, 1 day to about 21 days, 1 day to about 28 days, or daily until disease progression or unacceptable toxicity. The administration of a compound of formula I can, in part, depend upon the tolerance of the patient where greater tolerance can allow greater or more frequent administration. Alternatively, where a patient shows poor tolerance to a compound of formula I, a less amount of the compound or a less frequent dosing can be performed. Compounds of formula I can be administered in any regimen as described herein.

For example, a compound of formula I can be administered at an amount of about: 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, 80 mg, 85 mg, 90 mg, 100 mg, 125 mg, 150 mg, 175 mg, or 200 mg, QD. For example, a compound of formula I can be administered at an amount of about: 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, 80 mg, 85 mg, 90 mg, 100 mg, 125 mg, 150 mg, 175 mg, or 200 mg, BIW. For example, a compound of formula I can be administered at an amount of about: 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, 80 mg, 85 mg, 90 mg, 100 mg, 125 mg, 150 mg, 175 mg, or 200 mg, TIW. For example, a compound of formula I can be administered at an amount of about: 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, 80 mg, 85 mg, 90 mg, 100 mg, 125 mg, 150 mg, 175 mg, or 200 mg, QW. For example, a compound of formula I can be administered at an amount of about: 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, 80 mg, 85 mg, 90 mg, 100 mg, 125 mg, 150 mg, 175 mg, or 200 mg, Q2W. For example, a compound of formula I can be administered at an amount of about 5 mg or about 10 mg, QD. For example, a compound of formula I can be administered at an amount of about 5 mg or about 10 mg, BIW. For example, a compound of formula I can be administered at an amount of about 5 mg or about 10 mg, TIW. For example, a compound of formula I can be administered at an amount of about 5 mg or about 10 mg, QW. For example, a compound of formula I can be administered at an amount of about 5 mg or about 10 mg, Q2W. Administration of a compound of formula I can be continuous. Administration of a compound of formula I can be intermittent.

For example, a compound of formula I can be administered at an amount of about: 1 mg to about 10 mg, 1 mg to about 25 mg, 1 mg to about 50 mg, 5 mg to about 10 mg, 5 mg to about 25 mg, 5 mg to about 50 mg, 10 mg to about 25 mg, 10 mg to about 50 mg, 50 mg to about 100 mg, or 100 mg to about 200 mg, QD. For example, a compound of formula I can be administered at an amount of about: 1 mg to about 10 mg, 1 mg to about 25 mg, 1 mg to about 50 mg, 5 mg to about 10 mg, 5 mg to about 25 mg, 5 mg to about 50 mg, 10 mg to about 25 mg, 10 mg to about 50 mg, 50 mg to about 100 mg, or 100 mg to about 200 mg, BIW. For example, a compound of formula I can be administered at an amount of about: 1 mg to about 10 mg, 1 mg to about 25 mg, 1 mg to about 50 mg, 5 mg to about 10 mg, 5 mg to about 25 mg, 5 mg to about 50 mg, 10 mg to about 25 mg, 10 mg to about 50 mg, 50 mg to about 100 mg, or 100 mg to about 200 mg, TIW. For example, a compound of formula I can be administered at an amount of about: 1 mg to about 10 mg, 1 mg to about 25 mg, 1 mg to about 50 mg, 5 mg to about 10 mg, 5 mg to about 25 mg, 5 mg to about 50 mg, 10 mg to about 25 mg, 10 mg to about 50 mg, 50 mg to about 100 mg, or 100 mg to about 200 mg, QW. For example, a compound of formula I can be administered at an amount of about: 1 mg to about 10 mg, 1 mg to about 25 mg, 1 mg to about 50 mg, 5 mg to about 10 mg, 5 mg to about 25 mg, 5 mg to about 50 mg, 10 mg to about 25 mg, 10 mg to about 50 mg, 50 mg to about 100 mg, or 100 mg to about 200 mg, Q2W. Administration of a compound of formula I can be continuous. Administration of a compound of formula I can be intermittent.

For example, a compound of formula I can be administered at an amount of about: 0.0001 mg/kg to about 200 mg/kg, 0.001 mg/kg to about 200 mg/kg, 0.01 mg/kg to about 200 mg/kg, 0.01 mg/kg to about 150 mg/kg, 0.01 mg/kg to about 100 mg/kg, 0.01 mg/kg to about 50 mg/kg, 0.01 mg/kg to about 25 mg/kg, 0.01 mg/kg to about 10 mg/kg, or 0.01 mg/kg to about 5 mg/kg, 0.05 mg/kg to about 200 mg/kg, 0.05 mg/kg to about 150 mg/kg, 0.05 mg/kg to about 100 mg/kg, 0.05 mg/kg to about 50 mg/kg, 0.05 mg/kg to about 25 mg/kg, 0.05 mg/kg to about 10 mg/kg, or 0.05 mg/kg to about 5 mg/kg, 0.5 mg/kg to about 200 mg/kg, 0.5 mg/kg to about 150 mg/kg, 0.5 mg/kg to about 100 mg/kg, 0.5 mg/kg to about 50 mg/kg, 0.5 mg/kg to about 25 mg/kg, 0.5 mg/kg to about 10 mg/kg, or 0.5 mg/kg to about 5 mg/kg, QD. For example, a compound of formula I can be administered at an amount of about: 0.0001 mg/kg to about 200 mg/kg, 0.001 mg/kg to about 200 mg/kg, 0.5 mg/kg to about 200 mg/kg, 0.5 mg/kg to about 150 mg/kg, 0.5 mg/kg to about 100 mg/kg, 0.5 mg/kg to about 50 mg/kg, 0.5 mg/kg to about 25 mg/kg, 0.5 mg/kg to about 10 mg/kg, or 0.5 mg/kg to about 5 mg/kg, BIW. For example, a compound of formula I can be administered at an amount of about: 0.0001 mg/kg to about 200 mg/kg, 0.001 mg/kg to about 200 mg/kg, 0.5 mg/kg to about 200 mg/kg, 0.5 mg/kg to about 150 mg/kg, 0.5 mg/kg to about 100 mg/kg, 0.5 mg/kg to about 50 mg/kg, 0.5 mg/kg to about 25 mg/kg, 0.5 mg/kg to about 10 mg/kg, or 0.5 mg/kg to about 5 mg/kg, TIW. For example, a compound of formula I can be administered at an amount of about: 0.0001 mg/kg to about 200 mg/kg, 0.001 mg/kg to about 200 mg/kg, 0.5 mg/kg to about 200 mg/kg, 0.5 mg/kg to about 150 mg/kg, 0.5 mg/kg to about 100 mg/kg, 0.5 mg/kg to about 50 mg/kg, 0.5 mg/kg to about 25 mg/kg, 0.5 mg/kg to about 10 mg/kg, or 0.5 mg/kg to about 5 mg/kg, QW. For example, a compound of formula I can be administered at an amount of about: 0.0001 mg/kg to about 200 mg/kg, 0.001 mg/kg to about 200 mg/kg, 0.5 mg/kg to about 200 mg/kg, 0.5 mg/kg to about 150 mg/kg, 0.5 mg/kg to about 100 mg/kg, 0.5 mg/kg to about 50 mg/kg, 0.5 mg/kg to about 25 mg/kg, 0.5 mg/kg to about 10 mg/kg, or 0.5 mg/kg to about 5 mg/kg, Q2W. In one example, a compound of formula I can be administered at an amount of about 15 mg/kg to about 75 mg/kg, QD. In another example, a compound of formula I can be administered at an amount of about 20 mg/kg to about 50 mg/kg. In still another example, a compound of formula I can be administered at an amount of about 0.001 mg/kg, 0.01 mg/kg, 0.05 mg/kg, 0.1 mg/kg, 0.5 mg/kg, 1 mg/kg, 2 mg/kg, 3 mg/kg, 4 mg/kg, 5 mg/kg, 10 mg/kg, 15 mg/kg, 20 mg/kg, 25 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. Administration of a compound of formula I can be continuous. Administration of a compound of formula I can be intermittent.

For example, a compound of formula I can be administered at an amount of about: 1 mg/kg to about 200 mg/kg, 1 mg/kg to about 150 mg/kg, 1 mg/kg to about 100 mg/kg, 1 mg/kg to about 50 mg/kg, 1 mg/kg to about 25 mg/kg, 1 mg/kg to about 10 mg/kg, or 1 mg/kg to about 5 mg/kg, QD. For example, a compound of formula I can be administered at an amount of about: 1 mg/kg to about 200 mg/kg, 1 mg/kg to about 150 mg/kg, 1 mg/kg to about 100 mg/kg, 1 mg/kg to about 50 mg/kg, 1 mg/kg to about 25 mg/kg, 1 mg/kg to about 10 mg/kg, or 1 mg/kg to about 5 mg/kg, BIW. For example, a compound of formula I can be administered at an amount of about: 1 mg/kg to about 200 mg/kg, 1 mg/kg to about 150 mg/kg, 1 mg/kg to about 100 mg/kg, 1 mg/kg to about 50 mg/kg, 1 mg/kg to about 25 mg/kg, 1 mg/kg to about 10 mg/kg, or 1 mg/kg to about 5 mg/kg, TIW. For example, a compound of formula I can be administered at an amount of about: 1 mg/kg to about 200 mg/kg, 1 mg/kg to about 150 mg/kg, 1 mg/kg to about 100 mg/kg, 1 mg/kg to about 50 mg/kg, 1 mg/kg to about 25 mg/kg, 1 mg/kg to about 10 mg/kg, or 1 mg/kg to about 5 mg/kg, QW. For example, a compound of formula I can be administered at an amount of about: 1 mg/kg to about 200 mg/kg, 1 mg/kg to about 150 mg/kg, 1 mg/kg to about 100 mg/kg, 1 mg/kg to about 50 mg/kg, 1 mg/kg to about 25 mg/kg, 1 mg/kg to about 10 mg/kg, or 1 mg/kg to about 5 mg/kg, Q2W. In one example, a compound of formula I can be administered at an amount of about 15 mg/kg to about 75 mg/kg, QD. In another example, a compound of formula I can be administered at an amount of about 20 mg/kg to about 50 mg/kg. In still another example, a compound of formula I can be administered at an amount of about 0.001 mg/kg, 0.01 mg/kg, 0.05 mg/kg, 0.1 mg/kg, 0.5 mg/kg, 1 mg/kg, 2 mg/kg, 3 mg/kg, 4 mg/kg, 5 mg/kg, 10 mg/kg, 15 mg/kg, 20 mg/kg, 25 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. Administration of a compound of formula I can be continuous. Administration of a compound of formula I can be intermittent.

As used herein, the term daily is intended to mean that a therapeutic compound of a combination described herein, such as a compound of formula I, is administered once or more than once each day for a period of time. The term continuous is intended to mean that a therapeutic compound of a combination described herein, such as a compound of formula I, is administered daily for an uninterrupted period of at least 10 days to 52 weeks. The term intermittent or intermittently as used herein is intended to mean stopping and starting at either regular or irregular intervals. For example, intermittent administration of a therapeutic compound of a combination described herein, such as a compound of formula I, includes administration for one to six days per week (e.g., 2 to 3 times per week or QD), administration in cycles (e.g., daily administration for two to eight consecutive weeks, then a rest period with no administration at least one day), or, for example, administration on alternate days.

Where the PD-L1 inhibitor is a PD-L1 inhibitor antibody, it can be administered according to established regimens such as those provided in a package insert. The PD-L1 inhibitor antibody can be administered in an amount described herein and can be administered QW, once every 2 weeks (Q2W), once every 3 weeks (Q3W), or once every 4 weeks (Q4W). In one embodiment, the PD-L1 inhibitor antibody is administered Q2W or Q4W. In another embodiment, the PD-L1 inhibitor antibody is administered Q2W. In yet another embodiment, the PD-L1 inhibitor antibody is administered Q3W. In still another embodiment, the PD-L1 inhibitor antibody is administered BIW for at least 3 weeks. In still another embodiment, the PD-L1 inhibitor antibody is administered Q4W.

For example, durvalumab can be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 10 mg/kg, 12 mg/kg, 15 mg/kg, 20 mg/kg, 25 mg/kg, 30 mg/kg), QW. For example, durvalumab can be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 10 mg/kg, 12 mg/kg, 15 mg/kg, 20 mg/kg, 25 mg/kg, 30 mg/kg), Q2W. For example, durvalumab can be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 10 mg/kg, 12 mg/kg, 15 mg/kg, 20 mg/kg, 25 mg/kg, 30 mg/kg), Q4W. For example, durvalumab can be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 10 mg/kg, 12 mg/kg, 15 mg/kg, 20 mg/kg, 25 mg/kg, 30 mg/kg), B4W (twice every 4 weeks). For example, durvalumab can be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 10 mg/kg, 12 mg/kg, 15 mg/kg, 20 mg/kg, 25 mg/kg, 30 mg/kg), Q3W. For example, durvalumab can be administered at an amount of about 1000 mg to about 2000 mg (including for example 1000 mg, 1100 mg, 1200 mg, 1300 mg, 1400 mg, 1500 mg, 1600 mg), Q2W. For example, durvalumab can be administered at an amount of about 1000 mg to about 2000 mg (including for example 1000 mg, 1100 mg, 1200 mg, 1300 mg, 1400 mg, 1500 mg, 1600 mg), Q3W. For example, durvalumab can be administered at an amount of about 1000 mg to about 2000 mg (including for example 1000 mg, 1100 mg, 1200 mg, 1300 mg, 1400 mg, 1500 mg, 1600 mg), Q4W. Administration of durvalumab can be continuous. Administration of durvalumab can be intermittent.

Durvalumab can be administered as an intravenous infusion over about 10, 20, 30, 40, 50, or 60 or more minutes. Durvalumab can be administered as an intravenous infusion over about 60 minutes once every 1, 2, 3, 4, 5 or more weeks. Durvalumab can be administered as an intravenous infusion over about 60 minutes once every two weeks. Durvalumab can be administered as an intravenous infusion over about 60 minutes once every three weeks. Durvalumab can be administered as an intravenous infusion over about 60 minutes once every four weeks. Durvalumab can be administered as an intravenous infusion according to a package insert. Administration of durvalumab can be continuous. Administration of durvalumab can be intermittent.

For example, avelumab can be administered at an amount of about 0.1 mg/kg to about 30 mg/kg (including for example, 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg). For example, avelumab can be administered at an amount of about 0.1 mg/kg to about 30 mg/kg (including for example, 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg) QW. For example, avelumab can be administered at an amount of about 0.1 mg/kg to about 30 mg/kg (including for example, 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg) Q2W. For example, avelumab can be administered at an amount of about 0.1 to about 30 mg/kg (including for example, 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg) Q3W. For example, avelumab can be administered at an amount of about 0.1 mg/kg to about 30 mg/kg (including for example, 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg) Q4W. Administration of avelumab can be continuous. Administration of avelumab can be intermittent.

Avelumab can be administered as an intravenous infusion over about 10, 20, 30, 40, 50, or 60 or more minutes. Avelumab can be administered as an intravenous infusion over about 60 minutes once every 1, 2, 3, 4, 5 or more weeks. Avelumab can be administered as an intravenous infusion over about 60 minutes once every two weeks. Avelumab can be administered as an intravenous infusion over about 60 minutes once every three weeks. Avelumab can be administered as an intravenous infusion over about 60 minutes once every four weeks. Avelumab can be administered according to a provided package insert. Administration of avelumab can be continuous. Administration of avelumab can be intermittent.

For example, atezolizumab can be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg), QW. For example, atezolizumab can be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg), Q2W. For example, atezolizumab can be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg), Q3W. For example, atezolizumab can be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg), Q4W. For example, atezolizumab can be administered at an amount of about 1000 mg to about 2000 mg (including for example 1000 mg, 1100 mg, 1200 mg, 1300 mg, 1400 mg, 1500 mg, 1600 mg), Q2W. For example, atezolizumab can be administered at an amount of about 1000 mg to about 2000 mg (including for example 1000 mg, 1100 mg, 1200 mg, 1300 mg, 1400 mg, 1500 mg, 1600 mg), Q3W. For example, atezolizumab can be administered at an amount of about 1000 mg to about 2000 mg (including for example 1000 mg, 1100 mg, 1200 mg, 1300 mg, 1400 mg, 1500 mg, 1600 mg), Q4W. In one example atezolizumab can be administered at an amount of about 15 mg/kg, Q2W or Q4W. In one example, atezolizumab can be administered at an amount of about 1200 mg or 1500 mg, QM. Administration of atezolizumab can be continuous. Administration of atezolizumab can be intermittent.

Atezolizumab can be administered as an intravenous infusion over about 10, 20, 30, 40, 50, or 60 or more minutes. Atezolizumab can be administered as an intravenous infusion over about 60 minutes once every 1, 2, 3, 4, 5 or more weeks. Atezolizumab can be administered as an intravenous infusion over about 60 minutes once every two weeks. Atezolizumab can be administered as an intravenous infusion over about 60 minutes once every three weeks. Atezolizumab can be administered as an intravenous infusion over about 60 minutes once every four weeks. Administration of atezolizumab can be continuous. Administration of atezolizumab can be intermittent.

For example, BMS-936559 can be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg), QW. For example, BMS-936559 can be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg), Q2W. For example, BMS-936559 can be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg), Q3W. For example, BMS-936559 can be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg), Q4W. Administration of BMS-936559 can be continuous. Administration of BMS-936559 can be intermittent.

BMS-936559 can be administered as an intravenous infusion over about 10, 20, 30, 40, 50, or 60 or more minutes. BMS-936559 can be administered as an intravenous infusion over about 60 minutes once every 1, 2, 3, 4, 5 or more weeks. BMS-936559 can be administered as an intravenous infusion over about 60 minutes once every two weeks. BMS-936559 can be administered as an intravenous infusion over about 60 minutes twice every three weeks. BMS-936559 can be administered as an intravenous infusion over about 60 minutes three times every six weeks. Administration of BMS-936559 can be continuous. Administration of BMS-936559 can be intermittent.

For example, STI-A1010, STI-A1011, STI-A1012, STI-A1013, or STI-A1010, STI-A1011, STI-A1012, STI-A1013, STI-A1014, and STI-A1015 (Sorrento Therapeutics) can independently be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg), QW. For example, STI-A1010, STI-A1011, STI-A1012, STI-A1013, or STI-A1010, STI-A1011, STI-A1012, STI-A1013, STI-A1014, or STI-A1015 can independently be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg), Q2W. For example, STI-A1010, STI-A1011, STI-A1012, STI-A1013, or STI-A1010, STI-A1011, STI-A1012, STI-A1013, STI-A1014, or STI-A1015 can independently be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg), Q3W. For example, STI-A1010, STI-A1011, STI-A1012, STI-A1013, or STI-A1010, STI-A1011, STI-A1012, STI-A1013, STI-A1014, or STI-A1015 can independently be administered at an amount of about 0.1 mg/kg to about 30 mg/kg (including for example 0.1 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg), Q4W. Administration of STI-A1010, STI-A1011, STI-A1012, STI-A1013, or STI-A1010, STI-A1011, STI-A1012, STI-A1013, STI-A1014, or STI-A1015 can be continuous. Administration of STI-A1010, STI-A1011, STI-A1012, STI-A1013, or STI-A1010, STI-A1011, STI-A1012, STI-A1013, STI-A1014, or STI-A1015 can be intermittent.

STI-A1010, STI-A1011, STI-A1012, STI-A1013, or STI-A1010, STI-A1011, STI-A1012, STI-A1013, STI-A1014, or STI-A1015 can independently be administered as an intravenous infusion over about 10, 20, 30, 40, 50, or 60 or more minutes. STI-A1010, STI-A1011, STI-A1012, STI-A1013, or STI-A1010, STI-A1011, STI-A1012, STI-A1013, STI-A1014, or STI-A1015 can independently be administered as an intravenous infusion over about 60 minutes once every 1, 2, 3, 4, 5 or more weeks. STI-A1010, STI-A1011, STI-A1012, STI-A1013, or STI-A1010, STI-A1011, STI-A1012, STI-A1013, STI-A1014, or STI-A1015) can independently be administered as an intravenous infusion over about 60 minutes once every two weeks. STI-A1010, STI-A1011, STI-A1012, STI-A1013, or STI-A1010, STI-A1011, STI-A1012, STI-A1013, STI-A1014, or STI-A1015 can independently be administered as an intravenous infusion over about 60 minutes twice every three weeks. STI-A1010, STI-A1011, STI-A1012, STI-A1013, or STI-A1010, STI-A1011, STI-A1012, STI-A1013, STI-A1014, or STI-A1015 can independently be administered as an intravenous infusion over about 60 minutes three times every six weeks. Administration of STI-A1010, STI-A1011, STI-A1012, STI-A1013, or STI-A1010, STI-A1011, STI-A1012, STI-A1013, STI-A1014, or STI-A1015 can be continuous. Administration of STI-A1010, STI-A1011, STI-A1012, STI-A1013, or STI-A1010, STI-A1011, STI-A1012, STI-A1013, STI-A1014, or STI-A1015 can be intermittent.

The combinations described herein can be administered in a regimen. The regimen can be structured to provide therapeutically effective amounts of a compound of formula I and a PD-L1 inhibitor, such as a PD-L1 inhibitor antibody, over a predetermined period of time (e.g., an administration time). The regimen can be structured to limit or prevent side-effects or undesired complications of each of the components of the combination described herein. The regimen can be structured in a manner that results in increased effect for both therapies of the combination (e.g., synergy). Regimens useful for treating cancer can include any number of days of administration which can be repeated as necessary. Administration periods can be broken by a rest period that includes no administration of at least one therapy. For example, a regimen can include administration periods that include 2, 3, 5, 7, 10, 15, 21, 28, or more days. These periods can be repeated. For example, a regimen can include a set number of days as previously described where the regimen is repeated 1, 2, 3, 4, 5, 6, 7, 8, 9, 10, 11, 12, 13, or more times.

Regimens can include a rest period of at least 1, 2, 3, 5, 7, 10, or more days, where at least one therapy is no longer administered to a patient. The rest period can be determined by, for example, monitoring the reaction of the patient to the drug or by measuring the efficacy of the treatment. A rest period can be applicable to a single therapy, such that only one therapy of a combination described herein is discontinued in the rest period but the other therapy(ies) are still administered. Rest periods can be applied to all of the therapies administered to the subject such that the subject receives no therapy for a set period of time during the rest period.

Regimens described herein for the treatment of cancer using the combinations described herein can be continued until disease progression or unacceptable toxicity.

Regimens for administration of combinations described herein include, for example administration of a compound of formula I BIW or TIW and administration of a PD-L1 inhibitor. For example, a compound of formula I can be administered QD for about 21 days and a PD-L1 inhibitor antibody described herein can be administered Q2W or Q4W). For example, a compound of formula I can be administered BIW or TIW and a PD-L1 inhibitor antibody described herein can be administered Q2W. In another exemplary regimen, a compound of formula I can be administered BIW or TIW and a PD-L1 inhibitor antibody can be administered BIW for 2 or 3 weeks. In still another exemplary regimen, a compound of formula I can be administered BIW or TIW and a PD-L1 inhibitor antibody can be administered Q4W. In still another exemplary regimen, a compound of formula I can be administered BIW and a PD-L1 inhibitor described herein can be administered Q2W, Q3W, or Q4W. In certain instances, such regimens include administration of PD-L1 inhibitor antibody administered Q2W, Q3W, or Q4W. In yet another exemplary regimen, a compound of formula I can be administered TIW and a PD-L1 inhibitor described herein can be administered Q2W, Q3W, or Q4W. In certain instances, such regimens include administration of PD-L1 inhibitor antibody administered Q2W, Q3W, or Q4W. In certain instances, such regimens include administration of a compound of formula I administered QD. In certain instances, such regimens include administration of a compound of formula I administered QD for at least 21 days. In yet another exemplary regimen, a compound of formula I can be administered QD or QW and a PD-L1 inhibitor (e.g., a PD-L1 inhibitor antibody) is administered Q2W, Q3W, or Q4W.

The regimen can be a regimen for administration of avelumab with a compound of formula I as described herein. In one exemplary regimen including avelumab, a compound of formula I can be administered BIW or TIW and avelumab is administered in accordance with the prescribing information provided in, for example, a package insert. In another exemplary regimen, avelumab is administered at an amount of about 1 mg/kg to about 20 mg/kg on day 1 of the regimen, and Q2W thereafter until disease progression or unacceptable toxicity and a compound of formula I is administered BIW or TIW over the same period of time. In another exemplary regimen, avelumab is administered at an amount of about 1 mg/kg to about 20 mg/kg on day 1 of a regimen, and Q3W thereafter until disease progression or unacceptable toxicity and a compound of formula I is administered BIW or TIW over the same period of time. Avelumab can be administered Q4W with a compound of formula I, where the compound of formula I is administered, for example, BIW or TIW during the course of such a regimen. Avelumab can be administered Q2W with a compound of formula I, where the compound of formula I is administered, for example, BIW or TIW during the course of such a regimen. In still another exemplary regimen, avelumab can be administered Q2W or Q4W with a compound of formula I, where the compound of formula I is administered, for example, QD or QW during the course of such a regimen. Such regimens can be repeated as described above (e.g., 1, 2, 3, 4, 5, 6, 7, 8, 9, 10, 11, 12, or more times).

In another exemplary regimen including avelumab, a compound of formula I can be administered QD and avelumab is administered in accordance with the prescribing information provided in, for example, a package insert. In another exemplary regimen, avelumab is administered at an amount of about 1 mg/kg to about 20 mg/kg on day 1 of the regimen, and Q2W thereafter until disease progression or unacceptable toxicity and a compound of formula I is administered QD over the same period of time. In another exemplary regimen, avelumab is administered at an amount of about 1 mg/kg to about 20 mg/kg on day 1 of a regimen, and Q3W thereafter until disease progression or unacceptable toxicity and a compound of formula I is administered QD over the same period of time. Avelumab can be administered Q4W with a compound of formula I, where the compound of formula I is administered QD during the course of such a regimen. Avelumab can be administered Q2W with a compound of formula I, where the compound of formula I is administered QD during the course of such a regimen. Such regimens can be repeated as described above (e.g., 1, 2, 3, 4, 5, 6, 7, 8, 9, 10, 11, 12, or more times).

The regimen can be a regimen for administration of durvalumab with a compound of formula I as described herein. In one exemplary regimen including durvalumab, a compound of formula I can be administered BIW or TIW and durvalumab is administered in accordance with the prescribing information provided in, for example, a package insert. In another exemplary regimen, durvalumab is administered at an amount of about 1 mg/kg to about 20 mg/kg on day 1 and Q2W thereafter until disease progression or unacceptable toxicity and a compound of formula I is administered BIW or TIW over the same period of time. In still another exemplary regimen, durvalumab is administered at an amount of about 1 mg/kg to about 20 mg/kg on day 1 and Q4W thereafter until disease progression or unacceptable toxicity and a compound of formula I is administered BIW or TIW over the same period of time. In still another exemplary regimen, durvalumab can be administered Q2W, where the compound of formula I is administered, for example, BIW or TIW during the course of such a regimen. In still another exemplary regimen, durvalumab can be administered Q4W, where the compound of formula I is administered, for example, BIW or TIW during the course of such a regimen. In yet another exemplary regimen, durvalumab can be administered Q2W or Q4W, where the compound of formula I is administered, for example, QD or QW during the course of such a regimen. Such regimens can be repeated as described above (e.g., 1, 2, 3, 4, 5, 6, 7, 8, 9, 10, 11, 12, or more times).

In another exemplary regimen including durvalumab, a compound of formula I can be administered QD and durvalumab is administered in accordance with the prescribing information provided in, for example, a package insert. In another exemplary regimen, durvalumab is administered at an amount of about 1 mg/kg to about 20 mg/kg on day 1 and Q2W thereafter until disease progression or unacceptable toxicity and a compound of formula I is administered QD over the same period of time. In still another exemplary regimen, durvalumab is administered at an amount of about 1 mg/kg to about 20 mg/kg on day 1 and Q4W thereafter until disease progression or unacceptable toxicity and a compound of formula I is administered QD over the same period of time. In still another exemplary regimen, durvalumab can be administered Q2W, where the compound of formula I is administered QD during the course of such a regimen. In still another exemplary regimen, durvalumab can be administered Q4W, where the compound of formula I is administered QD during the course of such a regimen. In yet another exemplary regimen, durvalumab can be administered Q3W where the compound of formula I is administered QD during the course of such a regimen. Such regimens can be repeated as described above (e.g., 1, 2, 3, 4, 5, 6, 7, 8, 9, 10, 11, 12, or more times).

The regimen can be a regimen for administration of atezolizumab with a compound of formula I as described herein. In one exemplary regimen including atezolizumab, a compound of formula I can be administered BIW or TIW and atezolizumab is administered in accordance with the prescribing information provided in, for example, a package insert. In another exemplary regimen, atezolizumab is administered at an amount of about 10 mg/kg to about 20 mg/kg on day 1 and Q3W thereafter until disease progression or unacceptable toxicity and a compound of formula I is administered BIW or TIW over the same period of time. In still another exemplary regimen, atezolizumab is administered at an amount of about 10 mg/kg to about 20 mg/kg on day 1 and Q4W thereafter until disease progression or unacceptable toxicity and a compound of formula I is administered BIW or TIW over the same period of time. In another exemplary regimen, atezolizumab is administered at an amount of about 15 mg/kg on day 1 and Q3W thereafter until disease progression or unacceptable toxicity and a compound of formula I is administered BIW or TIW over the same period of time. In still another exemplary regimen, atezolizumab is administered at an amount of about 15 mg/kg on day 1 and Q4W thereafter until disease progression or unacceptable toxicity and a compound of formula I is administered BIW or TIW over the same period of time. In another exemplary regimen, atezolizumab is administered at an amount of about 1000 mg to about 2000 mg on day 1 and Q3W thereafter until disease progression or unacceptable toxicity and a compound of formula I is administered BIW or TIW over the same period of time. In still another exemplary regimen, atezolizumab is administered at an amount of about 1000 mg to about 2000 mg on day 1 and Q4W thereafter until disease progression or unacceptable toxicity and a compound of formula I is administered BIW or TIW over the same period of time. In another exemplary regimen, atezolizumab is administered at an amount of about 1200 mg or about 1500 mg on day 1 and Q3W thereafter until disease progression or unacceptable toxicity and a compound of formula I is administered BIW or TIW over the same period of time. In still another exemplary regimen, atezolizumab is administered at an amount of about 1200 mg or about 1500 mg on day 1 and Q4W thereafter until disease progression or unacceptable toxicity and a compound of formula I is administered BIW or TIW over the same period of time. In still another exemplary regimen, atezolizumab can be administered Q3W, where the compound of formula I is administered, for example, BIW or TIW during the course of such a regimen. In still another exemplary regimen, atezolizumab can be administered Q4W, where the compound of formula I is administered, for example, BIW or TIW during the course of such a regimen. In yet another exemplary regimen, atezolizumab can be administered Q2W or Q4W, where the compound of formula I is administered, for example, QD or QW during the course of such a regimen. Such regimens can be repeated as described above (e.g., 1, 2, 3, 4, 5, 6, 7, 8, 9, 10, 11, 12, or more times).

The regimen can be a regimen for administration of atezolizumab with a compound of formula I as described herein. In one exemplary regimen including atezolizumab, a compound of formula I can be administered QD and atezolizumab is administered in accordance with the prescribing information provided in, for example, a package insert. In another exemplary regimen, atezolizumab is administered at an amount of about 10 mg/kg to about 20 mg/kg on day 1 and Q3W thereafter until disease progression or unacceptable toxicity and a compound of formula I is administered QD over the same period of time. In still another exemplary regimen, atezolizumab is administered at an amount of about 10 mg/kg to about 20 mg/kg on day 1 and Q4W thereafter until disease progression or unacceptable toxicity and a compound of formula I is administered QD over the same period of time. In another exemplary regimen, atezolizumab is administered at an amount of about 15 mg/kg on day 1 and Q3W thereafter until disease progression or unacceptable toxicity and a compound of formula I is administered QD over the same period of time. In still another exemplary regimen, atezolizumab is administered at an amount of about 15 mg/kg on day 1 and Q4W thereafter until disease progression or unacceptable toxicity and a compound of formula I is administered QD over the same period of time. In another exemplary regimen, atezolizumab is administered at an amount of about 1000 mg to about 2000 mg on day 1 and Q3W thereafter until disease progression or unacceptable toxicity and a compound of formula I is administered QD over the same period of time. In still another exemplary regimen, atezolizumab is administered at an amount of about 1000 mg to about 2000 mg on day 1 and Q4W thereafter until disease progression or unacceptable toxicity and a compound of formula I is administered QD over the same period of time. In another exemplary regimen, atezolizumab is administered at an amount of about 1200 mg or about 1500 mg on day 1 and Q3W thereafter until disease progression or unacceptable toxicity and a compound of formula I is administered QD over the same period of time. In still another exemplary regimen, atezolizumab is administered at an amount of about 1200 mg or about 1500 mg on day 1 and Q4W thereafter until disease progression or unacceptable toxicity and a compound of formula I is administered QD over the same period of time. In still another exemplary regimen, atezolizumab can be administered Q3W, where the compound of formula I is administered QD during the course of such a regimen. In still another exemplary regimen, atezolizumab can be administered Q4W, where the compound of formula I is administered QD during the course of such a regimen. In yet another exemplary regimen, atezolizumab can be administered Q2W, Q3W, or Q4W, where the compound of formula I is administered QD during the course of such a regimen. Such regimens can be repeated as described above (e.g., 1, 2, 3, 4, 5, 6, 7, 8, 9, 10, 11, 12, or more times).

It should also be appreciated that the combinations described herein for treating cancer can be coadministered with other active agents other than those present in the combinations described herein (e.g., anti-cancer agents). Regimens for administration of a combination described herein, including the exemplary regimens set forth above, can be modified as necessary to include administration of such active agents. Administration of such active agents, e.g., anti-cancer agents, can be performed QD, QW, QM, BID, BIW, TIW, Q2W, Q3W, or Q4W, or in accordance with prescribing information for such anti-cancer agents as set forth, for example, in a package insert. Exemplary anti-cancer agents include but are not limited to: ABRAXANE; abiraterone; ace-11; aclarubicin; acivicin; acodazole hydrochloride; acronine; actinomycin; acylfulvene; adecypenol; adozelesin; adriamycin; aldesleukin; all trans-retinoic acid (ATRA); altretamine; ambamustine; ambomycin; ametantrone acetate; amidox; amifostine; aminoglutethimide; aminolevulinic acid; amrubicin; amsacrine; anagrelide; anastrozole; andrographolide; antarelix; anthramycin; aphidicolin glycinate; apurinic acid; ara-CDP-DL-PTBA; arginine deaminase; ARRY-162; ARRY-300; ARRY-142266; AS703026; asparaginase; asperlin; asulacrine; atamestane; atrimustine; axinastatin 1; axinastatin 2; axinastatin 3; azasetron; azatoxin; azatyrosine; azacitidine; AZD8330; azetepa; azotomycin; balanol; batimastat; BAY 11-7082; BAY 43-9006; BAY 869766; bendamustine; benzochlorins; benzodepa; benzoylstaurosporine; beta-alethine; betaclamycin B; betulinic acid; b-FGF inhibitor; bicalutamide; bisantrene; bisaziridinylspermine; bisnafide; bisnafide dimesylate; bistratene A; bisantrene hydrochloride; bleomycin; bleomycin sulfate; busulfan; bizelesin; breflate; bortezomib; brequinar sodium; bropirimine; budotitane; buthionine sulfoximine; bryostatin; cactinomycin; calusterone; calcipotriol; calphostin C; camptothecin derivatives; capecitabine; carboxamide-amino-triazole; carboxyamidotriazole; CaRest M3; CARN 700; caracemide; carbetimer; carboplatin; carmustine; carubicin hydrochloride; carzelesin; castanospermine; cecropin B; cedefingol; celecoxib; cetrorelix; chlorins; chloroquinoxaline sulfonamide; cicaprost; chlorambucil; Chlorofusin; cirolemycin; cisplatin; CI-1040; cis-porphyrin; cladribine; clomifene analogues; clotrimazole; collismycin A; collismycin B; combretastatin A4; combretastatin analogue; conagenin; crambescidin 816; crisnatol; crisnatol mesylate; cryptophycin 8; cryptophycin A derivatives; curacin A; cyclopentanthraquinones; cycloplatam; cypemycin; cyclophosphamide; cytarabine; cytarabine ocfosfate; cytolytic factor; cytostatin; dacarbazine; dactinomycin; daunorubicin; daunorubicin hydrochloride; decarbazine; dacliximab; dasatinib; decitabine; dehydrodidemnin B; deslorelin; dexamethasone; dexifosfamide; dexrazoxane; dexverapamil; dexormaplatin; dezaguanine; dezaguanine mesylate; diaziquone; didemnin B; didox; diethylnorspermine; dihydro 5 azacytidine; dihydrotaxol; 9-dioxamycin; diphenyl spiromustine; docosanol; dolasetron; docetaxel; doxorubicin; doxorubicin hydrochloride; doxifluridine; droloxifene; droloxifene citrate; dromostanolone propionate; dronabinol; duazomycin; duocarmycin SA; ebselen; ecomustine; edelfosine; edrecolomab; edatrexate; eflornithine hydrochloride; eflornithine; elemene; emitefur; elsamitrucin; enloplatin; enpromate; epipropidine; epirubicin; epirubicin hydrochloride; epristeride; erbulozole; eribulin; esorubicin hydrochloride; estramustine; estramustine phosphate sodium; etanidazole; etoposide; etoposide phosphate; etoprine; exemestane; fadrozole; fadrozole hydrochloride; fazarabine; fenretinide; filgrastim; finasteride; flavopiridol; flezelastine; fluasterone; floxuridine; fludarabine phosphate; fludarabine; fluorodaunorubicin hydrochloride; forfenimex; formestane; fluorouracil; floxouridine; flurocitabine; fosquidone; fostriecin sodium; fostriecin; fotemustine; gadolinium texaphyrin; gallium nitrate; galocitabine; ganirelix; gelatinase inhibitors; gemcitabine; geldanamycin; gossyphol; GDC-0973; GSK1120212/ trametinib; herceptin; hydroxyurea; hepsulfam; heregulin; hexamethylene bisacetamide; hypericin; ibandronic acid; ibrutinib; idarubicin; idarubicin hydrochloride; ifosfamide; canfosfamide; ilmofosine; iproplatin; idoxifene; idramantone; ilmofosine; ilomastat; imidazoacridones; imatinib (e.g., GLEEVEC); imiquimod; iobenguane; iododoxorubicin; ipomeanol; irinotecan; irinotecan hydrochloride; irsogladine; isobengazole; isohomohalicondrin B; itasetron; iimofosine; interleukin II (including recombinant interleukin IL-2; or rIL.sub.2); interferon alfa-2a; interferon alfa-2b; interferon alfa-n1; interferon alfa-n3; interferon beta-1a; interferon gamma-1b; jasplakinolide; kahalalide F; lamellarin N triacetate; lanreotide; leinamycin; lenograstim; lentinan sulfate; leptolstatin; letrozole; leuprorelin; levamisole; liarozole; lissoclinamide 7; lobaplatin; lombricine; lometrexol; lonidamine; losoxantrone; lovastatin; loxoribine; lurtotecan; lutetium texaphyrin; lysofylline; lanreotide acetate; lapatinib; letrozole; leucovorin; leuprolide acetate; liarozole hydrochloride; lometrexol sodium; lomustine; lenalidomide; lenvatinib; losoxantrone hydrochloride; LY294002; pomalidomide; maitansine; mannostatin A; marimastat; masoprocol; maspin; matrilysin inhibitors; menogaril; merbarone; meterelin; methioninase; metoclopramide; MIF inhibitor; mifepristone; miltefosine; mirimostim; mitoguazone; mitolactol; mitonafide; mitoxantrone; mofarotene; molgramostim; mopidamol; mycaperoxide B; myriaporone; maytansine; mechlorethamine hydrochloride; megestrol acetate; melengestrol acetate; melphalan; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nafarelin; nagrestip; napavin; naphterpin; nartograstim; nedaplatin; nemorubicin; neridronic acid; nilutamide; nisamycin; nitric oxide modulators; nitroxide antioxidant; nitrullyn; nocodazole; nogalamycin; oblimersen (GENASENSE); octreotide; okicenone; oligonucleotides; onapristone; ondansetron; ondansetron; oracin; oral cytokine inducer; ormaplatin; oxisuran; oxaloplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; porfiromycin; prednisone; prostaglandin J2; pyrazoloacridine; paclitaxel; PD035901; PD184352; PD318026; PD98059; peliomycin; pentamustine; peplomycin sulfate; PKC412; pipobroman; piposulfan; piroxantrone hydrochloride; plicamycin; plomestane; podophyllotoxin; polyphenol E; porfimer sodium; porfiromycin; prednimustine; procarbazine; procarbazine hydrochloride; puromycin; puromycin hydrochloride; pyrazofurin; raltitrexed; ramosetron; retelliptine demethylated; rhizoxin; rituximab; RII retinamide; rogletimide; rohitukine; romurtide; roquinimex; rubiginone B1; ruboxyl; riboprine; romidepsin; safingol; safingol hydrochloride; saintopin; sarcophytol A; sargramostim; semustine; sizofiran; sobuzoxane; sodium borocaptate; sodium phenylacetate; solverol; sonermin; sorafenib; sunitinib; sparfosic acid; spicamycin D; spiromustine; splenopentin; spongistatin 1; Spongistatin 2; Spongistatin 3; Spongistatin 4; Spongistatin 5; Spongistatin 6; Spongistatin 7; Spongistatin 8; and Spongistatin 9; squalamine; stipiamide; stromelysin inhibitors; sulfinosine; suradista; suramin; swainsonine; SB239063; selumetinib/ AZD6244; simtrazene; SP600125; sparfosate sodium; sparsomycin; spirogermanium hydrochloride; spiroplatin; streptonigrin; streptozocin; sulofenur; tallimustine; tamoxifen methiodide; tauromustine; tazarotene; tecogalan sodium; tegafur; tellurapyrylium; temoporfin; temozolomide; teniposide; tetrachlorodecaoxide; tetrazomine; thaliblastine; thiocoraline; thrombopoietin; thymalfasin; thymopoietin receptor agonist; thymotrinan; tirapazamine; titanocene bichloride; topsentin; toremifene; tretinoin; triacetyluridine; triciribine; trimetrexate; triptorelin; tropisetron; turosteride; tyrphostins; talisomycin; TAK-733; taxotere; tegafur; teloxantrone hydrochloride; teroxirone; testolactone; thiamiprine; thioguanine; thiotepa; tiazofurin; tirapazamine; toremifene citrate; trastuzumab; trestolone acetate; triciribine phosphate; trimetrexate; trimetrexate glucuronate; triptorelin; tubulozole hydrochloride; tumor necrosis factor-related apoptosis-inducing ligand (TRAIL); UBC inhibitors; ubenimex; U0126; uracil mustard; uredepa; vapreotide; variolin B; velaresol; veramine; verteporfin; vinorelbine; vinxaltine; vitaxin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; wortmannin; XL518; zanoterone; zeniplatin; zilascorb; zinostatin stimalamer; zinostatin; and zorubicin hydrochloride.

Other exemplary anti-cancer agents include Erbulozole (e.g., R-55104); Dolastatin 10 (e.g., DLS-10 and NSC-376128); Mivobulin isethionate (e.g., CI-980); NSC-639829; Discodermolide (e.g., NVP-XX-A-296); ABT-751 (Abbott; e.g., E-7010); Altorhyrtin A; Altorhyrtin C); Cemadotin hydrochloride (e.g., LU-103793 and NSC-D-669356); Epothilone A; Epothilone B; Epothilone C; Epothilone D; Epothilone E; Epothilone F; Epothilone B N-oxide; Epothilone A N-oxide; 16-aza-epothilone B; 21-aminoepothilone B; 21-hydroxyepothilone D; 26-fluoroepothilone; Auristatin PE (e.g., NSC-654663); Soblidotin (e.g., TZT-1027); LS-4559-P (Pharmacia; e.g., LS-4577); LS-4578 (Pharmacia; e.g., LS-477-P); LS-4477 (Pharmacia); LS-4559 (Pharmacia); RPR-112378 (Aventis); DZ-3358 (Daiichi); FR-182877 (Fujisawa; e.g., WS-9265B); GS-164 (Takeda); GS-198 (Takeda); KAR-2 (Hungarian Academy of Sciences); BSF-223651 (BASF; e.g., ILX-651 and LU-223651); SAH-49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (e.g., LY-355703); AC-7739 (Ajinomoto; e.g., AVE-8063A and CS-39.HCl); AC-7700 (Ajinomoto; e.g., AVE-8062; AVE-8062A; CS-39-L-Ser.HCl; and RPR-258062A); Vitilevuamide; Tubulysin A; Canadensol; CA-170 (Curis, Inc.); Centaureidin (e.g., NSC-106969); T-138067 (Tularik; e.g., T-67; TL-138067 and TI-138067); COBRA-1 (Parker Hughes Institute; e.g., DDE-261 and WHI-261); H10 (Kansas State University); H16 (Kansas State University); Oncocidin A1 (e.g., BTO-956 and DIME); DDE-313 (Parker Hughes Institute); Fijianolide B; Laulimalide; SPA-2 (Parker Hughes Institute); SPA-1 (Parker Hughes Institute; e.g., SPIKET-P); 3-IAABU (Cytoskeleton/Mt. Sinai School of Medicine; e.g., MF-569); Narcosine (e.g., NSC-5366); Nascapine; D-24851 (Asta Medica); A-105972 (Abbott); Hemiasterlin; 3-BAABU (Cytoskeleton/Mt. Sinai School of Medicine; e.g., MF-191); TMPN (Arizona State University); Vanadocene acetylacetonate; T-138026 (Tularik); Monsatrol; Inanocine (e.g., NSC-698666); 3-IAABE (Cytoskeleton/Mt. Sinai School of Medicine); A-204197 (Abbott); T-607 (Tuiarik; e.g., T-900607); RPR-115781 (Aventis); Eleutherobins (e.g., Desmethyleleutherobin; Desaetyleleutherobin; Isoeleutherobin A; and Z-Eleutherobin); Caribaeoside; Caribaeolin;

Halichondrin B; D-64131 (Asta Medica); D-68144 (Asta Medica); Diazonamide A; A-293620 (Abbott); NPI-2350 (Nereus); Taccalonolide A; TUB-245 (Aventis); A-259754 (Abbott); Diozostatin; (−)-Phenylahistin (e.g., NSCL-96F037); D-62638 (Asta Medica); D-62636 (Asta Medica); Myoseverin B; D-43411 (Zentaris; e.g., D-81862); A-289099 (Abbott); A-318315 (Abbott); HTI-286 (e.g., SPA-110; trifluoroacetate salt) (Wyeth); D-82317 (Zentaris); D-82318 (Zentaris); SC-12983 (NCI); Resverastatin phosphate sodium; BPR-OY-007 (National Health Research Institutes); and SSR-250411 (Sanofi)); goserelin; leuprolide; triptolide; homoharringtonine; topotecan; itraconazole; deoxyadenosine; sertraline; pitavastatin; clofazimine; 5-nonyloxytryptamine; vemurafenib; dabrafenib; gefitinib (IRESSA); erlotinib (TARCEVA); cetuximab (ERBITUX); lapatinib (TYKERB); panitumumab (VECTIBIX); vandetanib (CAPRELSA); afatinib/BIBW2992; CI-1033/canertinib; neratinib/HKI-272; CP-724714; TAK-285; AST-1306; ARRY334543; ARRY-380; AG-1478; dacomitinib/PF299804; OSI-420/desmethyl erlotinib; AZD8931; AEE726; pelitinib/EKB-569; CUDC-101; WZ8040; WZ4002; WZ3146; AG-490; XL647; PD153035; 5-azathioprine; 5-aza-2'-deoxycytidine; 17-N-Allylamino-17-Demethoxygeldanamycin (17-AAG); 20-epi-1,25 dihydroxyvitamin D3; 5 ethynyluracil; and BMS-599626.

In certain embodiments, the combinations described herein are coadministered with an anti-cancer agent described above, where the anti-cancer agent has known activity against a particular cancer (e.g., gemcitibine coadministered with a combination described herein for treating pancreatic cancer). The anti-cancer agents above can be approved for use in treating certain indications (e.g., certain cancers) at concentrations, amounts, and using treatment regimens known in the art.

It is understood that modifications which do not substantially affect the activity of the various embodiments of this invention are also included within the definition of the invention provided herein. Accordingly, the following examples are intended to illustrate but not limit the present invention.

EXAMPLES

Example 1

In Example 1 HBI-8000 was tested in two doses as monotherapy and in two doses in combination with PD-L1 inhibitor antibody at 5 mg/kg. The experiment included a vehicle-treated group and a PD-L1 inhibitor antibody monotherapy group, which served as control groups for analysis of efficacy. Tumors were measured twice per week until the study was ended on Day 47. Each animal was euthanized when its tumor attained the endpoint tumor volume of 1000 mm$^3$ or on the final day of the study, whichever came first, and the time to endpoint (TTE) for each mouse was calculated. Treatment response was determined from an analysis of percent tumor growth delay (% TGD), defined as the percent increase in the median time to endpoint (TTE) for treated versus control mice; and by logrank significance of differences in survival among groups and regression responses.

Mice: Female C57BL/6 mice (Charles River Laboratories) were eight weeks old, with a body weight (BW) range of 15.4 to 22.0 grams on Day 1 of the study. The animals were fed ad libitum water (reverse osmosis, 1 ppm Cl), and NIH 31 Modified and Irradiated Lab Diet® consisting of 18.0% crude protein, 5.0% crude fat, and 5.0% crude fiber. The mice were housed on irradiated Enrich-o'cobs™ Laboratory Animal Bedding in static microisolators on a 12-hour light cycle at 20-22° C. (68-72° F.) and 40-60% humidity.

Tumor Cell Culture: MC38 murine colon carcinoma cells were maintained in Dulbecco's Modified Eagle Medium (DMEM) supplemented with 10% fetal bovine serum and 2 mM glutamine, 100 units/mL penicillin G sodium, 100 µg/mL streptomycin sulfate, and 25 µg/mL gentamicin. Cell cultures were maintained in tissue culture flasks in a humidified incubator at 37° C., in an atmosphere of 5% $CO_2$ and 95% air.

Tumor Implantation: Cells were harvested during exponential growth, and resuspended in cold DMEM. Each mouse was inoculated subcutaneously in the right flank with $1 \times 10^6$ cells (0.1 mL of cell suspension). Tumors were calipered in two dimensions to monitor growth as their mean volume approached the desired 100-150 mm$^3$ range. Tumor burden was calculated using the formula:

$$\text{Tumor volume (mm}^3\text{)} = \frac{w^2 \times l}{2}$$

where w=width and l=length, in mm, of the tumor. Tumor weight may be estimated with the assumption that 1 mg is equivalent to 1 mm$^3$ of tumor volume. Fourteen days after tumor implantation, which was designated as Day 1 of the study, animals with individual tumor volumes from 75 to 221 mm$^3$ were sorted into eleven groups (n=10/group) with group mean tumor volume of 130-133 mm$^3$.

Test Articles: HUYA Bioscience International provided HBI-8000 (Lot No. 1384:0033). Anti-PDL-1 10F.9G2 (anti-PDL-1, Lot No. 5786-7-8/0815) was purchased from Bio X cell (West Lebanon, N. H.). All agents were prepared according to protocol instructions.

Dosing Solutions: HBI-8000 was prepared by diluting in 0.2% CMC: 0.1% Tween 80 to yield a 5 mg/mL dosing solution. Dosing solutions were prepared fresh weekly and stored at 4° C. Anti-PDL-1 antibody dosing solution was prepared by diluting an aliquot of the stock (5.37 mg/mL) to 0.5 mg/mL in sterile PBS. The anti-PDL-1 antibody dosing solution was prepared twice weekly and stored at 4° C.

C57BL/6 mice were dosed according to the MC38-e063 protocol shown in Table 2. All doses were prepared as described above. HBI-8000 was administered orally (p.o.), once daily for twenty-one days (qd×21). Dosing was adjusted per animal body weight. All antibody regimens were administered at 5 mg/kg, intraperitoneally (i.p.), twice weekly for three weeks (biwk×3), and dosing was adjusted per animal body weight.

TABLE 2

| Group | Treatment | Frequency |
| --- | --- | --- |
| Group 1 | Vehicle (2% CMC: 0.1% Tween 80) | p.o., qd × 21 |
| Group 2 | HBI-8000 at 20 mg/kg | p.o., qd × 21 |
| Group 3 | HBI-8000 at 50 mg/kg | p.o., qd × 21 |
| Group 4 | PD-L1 inhibitor antibody at 5 mg/kg | i.p., biwk × 3 |
| Group 5 | HBI-8000 at 20 mg/kg plus PD-L1 inhibitor antibody at 5 mg/kg | p.o., qd × 21 i.p., biwk × 3 |
| Group 6 | HBI-8000 at 50 mg/kg plus PD-L1 inhibitor antibody at 5 mg/kg | p.o., qd × 21 i.p., biwk × 3 |

Tumor Growth Delay: Tumors were measured using calipers twice per week, and each animal was euthanized when its tumor reached a volume of 1000 mm$^3$ or at the end of the study (D47), whichever came first. Animals that exited the study for tumor volume endpoint were documented as euthanized for tumor progression (TP), with the date of euthanasia. The time to endpoint (TTE) for analysis was calculated for each mouse by the following equation:

$$TTE = \frac{\log_{10}(\text{endpoint volume}) - b}{m}$$

where TTE is expressed in days, endpoint volume is expressed in mm$^3$, b is the intercept, and m is the slope of the line obtained by linear regression of a log-transformed tumor growth data set. The data set consisted of the first observation that exceeded the endpoint volume used in analysis and the three consecutive observations that immediately preceded the attainment of this endpoint volume. The calculated TTE is usually less than the TP date, the day on which the animal was euthanized for tumor burden. Animals with tumors that did not reach the endpoint volume were assigned a TTE value equal to the last day of the study. In instances in which the log-transformed calculated TTE preceded the day prior to reaching endpoint or exceeded the day of reaching tumor volume endpoint, a linear interpolation was performed to approximate the TTE. Any animal classified as having died from NTR (non-treatment-related) causes due to accident (NTRa) or due to unknown etiology (NTRu) were excluded from TTE calculations (and all further analyses). Animals classified as TR (treatment-related) deaths or NTRm (non-treatment-related death due to metastasis) were assigned a TTE value equal to the day of death.

Treatment Outcome: Treatment outcome was evaluated from tumor growth delay (TGD), which is defined as the increase in the median time to endpoint (TTE) in a treatment group compared to the control group:

$$TGD = T - C$$

expressed in days, or as a percentage of the median TTE of the control group:

$$\% TGD = \frac{T - C}{C} \times 100$$

where T=median TTE for a treatment group, and C=median TTE for the designated control group.

Treatment Efficacy: Treatment efficacy may be determined from the tumor volumes of animals remaining in the study on the last day. The MTV (n) was defined as the median tumor volume on the last day of the study in the number of animals remaining (n) whose tumors had not attained the endpoint volume. Treatment efficacy may also be determined from the incidence and magnitude of regression responses observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 mm$^3$ for one or more of these three measurements. In a CR response, the tumor volume was less than 13.5 mm$^3$ for three consecutive measurements during the course of the study. An animal with a CR response at the termination of a study is additionally classified as a tumor-free survivor (TFS). Animals were monitored for regression responses.

Statistics: Prism (GraphPad) for Windows 6.07 was used for graphical presentations and statistical analyses. The logrank test, which evaluates overall survival experience, was used to analyze the significance of the differences between the TTE values of two groups. Logrank analysis includes the data for all animals in a group except those assessed as NTR deaths. Two-tailed statistical analyses were conducted at significance level P=0.05. Group median tumor volumes were plotted as a function of time. When an animal exited the study due to tumor burden, the final tumor volume recorded for the animal was included with the data used to calculate the median volume at subsequent time points. Kaplan-Meier plots show the percentage of animals in each group remaining in the study versus time.

Animals in Example 1 were treated in accordance with the protocol described in Table 1. FIG. 1 shows the median tumor growth curves for all study groups and FIG. 2 shows the median tumor volumes for the combination of HBI-8000 at 50 mg/kg plus PD-L1 inhibitor antibody antibody vs. the single agent and vehicle controls. FIG. 3 depicts the Kaplan Meier plots for all groups, and FIG. 4 depicts the Kaplan Meier plots for the combination of HBI-8000 at 50 mg/kg plus PD-L1 inhibitor antibody antibody vs. the single agent controls. Table 2.1 describes the values calculated for TTE and % TGD for each treatment group.

TABLE 2.1

Median TTE and % TGD

| Group | n | Treatment Regimen Agent 1 | Agent 2 | Median TTE | % TGD |
|---|---|---|---|---|---|
| 1 | 10 | vehicle | — | 20.5 | — |
| 2 | 10 | HBI-8000 (20 mpk) | — | 18.9 | −8 |
| 3 | 10 | HBI-8000 (50 mpk) | — | 22.8 | 11 |
| 4 | 10 | anti-PDL-1 | — | 21.7 | 6 |
| 5 | 10 | HBI-8000 (20 mpk) | anti-PDL-1 | 25.5 | 24 |
| 6 | 10 | HBI-8000 (50 mpk) | anti-PDL-1 | 33.2 | 62 |

Example 2

In the present example, HBI-8000 was tested as monotherapy and in combination with PD-L1 inhibitor antibody at 5 mg/kg. The experiment included a vehicle-treated group and a PD-L1 inhibitor antibody monotherapy group, which served as the control groups for analysis of efficacy. Tumors were measured twice per week until the study was ended on Day 50. Each animal was euthanized when its tumor attained the endpoint tumor volume of 1000 mm$^3$ or on the final day of the study, whichever came first, and the time to endpoint (TTE) for each mouse was calculated. Treatment response was determined from an analysis of percent tumor growth delay (% TGD), defined as the percent increase in the median time to endpoint (TTE) for treated versus control mice; and by logrank significance of differences in survival among groups and regression responses.

Mice: Details of the animals used in this example can be found in Example 1.

Tumor Cell Culture: Details of the tumor cells used in this example can be found in Example 1.

Tumor Implantation and Measurement: Details of tumor implantation and measurement of tumor growth used in this example can be found in paragraph Example 1. In this example, each mouse was inoculated subcutaneously in the right flank with 5×10$^5$ cells (0.1 mL of cell suspension).

Test Articles: Details of the test articles used in this example can be found in Example 1.

Dosing Solutions: Details of the dosing solutions used in this example can be found in Example 1.

Treatment: Four groups of C57BL/6 mice (n=10) were dosed according to the protocol in Table 3. Dosing began on day 1 unless otherwise noted. HBI-8000 was administered p.o. at 50 mg/kg. PD-1 inhibitor antibody and anti-PDL-1 were each administered i.p. at 5 mg/kg. Vehicle (0.2% carboxymethyl cellulose: 0.1% Tween 80 in deionized water) was administered p.o. All agents were delivered in a dosing volume of 10 mL/kg adjusted per body weight of the individual animals.

TABLE 3

| Group | Treatment | Frequency |
|---|---|---|
| Group 1 | Vehicle (2% CMC: 0.1% Tween 80) | p.o., qd × 21 |
| Group 2 | HBI-8000 at 50 mg/kg | p.o., qd × 21 |
| Group 3 | PD-L1 inhibitor antibody at 5 mg/kg | i.p., biwk × 3 |
| Group 4 | HBI-8000 at 50 mg/kg plus PD-L1 inhibitor antibody at 5 mg/kg | p.o., qd × 21 i.p., biwk × 3 |

Tumor Growth Delay: Details of the tumor growth delay measurements and calculations can be found in Example 1.

Treatment Outcome: Details of treatment outcome measurements and calculations can be found in Example 1.

Treatment Efficacy: Details of treatment efficacy measurements and calculations can be found in Example 1.

Statistics: Details of the statistics and software used in this study can be found in Example 1. FIG. 5 shows the median tumor volume measurements for all groups, and FIG. 6 shows the Kaplan-Meier plot, depicting the percentage of animals in each group remaining in the study versus time. Table 3.1 describes the values calculated for TTE and % TGD for each treatment group.

TABLE 3.1

TTE and % TGD

| Group | n | Agent | Schedule | Agent | Schedule | Median TTE | % TGD |
|---|---|---|---|---|---|---|---|
| 1 | 10 | vehicle | qd × 21 | — | — | 17.5 | — |
| 2 | 10 | HBI-8000 | qd × 21 | — | — | 28.4 | 62 |
| 4 | 10 | anti-PDL-1 | biwk × 3 | — | — | 25.7 | 47 |
| 6 | 10 | HBI-8000 | qd × 21 | anti-PDL-1 | biwk × 3 | 48.8 | 179 |

Example 3

In this model, a proportion of the animals treated 1st line with the PD-1 checkpoint inhibitor antibody experience complete tumor regression. However, a similar proportion of animals treated 1st line with the PD-1 inhibitor antibody experience rapid tumor progression. The balance of the animals treated in this way experience slow tumor progression or stable disease, which is a result which approximates the situation in a number of human cancer patients receiving PD-1 inhibitor antibody therapy, i.e., they experience a transient partial response, including stable disease, but then develop resistance and rapidly progress, failing PD-1 inhibitor antibody therapy. In this example, the efficacy of HBI-8000 (DZ1) as a second-line therapy, alone and in combination with PDL-1 inhibitor antibody 10F.9G2 (anti-PDL-1), was evaluated for the ability to cause tumor growth delay (TGD) in animals which tumors progressed following PD-1 inhibitor antibody first line of therapy in the MC38 murine colon carcinoma syngeneic model in immunocompetent C57BL/6 mice. Hence, addressing a need in the clinic for human patients failing PD-1 inhibitor antibody therapy.

Female C57BL/6 mice bearing subcutaneous MC38 tumors (mean tumor volume: 114 mm$^3$ when treatment began) were treated with a first line of therapy of PD-1 inhibitor antibody treatment, administered intraperitoneally (i.p.) at 5 mg/kg, twice weekly for two weeks (biwk×2). When tumors met the failure criteria and showed two consecutive increases in tumor volume and tumor volume was <500 mm$^3$, these were subsequently reenrolled in a second line of therapy efficacy study, which consisted of six groups (n=10 per group) of mice (MC38-e094-e099 studies). Dosing began on Dl, which represented the day of recruitment and varied among mice (this was normalized for each group). The second line therapies were as follows. Vehicle was administered orally (p.o.). HBI-8000 was administered p.o. at 50 mg/kg. PD-1 inhibitor antibody and anti-PDL-1 were each administered intraperitoneally (i.p) at 5 mg/kg. Group 1 mice served as controls and received 0.2% carboxymethyl cellulose: 0.1% Tween 80 in deionized water (vehicle) once daily for twenty-one days (qd×21). Group 2 received HBI-8000 qd×21. Group 3 received a second course of PD-1 inhibitor antibody biwk×2. Group 4 received HBI-8000 qd×21 and PD-1 inhibitor antibody biwk×2. Group 5 received anti-PDL-1 biwk×2. Group 6 received HBI-8000 qd×21 and anti-PDL-1 biwk×2. The study endpoint was a tumor volume of 1500 mm$^3$ or 45 days, whichever came first. Tumor measurements were taken twice weekly until D44 with individual animals exiting the study upon reaching the tumor volume endpoint.

Mice: At the onset of the initial PD-1 inhibitor antibody treatment, female C57BL/6 mice (Charles River) were eight weeks old and had a BW range of 18.1-24.1 g. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated Enrich-o'cobs™ bedding in static microisolators on a 12-hour light cycle at 20-22° C. (68-72° F.) and 40-60% humidity.

Tumor Implantation and Measurement: Details of tumor implantation and measurement of tumor growth used in this example can be found in paragraph Example 1. In this example, each mouse was inoculated subcutaneously in the right flank with 5×10$^5$ cells (0.1 mL of cell suspension).

Test Articles: HUYA Bioscience International provided HBI-8000 (Lot No. 1384:0033). PD-1 inhibitor antibody RMPI-14 (Lot No. 5611-10/0615) and PDL-1 antibody 10F.9G2 (anti-PDL-1, Lot No. 5786-7-8/0815) were purchased from Bio X cell (West Lebanon, N. H.). All agents were prepared according to protocol instructions.

HBI-8000 was prepared by diluting in 0.2% CMC: 0.1% Tween 80 to yield a 5 mg/mL dosing solution. Dosing solutions were prepared fresh weekly and stored at 4° C. PD-1 inhibitor antibody antibody dosing solution was prepared by diluting an aliquot of the stock (8.62 mg/mL) to 0.5 mg/mL in sterile PBS. The dosing solution was prepared twice weekly and stored at 4° C. Anti-PDL-1 antibody dosing solution was prepared by diluting an aliquot of the stock (5.37 mg/mL) to 0.5 mg/mL in sterile PBS. The anti-PDL-1 antibody dosing solution was prepared twice weekly and stored at 4° C.

Treatment: For the initial PD-1 inhibitor antibody failure part of this study, 120 C57BL/6 mice were dosed i.p. with first line PD-1 inhibitor antibody at 5 mg/kg, biwk×2. Animals meeting the criteria for reenrollment comprised the efficacy study; this included animals with two consecutive increases in tumor volume and tumor volumes below 500 mm³. The first sixty animals that became available were placed sequentially into six efficacy groups until groups were filled; this occurred either sixteen or twenty-two days following initiation of first line dosing. For the efficacy study, six groups of C57BL/6 mice (n=10) were dosed according to protocol in Table 4. Second-line therapy began on day 1, which was the day of enrollment of each individual animal.

TABLE 4

| Group | Treatment | Frequency |
| --- | --- | --- |
| Group 1 | Vehicle (2% CMC: 0.1% Tween 80) | p.o., qd × 21 |
| Group 2 | HBI-8000 at 50 mg/kg | p.o., qd × 21 |
| Group 3 | PD-1 inhibitor antibody at 5 mg/kg | i.p., biwk × 3 |
| Group4 | HBI-8000 at 50 mg/kg plus PD-1 inhibitor antibody at 5 mg/kg | p.o., qd × 21 i.p., biwk × 3 |
| Group 5 | PD-L1 inhibitor antibody at 5 mg/kg | i.p., biwk × 3 |
| Group 6 | HBI-8000 at 50 mg/kg plus PD-L1 inhibitor antibody at 5 mg/kg | p.o., qd × 21 i.p., biwk × 3 |

Tumor Growth Delay: Details of the tumor growth delay measurements and calculations can be found in Example 1.

Treatment Outcome: Details of treatment outcome measurements and calculations can be found in Example 1.

Treatment Efficacy: Details of treatment efficacy measurements and calculations can be found in Example 1.

Statistics: Details of the statistics and software used in this study can be found in Example 1. Table 5 shows the responses of each group, categorized as no response (NR), partial response (PR) and complete response (CR), to the therapy received. FIG. 7 depicts the mean tumor volume measurements for all groups and FIG. 8 depicts the Kaplan-Meier plot, showing the percentage of animals in each group remaining in the study versus time.

TABLE 5

Response Rates to Different Treatments in Mice Bearing Progressing MC38 Tumors After Failing Initial Therapy with PD-1 inhibitor antibody in Example 3

|  | Vehicle | HBI-8000 | PD-1 | PD-1 + HBI-8000 | PD-L1 | PD-L1 + HI31-8000 |
| --- | --- | --- | --- | --- | --- | --- |
| NR | 100% | 40% | 60% | 13% | 33% | 30% |
| PR | 0% | 40% | 30% | 88% | 44% | 20% |
| CR | 0% | 20% | 10% | 0% | 22% | 50% |

Example 4—HDAC Enzyme Inhibition Assay

Selectivity and potency assays of chidamide inhibition of HDAC isotypes are performed using human recombinant HDAC proteins and as described in Ning et al. All of the enzymatic reactions were incubated for 17 h at room temperature in 50 µl of reaction mixture containing HDAC assay buffer (BPS catalog number 50031), 5 µg BSA, an HDAC substrate, a purified recombinant HDAC enzyme and a test compound at a pre-defined concentration. After enzymatic reactions, 50 µl of 29 HDAC Developer (BPS catalog number 50030) is added to each well and the plate is incubated at room temperature for an additional 20 min. Fluorescence intensity is measured at an excitation of 360 nm and an emission of 460 nm using a Synergy™ 2 microplate reader from BioTek (Winooski, Vt., USA). Each compound concentration is performed in duplicate. The $IC_{50}$ values are determined by analyzing concentration-response inhibition curves.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A method for treating colorectal cancer in a subject, comprising administering to the subject a therapeutically effective amount of a histone deacetylase inhibitor (HDAC inhibitor) in combination with a PD-L1 antibody, and the HDAC inhibitor is a compound of formula Ia:

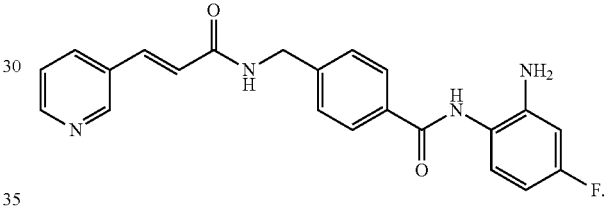

2. The method of claim 1, wherein the subject is treatment naive.

3. The method of claim 1, wherein the subject is immune checkpoint treatment naive.

4. The method of claim 1, wherein the HDAC inhibitor is administered in combination with the PD-L1 antibody as a first line therapy.

5. The method of claim 1, wherein the HDAC inhibitor is administered in combination with the PD-L1 antibody as a second, third, fourth, fifth, or sixth line of treatment.

6. The method of claim 1, wherein the subject has been treated with at least one anti-cancer therapy or anti-cancer agent.

7. The method of claim 1, wherein the subject has received at least one anti-cancer therapy, which is chemotherapy, radiotherapy, surgery, targeted therapy, immunotherapy, or a combination thereof.

8. The method of claim 1, wherein the cancer is resistant or refractory to treatment with at least one anti-cancer agent.

9. The method of claim 1, wherein the PD-L1 antibody is durvalumab, avelumab, atezolizumab, BMS-936559, STI-A1010, STI-A1011, STI-A1012, STI-A1013, STI-A1014, or STI-A1015.

10. The method of claim 1, wherein the PD-L1 antibody is durvalumab, avelumab, atezolizumab, or BMS-936559.

11. A pharmaceutical composition comprising an HDAC inhibitor and a PD-L1 antibody, wherein the HDAC inhibitor is a compound of formula Ia:

12. A kit comprising an HDAC inhibitor and a PD-L1 antibody, wherein the HDAC inhibitor is a compound of formula Ia:

* * * * *